US010233502B2

(12) United States Patent
Badve et al.

(10) Patent No.: US 10,233,502 B2
(45) Date of Patent: Mar. 19, 2019

(54) COMPOSITIONS FOR AND METHODS OF DETECTING, DIAGNOSING, AND PROGNOSING THYMIC CANCER

(75) Inventors: Sunil Badve, Indianapolis, IN (US); Yesim Gokmen-Polar, Noblesville, IN (US); Patrick J. Loehrer, Indianapolis, IN (US); Robert Cook, Friendswood, TX (US); Derek Maetzold, Friendswood, TX (US)

(73) Assignees: Indiana University Research and Technology Corporation, Indianapolis, IN (US); Castle Biosciences, Incorporated, Friendswood, TX (US)

( * ) Notice: Subject to any disclaimer, the term of this patent is extended or adjusted under 35 U.S.C. 154(b) by 0 days.

(21) Appl. No.: 14/128,279

(22) PCT Filed: Jun. 22, 2012

(86) PCT No.: PCT/US2012/043814
§ 371 (c)(1),
(2), (4) Date: Dec. 20, 2013

(87) PCT Pub. No.: WO2012/178058
PCT Pub. Date: Dec. 27, 2012

(65) Prior Publication Data
US 2014/0371081 A1    Dec. 18, 2014

Related U.S. Application Data

(60) Provisional application No. 61/585,663, filed on Jan. 12, 2012, provisional application No. 61/499,988, filed on Jun. 22, 2011.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57407* (2013.01); *C12Q 2600/112* (2013.01); *C12Q 2600/118* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| 6,410,020 B1 * | 6/2002 | Kamada | C07K 16/18 424/130.1 |
| 2006/0084082 A1 * | 4/2006 | Ruben et al. | 435/6 |
| 2006/0234258 A1 * | 10/2006 | Saito | C12Q 1/6806 435/6.14 |
| 2007/0059745 A1 * | 3/2007 | Sharp | C12Q 1/6883 435/6.14 |

FOREIGN PATENT DOCUMENTS

| WO | WO-2005/014524 A2 | 2/2005 |
| WO | WO-2008/046911 A2 | 4/2008 |
| WO | WO-2008/050356 A1 | 5/2008 |

OTHER PUBLICATIONS

Raulic et al. (2008) Stanniocalcin 2 expression is regulated by hormone signalling and negatively affects breast cancer cell viability in vitro. Journal of Endocrinology, 197:517-529.*
Affymetrix HG-U133A Plus 2.0 Annotation File (Accessed from: <http://www.affymetrix.com/Auth/analysis/downloads/na26/ivt/HG-U133_Plus_2.na26.annot.csv.zip> on Mar. 18, 2013, filtered excerpt, 3 pages).*
Dixon et al. (2007) A genome-wide association study of global gene expression. Nature Genetics, 39(10):1202-1207.*
Hardiman, G. (2004) Microarray platforms—comparisons and contrasts. Pharmacogenomics, 5(5):487-502.*
Dotsch et al. "Quantitative TagMan Real-Time PCR: Diagnostic and Scientific Applications", in: Walker et al., Medical Biomethods Handbook (New Jersey, Humana Press, 2005), pp. 305-313.*
Tokunou et al. (2001) c-MET Expression in Myofibroblasts: Role in Autocrine Activation and Prognostic Significance in Lung Adenocarcinoma. American Journal of Pathology, 158(4):1451-1463 (Year: 2001).*
Kaira, K. et al., "MUC1 expression in thymic epithelial tumors: MUC1 may be useful marker as differential diagnosis between type B3 thymoma and thymic carcinoma", *Virchows Arch.*, 458(5):615-620 (abstract) (online); retrieved from PubMed, PMID:21253760.
International Search Report and Written Opinion from parent PCT application PCT/US2012/043814 dated Oct. 11, 2012.

* cited by examiner

*Primary Examiner* — Neil P Hammell
(74) *Attorney, Agent, or Firm* — Faegre Baker Daniels LLP

(57) ABSTRACT

Biomarkers are provided for detecting, diagnosing and prognosing thymic cancer in individuals having or suspected of having thymic cancer. In addition, kits are provided for measuring expression levels or the presence of the biomarkers associated with thymic cancer for detecting, diagnosing and prognosing thymic cancer. Furthermore, methods are provided for detecting, diagnosing and prognosing thymic cancer in individuals having or suspected of having thymic cancer via the biomarkers.

3 Claims, 29 Drawing Sheets

Specification includes a Sequence Listing.

FIG. 6A
FIG. 6B
FIG. 6C
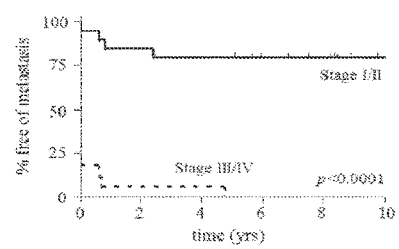
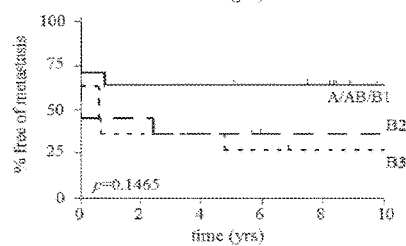
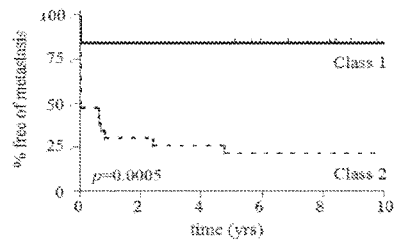
FIG. 6D
FIG. 6E
FIG. 6F
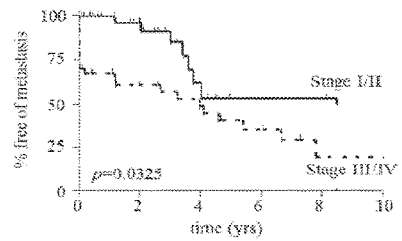
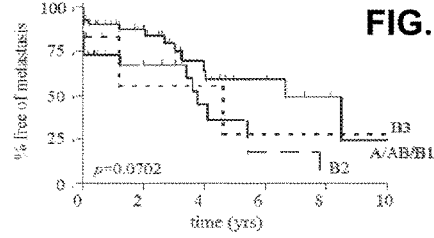
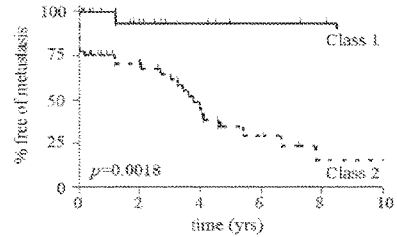

FIG. 7A

<u>Analysis A</u> – PDGFRL, FCGBP, PRRX1, SERPINF1, NGB, SCUBE2, MAB21L2, LEPR, LCA5, GPR98, RSPO3, STC1, STC2, SLC7A11, DACT3, JPH1, AKR1B10, COL11A1, SLC9A2

Validation Set
ROC = 0.8512
Accuracy = 0.7405
Sensitivity = 0.9355
Specificity = 0.5455

Class 1 5yr survival = 93%
Class 1 10yr survival = N/A
Class 2 5yr survival = 35%
Class 2 10yr survival = 16%
P = 0.0018

<u>Analysis B</u> - PDGFRL, FCGBP, PRRX1, SERPINF1, NGB, DACT3, JPH1, AKR1B10, COL11A1, SLC9A2

Validation Set
ROC = 0.8233
Accuracy = 0.7243
Sensitivity = 0.9032
Specificity = 0.5455

Class 1 5yr survival = 75%
Class 1 10yr survival = N/A%
Class 2 5yr survival = 39%
Class 2 10yr survival = 14%
P = 0.0123

Training Set
ROC = 0.8921
Accuracy = 0.8190
Sensitivity = 0.9048
Specificity = 0.7333
Class 1 5yr survival = 85%
Class 1 10yr survival = 85%
Class 2 5yr survival = 22%
Class 2 10yr survival = 22%
P = 0.0005

Analysis C - PDGFRL, FCGBP, PRRX1, NGB, DACT3, JPH1, AKR1B10, COL11A1, SLC9A2

Validation Set
ROC = 0.7940
Accuracy = 0.7177
Sensitivity = 0.9355
Specificity = 0.5000

Class 1 5yr survival = 96%
Class 1 10yr survival = N/A%
Class 2 5yr survival = 35%
Class 2 10yr survival = 16%
P = 0.0033

Training Set
ROC = 0.8762
Accuracy = 0.7952
Sensitivity = 0.8571
Specificity = 0.7333
Class 1 5yr survival = 79%
Class 1 10yr survival = 79%
Class 2 5yr survival = 23%
Class 2 10yr survival = 23%
P = 0.0017

|  | Predicted_Class | |  |
|---|---|---|---|
| Count<br>Total %<br>Col %<br>Row % | met | nonmet |  |
| met | 18<br>50.00<br>81.82<br>85.71 | 3<br>8.33<br>21.43<br>14.29 | 21<br>58.33 |
| nonmet | 4<br>11.11<br>18.18<br>26.67 | 11<br>30.56<br>78.57<br>73.33 | 15<br>41.67 |
|  | 22<br>61.11 | 14<br>38.89 | 36 |

Analysis D - PDGFRL, FCGBP, PRRX1, NGB, DACT3, JPH1, AKR1B10, SERPINF1, SLC9A2

Validation Set
ROC = 0.8409
Accuracy = 0.7405
Sensitivity = 0.9355
Specificity = 0.5455
Class 1 5yr survival = 96%
Class 1 10yr survival = N/A%
Class 2 5yr survival = 35%
Class 2 10yr survival = 16%
P = 0.0022

Training Set
ROC = 0.8540
Accuracy = 0.7619
Sensitivity = 0.8571
Specificity = 0.6667

Class 1 5yr survival = 77%
Class 1 10yr survival = 77%
Class 2 5yr survival = 26%
Class 2 10yr survival = 26%
P = 0.0052

|  | Predicted_Class | | |
|---|---|---|---|
| Count<br>Total %<br>Col %<br>Row % | met | nonmet | |
| met | 18<br>50.00<br>78.26<br>85.71 | 3<br>8.33<br>23.08<br>14.29 | 21<br>58.33 |
| nonmet | 5<br>13.89<br>21.74<br>33.33 | 10<br>27.78<br>76.92<br>66.67 | 15<br>41.67 |
|  | 23<br>63.89 | 13<br>36.11 | 36 |

<u>Analysis E</u> - AKR1B10, PDGFRL, FCGBP, COL11A1, SERPINF1, JPH1, SLC9A2, DACT3

Validation Set
ROC = 0.8182
Accuracy = 0.7130
Sensitivity = 0.9032
Specificity = 0.5227
Class 1 5yr survival = 74%
Class 1 10yr survival = N/A%
Class 2 5yr survival = 39%
Class 2 10yr survival = 14%
P = 0.0162

Training Set
ROC = 0.9111
Accuracy = 0.8190
Sensitivity = 0.9048
Specificity = 0.7333

Class 1 5yr survival = 85%
Class 1 10yr survival = 85%
Class 2 5yr survival = 22%
Class 2 10yr survival = 22%
P = 0.0005

SEQUENCE LISTING

```
<160> NUMBER OF SEQ ID NOS: 23

<210> SEQ ID NO 1
<211> LENGTH: 171
<212> TYPE: DNA
<213> ORGANISM: Homo sapiens

<400> SEQUENCE: 1
ctgcctggtc tcgtctggga cctgggacag cagctgggag acctgagcct ggagtctggg      60
```

```
ggcctggaac aggagagcgg gcgtagctcg ggcttctatg aagatcccag ctctacagga    120
ggtccagatt caccaccctc aaccttctgt ggggacagtg gcttctctgg a             171

<210> SEQ ID NO 2
<211> LENGTH: 147
<212> TYPE: DNA
<213> ORGANISM: Homo sapiens

<400> SEQUENCE: 2
gccgctcgcc aggagtgcga catcgcgaga gctgtggcca gggagctgtc acctgatttc    60
taccaaccag gccctgatta cgtcaaacag agatttcagg aaggtgtaga tgctaaagaa    120
aatccagaag aaaaggtacc agaaaag                                        147

<210> SEQ ID NO 3
<211> LENGTH: 191
<212> TYPE: DNA
<213> ORGANISM: Homo sapiens

<400> SEQUENCE: 3
agaccccttg tgaggaaagc ctttgagaag accctcaagg acctgaagct gagctatctg    60
gacgtctatc ttattcactg gccacaggga ttcaagtctg gggatgacct tttccccaaa   120
gatgataaag gtaatgccat cggtggaaaa gcaacgttct ggatgcctg ggaggccatg    180 gaggagctgg t                                                         191

<210> SEQ ID NO 4
<211> LENGTH: 113
<212> TYPE: DNA
<213> ORGANISM: Homo sapiens

<400> SEQUENCE: 4
gatggaccac aaggaccccc agggtctgtt ggttcagttg gtggtgttgg agaaaagggt    60
gaacctggag aagcagggaa cccagggcct cctggggaag caggtgtagg cgg          113

<210> SEQ ID NO 5
<211> LENGTH: 163
<212> TYPE: DNA
<213> ORGANISM: Homo sapiens

<400> SEQUENCE: 5
gtttacgctg gattaccccc acgtgcagat ccccttcgag atcacccttt ggatcctgct    60
ggcctccctg gccaagattg gcttccatct gtatcacaag ttgcccacaa tagtgcctga   120
gagctgcctt cttataatgg ttggacttct actaggtggg att                     163

<210> SEQ ID NO 6
<211> LENGTH: 129
<212> TYPE: DNA
<213> ORGANISM: Homo sapiens

<400> SEQUENCE: 6
tttactgcag ggcggaggcc gggggcagat ctcagatctc cgtcaagtac cagctgctct    60
acgtggcggt tcccagtggc cctccctcaa caaccatctt ggcttcttca aacaaagtga   120
aaagtgggg                                                            129

<210> SEQ ID NO 7
<211> LENGTH: 148
<212> TYPE: DNA
<213> ORGANISM: Homo sapiens
```

<400> SEQUENCE: 7
ctggccacct atgctgctgc atgccaggct gctggagcca cagtgcaccc ctggaggagt    60
gaagaacttt gcccactgag ctgcccaccc cacagccact atgaggcgtg ttcctacggc   120
tgcccgctgt cctgtggaga cctcccag                                      148

<210> SEQ ID NO 8
<211> LENGTH: 135
<212> TYPE: DNA
<213> ORGANISM: Homo sapiens

<400> SEQUENCE: 8
aggctggccg gagcctgctg gagtcgccgg gactcaccag cggcagcgac accccgcagc    60
aggacaatga ccagctgaac tcagaagaaa aaagaagag aaagcagcga aggaatagga    120
caaccttcaa tagca                                                     135

<210> SEQ ID NO 9
<211> LENGTH: 169
<212> TYPE: DNA
<213> ORGANISM: Homo sapiens

<400> SEQUENCE: 9
atgaagagag gaccgtgagg gtccccatga tgtcggaccc taaggctgtt ttacgctatg    60
gcttggattc agatctcagc tgcaagattg cccagctgcc cttgaccgga agcatgagta   120
tcatcttctt cctgccctg aaagtgaccc agaatttgac cttgataga                169

<210> SEQ ID NO 10
<211> LENGTH: 151
<212> TYPE: DNA
<213> ORGANISM: Homo sapiens

<400> SEQUENCE: 10
tgtcctcact ggaggagtac cttgccagcc tgggcaggaa gcaccgggca gtgggtgtga    60
agctcagctc cttctcgaca gtgggtgagt ctctgctcta catgctggag aagtgtctgg   120
gccctgcctt cacaccagcc acacgggctg c                                  151

<210> SEQ ID NO 11
<211> LENGTH: 129
<212> TYPE: DNA
<213> ORGANISM: Homo sapiens

<400> SEQUENCE: 11
ctgcaaggag gggtttttcc tgagtgacaa tcagcacacc tgcattcacc gctcggaaga    60
gggcctgagc tgcatgaata aggatcacgg ctgtagtcac atctgcaagg aggccccaag   120
gggcagcgt                                                            129

<210> SEQ ID NO 12
<211> LENGTH: 187
<212> TYPE: DNA
<213> ORGANISM: Homo sapiens

<400> SEQUENCE: 12
tctggacaca aactttatg taagtcacct gaaataggaa tccggcagaa gaccttcatt    60
aattaagaag caaacaaaaa gagagcaacc caaccaaaac aaatcacatt cttgcacaaa   120
agtgatcgtt ttcttccaaa caatgtgaat ttaaaggtc acacaaaaga agcaatcggg   180

```
ctccgcc                                                                      187
```

```
<210> SEQ ID NO 13
<211> LENGTH: 153
<212> TYPE: DNA
<213> ORGANISM: Homo sapiens

<400> SEQUENCE: 13
ccattgagaa gtaccagttc agtctttacc caatatttat ggaaggagtg ggaaaaccaa            60
agataattaa tagtttcact caagatgata ttgaaaaaca ccagagtgat gcaggtttat          120
atgtaattgt gccagtaatt atttcctctt cca                                       153
```

```
<210> SEQ ID NO 14
<211> LENGTH: 133
<212> TYPE: DNA
<213> ORGANISM: Homo sapiens

<400> SEQUENCE: 14
tttaactcca gaaacaatta tgtgttacga aacaaatgg gaagaaccag acatcttac             60 tttggacttg caatctcaaa agcaagacag gcatggagaa gcagggattc taaacccaat         120
tatggaaaga gaa                                                             133
```

```
<210> SEQ ID NO 15
<211> LENGTH: 125
<212> TYPE: DNA
<213> ORGANISM: Homo sapiens

<400> SEQUENCE: 15 gccctgggg aaaccattca aaccttgttg ttagaggtcc tggctgacga cgttccggag            60
attgaagagg ttatccaagt gcaactaact gatgcctctg gtggaggtac tattgggtta         120
gatcg                                                                      125
```

```
<210> SEQ ID NO 16
<211> LENGTH: 155
<212> TYPE: DNA
<213> ORGANISM: Homo sapiens

<400> SEQUENCE: 16
ttggcttttt atcattttga acttatgga atacatcggc agccaaaacg cctcccgggg            60
aaggcgccag cgaagaatgc atcctaacgt tagtcaaggc tgccaaggag gctgtgcaac         120
atgctcagat tacaatggat gtttgtcatg taagc                                     155
```

```
<210> SEQ ID NO 17
<211> LENGTH: 163
<212> TYPE: DNA
<213> ORGANISM: Homo sapiens

<400> SEQUENCE: 17
cagtgcttct gcaacccatg aggcggagca gaatgactct gtgagcccca ggaaatcccg           60
agtggcggct caaaactcag ctgaagtggt tcgttgcctc aacagtgctc tacaggtcgg         120
ctgcggggct tttgcatgcc tggaaaactc cacctgtgac aca                            163
```

```
<210> SEQ ID NO 18
<211> LENGTH: 145
<212> TYPE: DNA
<213> ORGANISM: Homo sapiens

<400> SEQUENCE: 18
```

```
tgtgagattc ggggcttaca tgggatttgc atgacttttc tgcacaacgc tggaaaattt     60
gatgcccagg gcaagtcatt catcaaagac gccttgaaat gtaaggccca cgctctgcgg    120
cacaggttcg gctgcataag ccgga                                          145
```

```
<210> SEQ ID NO 19
<211> LENGTH: 115
<212> TYPE: DNA
<213> ORGANISM: Homo sapiens

<400> SEQUENCE: 19
tggcctactt tacgaccatt aatgctgagg agctgctgct ttcaaatgca gtggcagtga     60
ccttttctga gcggctactg ggaaatttct cattagcagt tccgatcttt gttgc         115
```

```
<210> SEQ ID NO 20
<211> LENGTH: 143
<212> TYPE: DNA
<213> ORGANISM: Homo sapiens

<400> SEQUENCE: 20
agatgcagag tgtcatgcag ctaaacttct ggaagtcatc attcttcagt gcaaggaag     60 gggaattgat cagtgcattc cactcttcgt tcaacttgtt ttggagagat taactcgagg    120
ggtcaaaact agtgagcttc gta                                            143
```

```
<210> SEQ ID NO 21
<211> LENGTH: 133
<212> TYPE: DNA
<213> ORGANISM: Homo sapiens

<400> SEQUENCE: 21
tagacaatgc tgctttccct ttccttgcat attctggaat cccagcagtt tctttctgtt     60
tttgcgagga cacagattat ccttatttgg gtaccaccat ggacacctat aaggaactga    120
ttgagaggat tcc                                                        133
```

```
<210> SEQ ID NO 22
<211> LENGTH: 143
<212> TYPE: DNA
<213> ORGANISM: Homo sapiens

<400> SEQUENCE: 22
ggcacagcta gttccgtcgc agccgggatt tgggtcgcag ttcttgtttg tggatcgctg     60
tgatcgtcac ttgacaatgc agatcttcgt gaagactctg actggtaaga ccatcaccct    120
cgaggttgag cccagtgaca cca                                            143
```

```
<210> SEQ ID NO 23
<211> LENGTH: 151
<212> TYPE: DNA
<213> ORGANISM: Homo sapiens

<400> SEQUENCE: 23
cctgctggag aacctccgct ttcatgtgga ggaagaaggg aagggaaaag atgcttctgg     60
gaacaaggtt aaagccgagc cagccaaaat agaagctttc cgagcttcac tttccaagct    120
aggggatgtc tatgtcaatg atgcttttgg c                                   151
```

COMPOSITIONS FOR AND METHODS OF DETECTING, DIAGNOSING, AND PROGNOSING THYMIC CANCER

RELATED APPLICATIONS

This application is the U.S. national phase of International Patent Application No. PCT/US2012/043814, filed Jun. 22, 2012, which claims benefit under 35 U.S.C. § 119(e) of United States Provisional Patent Applications Nos. 61/499,998, filed on Jun. 22, 2011, and U.S. Provisional Application No. 61/585,663, filed Jan. 12, 2012, the contents of each of which application is specifically incorporated by reference herein in its entirety.

SEQUENCE LISTING

The instant application contains a Sequence Listing which has been submitted in ASCII format via EFS-Web and is hereby incorporated by reference in its entirety. Said ASCII copy, created on Feb. 8, 2016, is named CBR101_ST25.txt and is 7.25 KB in size.

FIELD OF THE INVENTION

The invention generally relates to medical diagnostics and in particular relates to compositions for and methods of detecting, diagnosing or prognosing an individual having or suspected of having a cancer, such as thymic cancer.

BACKGROUND

Thymomas and thymic carcinomas are rare cancers of the thymic epithelium or thymus gland/thymic tissue. Unfortunately, the heterogeneity of the disease and the lack of molecular targets impair the identification of individuals with higher metastatic risk and the potential for early intervention. Currently, complete surgical resection and Masaoka staging are considered the only favorable prognostic factor for these individuals. However, the literature has examples showing that patients with complete surgical resection or Masaoka stage I do metastasize as well as patients with partial surgical resection or Maskaoka stage II or III who do not metastasize. Thus, these two current prognostic standards lead to undertreatment of individuals having early stage disease as well as overtreatment of indolent tumors diagnosed at a later stage.

Although resection and chemotherapy are effective therapies for most individuals with early stage disease, recurrence is common. A significant number of individuals do not receive adjuvant chemo-radiation therapy until they develop recurrent or metastatic disease. As such, there is a need for methods that allow physicians to detect, diagnose and prognose the expected course of a thymic cancer, including the likelihood of recurrence, long-term survival, and the like, as well as allow physicians to select the most appropriate treatment regimen. Additionally, compositions that target novel pathways involved in tumor formation also are needed.

BRIEF SUMMARY

Compositions are provided for detecting, diagnosing and prognosing cancer in an individual having or suspected of having a cancer, such as a thymic cancer. In one aspect, the composition can be a kit for detecting, diagnosing and/or prognosing thymic cancer, the kit having a plurality of probes and/or oligonucleotide primer pairs, where each of the probes or oligonucleotide primer pairs specifically binds to one distinct biomarker, fragment or variant thereof described herein.

Methods are also provided for detecting, diagnosing and prognosing cancer and predicting the likelihood of metastasis in an individual having or suspected of having a cancer, such as a thymic cancer. In one aspect, the method can include measuring expression levels of nucleic acid transcripts or expression products thereof of a plurality of biomarkers in a sample from an individual having or suspected of having a cancer such as a thymic cancer, where the biomarkers can be a combination of the biomarkers as described herein, when compared to a control/reference.

The compositions and methods therefore find use in detecting, predicting and diagnosing an early stage cancer, such as thymic cancer, as well as find use in prognosing an individual having thymic cancer, which can be used to determine an appropriate treatment regimen.

These and other features, objects and advantages of the present invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The features, objects and advantages other than those set forth above will become more readily apparent when consideration is given to the detailed description below. Such detailed description makes reference to the following drawings, wherein:

FIGS. 6A-6F show Kaplan-Meier curves for metastasis free survival (MFS) in training set (FIGS. 6A-6C) and validation set (FIGS. 6D-6F) cohort of samples. MFS is grouped according to Masaoka staging (FIGS. 6A, 6D), WHO classification (FIGS. 6B, 6E) or predicted GEP class as determined by Radial Basis Machine predictive modeling algorithm (FIGS. 6C, 6F). Area under the receiver operating characteristic (ROC) curve for the GEP prediction model was 0.89 and 0.84 for training and validation sets, respectively. P-value for curves was calculated according to Log-Rank method.

Figure 7A:
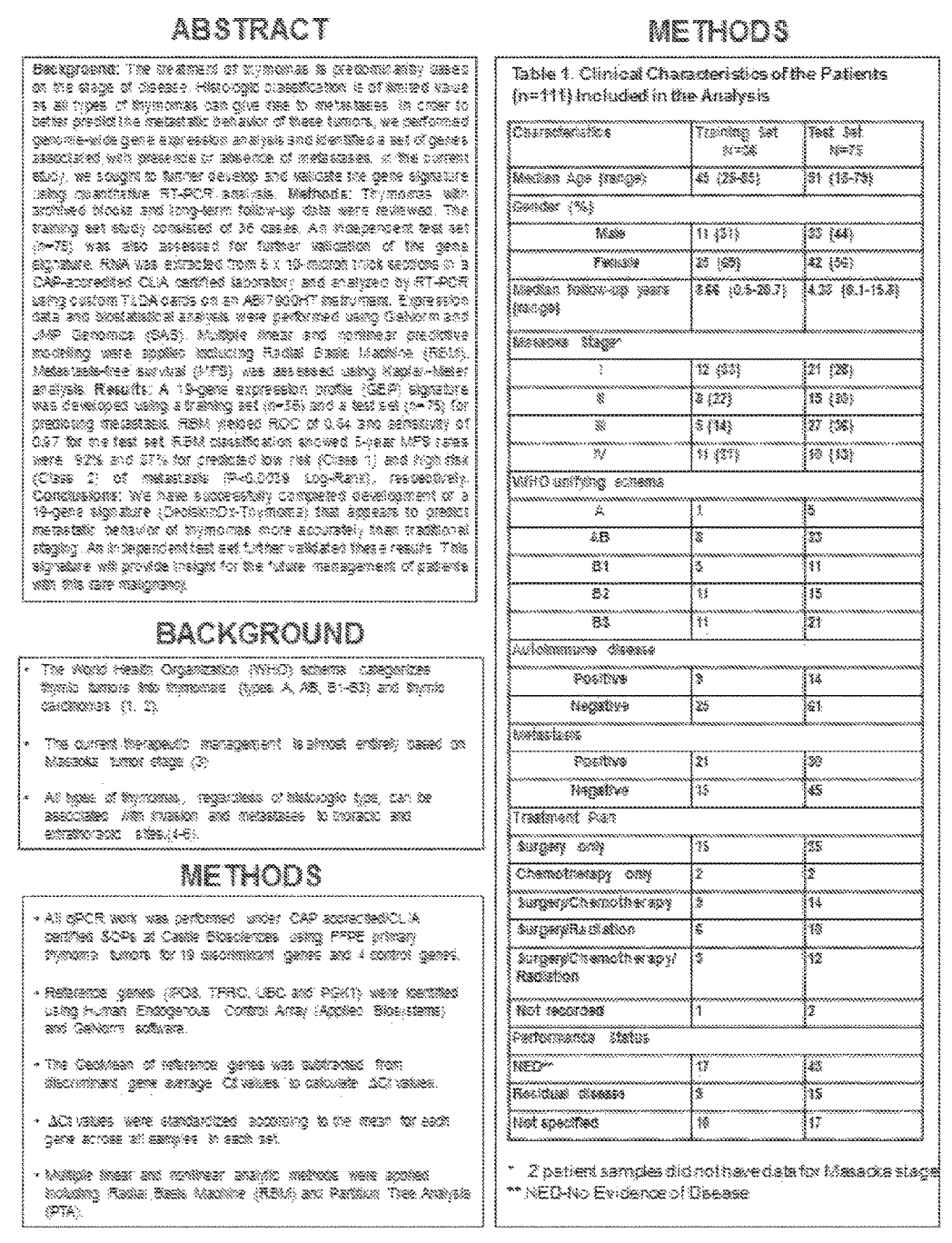

FIGS. 7A-7D provides additional analyses of the prognostic gene expression signature results shown in FIG. 6.

Figure 1:
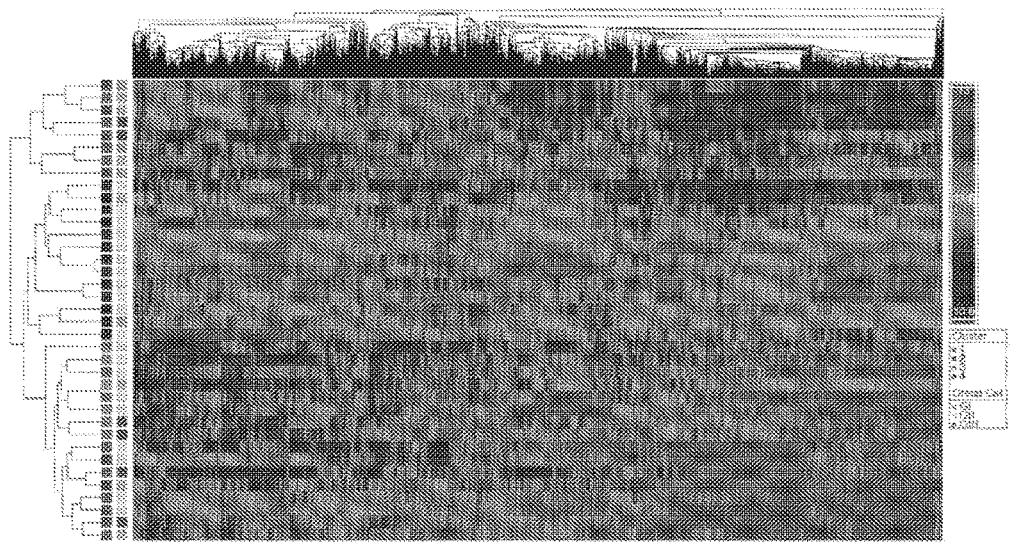
FIG. 1 shows an unsupervised hierarchical clustering of the thirty-six thymic tumors (and one duplicate) showing four distinct clusters (C1-C4). 8,260 genes had signals significantly above background. The data was normalized using quantile normalization. Histologic subtypes of patient samples also are included. Group I (GI): A/AB; Group II (GII): B1/B2; and Group III (GIII): B3.

While the invention is susceptible to various modifications and alternative forms, exemplary embodiments thereof are shown by way of example in the drawings and are described in detail below. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments herein and appended claims. Reference therefore should be made to the embodiments herein and appended claims for interpreting the scope of the invention.

DETAILED DESCRIPTION OF PREFERRED EMBODIMENTS

The compositions and methods now will be described more fully hereinafter with reference to the accompanying drawings, in which some, but not all embodiments are shown.

Although specific terms are employed herein, they are used in a generic and descriptive sense only and not for purposes of limitation. As such, unless defined otherwise, all technical and scientific terms used herein have the same meaning as commonly understood by one of skill in the art to which the invention pertains. Although any materials and methods similar to or equivalent to those described herein can be used in the practice or testing of the invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

The term "altered amount" of a marker or "altered level" of a marker refers to increased or decreased copy number of the marker and/or increased or decreased expression level of a particular marker gene or genes in a cancer sample, as compared to the expression level or copy number of the marker in a control sample. The term "altered amount" of a marker also includes an increased or decreased protein level of a marker in a sample, e.g., a cancer sample, as compared to the protein level of the marker in a normal, control sample.

The term "altered level of expression" of a marker refers to an expression level or copy number of a marker in a test sample e.g., a sample derived from a subject suffering from cancer, that is greater or less than the control of the assay employed to assess expression or copy number, and may be at least 1.1, and in some embodiments may be 1.2, 1.3, 1.4, 1.5, 1.6, 1.7, 1.8, 1.9, two, three, four, five or ten or more times the expression level or copy number of the marker or chromosomal region in a control sample (e.g., sample from a healthy subject not having the associated disease) and, in some embodiments, the average expression level or copy number of the marker or chromosomal region in several control samples. The altered level of expression is greater or less than the standard error of the assay employed to assess expression or copy number, and is, in some embodiments, at least 1.1, and, in some embodiments may be 1.2, 1.3, 1.4, 1.5, 1.6, 1.7, 1.8, 1.9, two, three, four, five or ten or more times the expression level or copy number of the marker in a control sample (e.g., sample from a healthy subject not having the associated disease) and, in some embodiments may be, the average expression level or copy number of the marker in several control samples.

The term "altered activity" of a marker refers to an activity of a marker which is increased or decreased in a disease state, e.g., in a cancer sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker, or altered interaction with transcriptional activators or inhibitors.

The term "altered structure" of a marker refers to the presence of mutations or allelic variants within the marker gene or maker protein, e.g., mutations which affect expression or activity of the marker, as compared to the normal or wild-type gene or protein. For example, mutations include, but are not limited to substitutions, deletions, or addition mutations. Mutations may be present in the coding or non-coding region of the marker.

The term "altered subcellular localization" of a marker refers to the mislocalization of the marker within a cell relative to the normal localization within the cell e.g., within a healthy and/or wild-type cell. An indication of normal localization of the marker can be determined through an analysis of subcellular localization motifs known in the field that are harbored by marker polypeptides.

The "amount" of a marker, e.g., expression or copy number of a marker or MCR, or protein level of a marker, in a subject is "significantly" higher or lower than the normal amount of a marker, if the amount of the marker is greater or less, respectively, than the normal level by an amount greater than the control of the assay employed to assess amount, and, in some embodiments may be, at least 1.1, and, in some embodiments may be, 1.2, 1.3, 1.4, 1.5, 1.6, 1.7, 1.8, 1.9, two, three, four, five, ten or more times that amount. Alternately, the amount of the marker in the subject can be considered "significantly" higher or lower than the normal amount if the amount is at least about two, and in some embodiments may be at least about three, four, or five times, higher or lower, respectively, than the normal amount of the marker.

The terms "amplification" or "amplify" include the reactions necessary to increase the number of copies of a nucleic acid sequence (e.g., a DNA sequence). For the purposes of this invention, amplification refers to the in vitro exponential increase in copy number of a target nucleic acid sequence, such as that mediated by a polymerase amplification reaction such as, e.g., PCR, however, other amplification reactions encompassed by the invention include, e.g., RT-PCR (see, e.g., U.S. Pat. No. 4,683,202; Mullis et al.), and the ligase chain reaction (Barany, Proc. Natl. Acad. Sci. USA 88:189-193 (1991)).

The term "biochip" refers to a solid substrate comprising an attached probe or plurality of probes of the invention, wherein the probe(s) comprise at least 1, 2, 3, 4, 5, 6, 7, 8, 9, 10, 11, 12, 13, 14, 15, 16, 17, 18, 19, 20, 25, 30, 35, 40, 45, 50, 100, 150, 200 or more probes. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a single disorder. The probes may be attached to the biochip in a wide variety of ways, as will be appreciated by those in the art. The probes may either be synthesized first, with subsequent attachment to the biochip, or may be directly synthesized on the biochip. The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing. The substrate may be planar, although other configurations of substrates may be used as well. For example, probes may be placed on the inside surface of a tube, for flow-through sample analysis to minimize sample volume. Similarly, the substrate may be flexible, such as a flexible foam, including closed cell foams made of particular plastics. The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide. The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, peritoneal fluid, pus, saliva, sebum, semen, serum, sweat, synovial fluid, tears, urine, vaginal lubrication, vitreous humor, vomit).

The term "classifying" includes "to associate" or "to categorize" a sample with a disease state. In certain instances, "classifying" is based on statistical evidence, empirical evidence, or both. In certain embodiments, the methods and systems of classifying use of a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care therapy for thymic cancer). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, for example, standard of care therapy for thymic cancer, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), patients undergoing thymic cancer therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

The term "diagnosing cancer" includes the use of the methods, systems, and code of the present invention to determine the presence or absence of a cancer or subtype thereof in an individual. The term also includes methods, systems, and code for assessing the level of disease activity in an individual.

As used herein, the term "diagnostic marker" or "diagnostic biomarker" includes markers described herein which are useful in the diagnosis of cancer, e.g., over- or underactivity, emergence, expression, growth, remission, recurrence or resistance of tumors before, during or after therapy. The predictive functions of the marker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression (e.g., by ISH, Northern Blot, or qPCR), increased or decreased protein level (e.g., by IHC), or increased or decreased; (2) its presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its presence or absence in clinical subset of subjects with cancer (e.g., those responding to a particular therapy or those developing resistance). Diagnostic markers also include "surrogate markers," e.g., markers which are indirect markers of cancer progression.

A molecule is "fixed" or "affixed" to a substrate if it is covalently or non-covalently associated with the substrate such the substrate can be rinsed with a fluid (e.g. standard saline citrate, pH 7.4) without a substantial fraction of the molecule dissociating from the substrate.

The term "gene expression data" or "gene expression level" as used herein refers to information regarding the relative or absolute level of expression of a gene or set of genes in a cell or group of cells. The level of expression of a gene may be determined based on the level of RNA, such as mRNA, encoded by the gene. Alternatively, the level of expression may be determined based on the level of a polypeptide or fragment thereof encoded by the gene. Gene expression data may be acquired for an individual cell, or for a group of cells such as a tumor or biopsy sample. Gene expression data and gene expression levels can be stored on computer readable media, e.g., the computer readable medium used in conjunction with a microarray or chip reading device. Such gene expression data can be manipulated to generate gene expression signatures.

The term "gene expression signature" or "signature" as used herein refers to a group of coordinately expressed genes. The genes making up this signature may be expressed in a specific cell lineage, stage of differentiation, or during a particular biological response. The genes can reflect biological aspects of the tumors in which they are expressed, such as the cell of origin of the cancer, the nature of the non-malignant cells in the biopsy, and the oncogenic mechanisms responsible for the cancer or pathology thereof (Shaffer et al., Immunity, 15: 375-385 (2001)).

As used herein, the term "inhibit" includes the decrease, limitation, or blockage, of, for example a particular action, function, or interaction. For example, cancer is "inhibited" if at least one symptom of the cancer, such as hyperproliferative growth, is alleviated, terminated, slowed, or prevented. As used herein, cancer is also "inhibited" if recurrence or metastasis of the cancer is reduced, slowed, delayed, or prevented.

The term "label" refers to a molecular moiety capable of detection including, by way of example, without limitation, radioactive labels which can be incorporated by known methods (e.g., nick translation or kinasing), radioactive isotopes, biotin, fluorescent groups, chemiluminescent groups (e.g., dioxetanes, particularly triggered dioxetanes), digoxigenin, enzymes, antibodies, luminescent agents, precipitating agents, dyes, and the like.

The "normal" level of expression of a marker is the level of expression of the marker in cells of a subject, e.g., a human patient, not afflicted with a cancer or with the condition under analysis. An "over-expression" or "significantly higher level of expression" of a marker refers to an expression level in a test sample that is greater than the control of the assay employed to assess expression, and is in some embodiments at least 1.1 times, and in some embodiments may be 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the marker in a control sample (e.g., sample from a healthy subject not having the marker associated disease) and, in some embodiments, the average expression level of the marker in several control samples. A "significantly lower level of expression" of a marker refers to an expression level in a test sample that is at least 1.1 times, and in some embodiments may be 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the marker in a control sample (e.g., sample from a subject who has not experienced recurrence or metastasis relative to a subject who has experienced recurrence or metastasis or a healthy subject not having the marker associated disease) and, in some embodiments, the average expression level of the marker in several control samples.

The term "probe" refers to a structure comprised of a polynucleotide that is capable of selectively binding or forming a hybrid structure with an intended target sequence, due to complementarity of at least one sequence in the probe with a sequence in the target region. The polynucleotide regions of probes can be composed of DNA and/or RNA and/or synthetic nucleotide analogs. Included within probes are "capture probes," "blocking probes," and "label probes." The term "primer" or "nucleic acid primer" or "nucleic acid primer sequence" includes single-stranded oligonucleotides that, typically, are between about 4 to about 100 bases, or alternatively between about 17 to 30 bases, or alternatively 20 or more bases, and are designed to hybridize with a corresponding template nucleic acid. Primer molecules can be complementary to either the sense or the anti-sense strand of a template nucleic acid and are typically used as complementary pairs that flank a nucleic acid region of interest. Probes can be either synthesized by one skilled in the art, or derived from appropriate biological preparations. For purposes of detection of the target molecule, probes can be specifically designed to be labeled, as described herein. Examples of molecules that can be utilized as probes include, but are not limited to, RNA, DNA, proteins, antibodies, and organic molecules.

The term "response to cancer therapy" or "outcome of cancer therapy" relates to any response of the hyperproliferative disorder (e.g., cancer) to a cancer therapy, preferably to a change in tumor mass and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Response may also be assessed by caliper measurement or pathological examination of the tumor after biopsy or surgical resection for solid cancers. Responses may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to copy number, level of expression, level of activity, etc. of one or more biomarkers described herein that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom the measurement values are known. In certain embodiments, the same doses of cancer therapeutic agents are administered to each subject. In related embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker threshold values that correlate to outcome of a cancer therapy can be determined using methods such as those described in the Examples section. Outcomes can also be measured in terms of a "hazard ratio" (the ratio of death rates for one patient group to another; provides likelihood of death at a certain time point), "overall survival" (OS), and/or "progression free survival." In certain embodiments, the prognosis comprises likelihood of overall survival rate at 1 year, 2 years, 3 years, 4 years, or any other suitable time point. The significance associated with the prognosis of poor outcome in all aspects of the present invention is measured by techniques known in the art. For example, significance may be measured with calculation of odds ratio. In a further embodiment, the significance is measured by a percentage. In one embodiment, a significant risk of poor outcome is measured as odds ratio of 0.8 or less or at least about 1.2, including by not limited to: 0.1, 0.2, 0.3, 0.4, 0.5, 0.6, 0.7, 0.8, 1.2, 1.3, 1.4, 1.5, 1.6, 1.7, 1.8, 1.9, 2.0, 2.5, 3.0, 4.0, 5.0, 10.0, 15.0, 20.0, 25.0, 30.0 and 40.0. In a further embodiment, a significant increase or reduction in risk is at least about 20%, including but not limited to about 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, and greater, or any range in between, with respect to a relevant outcome (e.g., accuracy, sensitivity, specificity, 5-year survival, 10-year survival, metastasis-free survival, stage prediction, and the like). In a further embodiment, a significant increase in risk is at least about 50%. Thus, the present invention further provides methods for making a treatment decision for a cancer patient, comprising carrying out the methods for prognosing a cancer patient according to the different aspects and embodiments of the present invention, and then weighing the results in light of other known clinical and pathological risk factors, in determining a course of treatment for the cancer patient. For example, a cancer patient that is shown by the methods of the invention to have an increased risk of poor outcome by combination chemotherapy treatment can be treated with more aggressive therapies, including but not limited to radiation therapy, peripheral blood stem cell transplant, bone marrow transplant, or novel or experimental therapies under clinical investigation. In addition, it will be understood that the cancer therapy responses can be predicted by the methods described herein according to enhanced sensitivity and/or specificity criteria. For example, sensitivity and/or specificity can be at least 0.80, 0.81, 0.2, 0.83, 0.84, 0.85, 0.86, 0.87, 0.88, 0.89, 0.90, 0.91, 0.92, 0.93, 0.94, 0.95, 0.96, 0.97, 0.98, 0.99 or greater, any range in between, or any combination for each of sensitivity and specificity.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a thymoma sample or surgical resection tissue. In certain instances, the method of the present invention further comprises obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., chemotherapeutic or radiation therapy. In some embodiments, normal cells are not affected to an extent that causes the normal cells to be unduly injured by the cancer therapy (e.g., chemotherapy or radiation therapy). An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

The term "subject" refers in one embodiment to an animal in need of therapy for, or susceptible to, a condition or its sequelae. The subject can include dogs, cats, pigs, cows, sheep, goats, horses, rats, mice, monkeys, and humans. The term "subject" does not exclude an individual that is normal in all respects.

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "target nucleic acid" or "template" includes any nucleic acid intended to be detected, copied, and the like in, e.g., a polymerase amplification reaction, such as PCR.

The term "targeting polynucleotide sequence" as used herein, refers to a polynucleotide sequence which is comprised of nucleotides which are complementary to a target nucleotide sequence such that the sequence is of sufficient length and complementarity with the target sequence to form a duplex which has sufficient stability for the purpose intended.

An "underexpression" or "significantly lower level of expression or copy number" of a marker refers to an expression level or copy number in a test sample that is greater than the control of the assay employed to assess expression or copy number, but is in some embodiments at least 1.1, and in some embodiments 1.2, 1.3, 1.4, 1.5, 1.6, 1.7, 1.8, 1.9, two, three, four, five or ten or more times less than the expression level or copy number of the marker in a control sample (e.g., sample from a subject who has not experienced recurrence or metastasis relative to a subject who has experienced recurrence or metastasis or a healthy subject not afflicted with cancer) and, in some embodiments, the average expression level or copy number of the marker in several control samples.

Overview

Gene expression analysis was used to characterize expression profiles of thymomas and thymic carcinomas, which were correlated with any clinical treatment and follow-up and pathology data that was available from the individuals. PAM showed that a set of nine biomarkers could be used to predict early stage disease (Stage I-II) with an error rate of about 10%. Similarly, a set of ten biomarkers could be used to predict absence of metastasis with an error rate of about 4%.

Based upon this work, compositions and methods are provided for detecting, diagnosing and prognosing an individual having or suspected of having cancer, particularly an individual having or suspected of having thymic cancer. Such compositions and methods can be used for the early diagnosis of or prognosticating recurrence or metastasis, for example, thymic cancer, which is essential to assure the best treatment regimen and outcome.

The Thymus and Thymic Cancers

The thymus is in the upper part of the mediastinum and plays a major role in developing cell-mediated immune responses. It reaches its maximum weight of about one ounce during puberty, and then slowly decreases in size during adulthood as it is gradually replaced by fat tissue. The thymus contains three types of cells, each of which can develop into distinct cancers. These cell types include: epithelial cells, lymphocytes and Kulchitsky cells. Thymic epithelial cells line the thymus and are the cells that constitute thymic cancers. If the lymphocytes become malignant (i.e., cancerous), they can develop into lymphomas (e.g., Hodgkin disease and non-Hodgkin lymphomas). If Kulchitsky cells become malignant, they can develop into carcinoid tumors of the thymus.

Thymomas and thymic carcinomas are cancers of the thymic epithelium or thymus gland/thymic tissue. They tend to be rare and tend to be asymptomatic until they become large enough to encroach on adjoining structures such as the trachea, lung, heart or great vessels. The involvement of these structures can be associated with significant worsening of prognosis, as it typically indicates that the tumors are unresectable.

Of particular interest herein are thymomas and thymic carcinomas, which are tumors that start from thymic epithelial cells. Thymomas and thymic carcinomas are the most common malignancies of the thymus gland with diverse histopathological findings and variable clinical outcomes. See, Masaoka et al. (1981) Cancer 48:2485-2492.

Diagnosing Thymic Cancers

Thymomas are low grade epithelial tumors of the thymus. Despite their indolent growth pattern, they may invade locally or metastasize. Tumors of the thymus typically present late in their clinical course as a mass lesion or due to associated paraneoplastic syndromes such as myasthenia gravis. Surgery is the mainstay of treatment with early-stage, localized tumors, whereas a combination strategy including surgery, radiation and chemotherapy is provided for advanced-stage disease.

The tumor cells in thymomas look similar to the normal cells of the thymus, grow slowly, and rarely spread beyond the thymus. They do, however, have a propensity to spread along the pleura, which can result in difficulty in predicting the preoperative stage of the cancer. The overall survival rate is about 60% at 5 years and under 50% at 10 years. Thymomas have been associated with paraneoplastic syndromes such as myasthenia gravis, polymyositis, lupus erythematosis, rheumatoid arthritis and pure red cell aplasia. See, Walid et al. (2008) South. Med. J. 101:764-766.

Conversely, the tumor cells in thymic carcinomas look quite different from the normal cells of the thymus, grow more quickly, and usually have spread to other parts of the body when the cancer is found. Thymic carcinomas are thus more difficult to treat than thymomas. Locally advanced thymic carcinomas often present as pleural plaques, which can be misdiagnosed as lung metastases on imaging studies. Thus, it becomes important to appropriately define metastases in tumors of thymic carcinomas. About 30% of individuals having a thymic carcinoma are asymptomatic when diagnosed.

Thymic cancers can be categorized (i.e., graded) as types A (includes medullary thymomas and spindle cell thymomas), AB (includes mixed thymomas), B1 (includes lymphocyte rich thymomas such as predominantly cortical thymomas, organoid thymomas, lymphocyte predominant thymomas and lymphocytic thymomas), B2 (includes cortical thymomas), B3 (includes epithelial predominant thymomas, squamoid thymomas and well differentiated thymic carcinomas) and thymic carcinomas under the 2004 World Health Organization ("WHO") classification of thymic epithelial tumors. See, Suster et al. (2006) J. Clin. Pathol. 125:542-554. Of these, types AB and B2 are the most common, type A is the least common, and thymic carcinoma is the most dangerous.

The WHO histological classification, however, has a limited role in determining prognosis. Current therapeutic management is almost entirely based on tumor stage.

Staging Thymic Cancers

Staging is the process of determining how far a cancer has spread. Treatment and prognosis therefore depend, to a large extent, on the cancer's stage.

The Masaoka Classification System is used most often to stage thymic cancer. See, Masaoka et al. (1981) Cancer 48:2485-2492. In the Masaoka Classification System, staging is based upon: (1) whether imaging tests, such as CT or MRI scans, can reveal the extent of disease; (2) whether the physician finds the tumor hard to separate from nearby tissues (indicating the tumor is invasive); and (3) whether the doctor sees tumor cells beyond the thymus when looking at the tumor sample under the microscope. The Masaoka Classification System thus separates thymic cancers into four main stages, as shown in Table 1.

TABLE 1

Masaoka Classification System

| Stage | Description |
|---|---|
| I | Intact thymic capsule; non-invasive |
| II | Capsular invasion into adjacent mediastinal fat or pleura |
| III | Macroscopic invasion into adjacent organs |
| IVa | Dissemination in thoracic cavity |
| IVb | Distant metastases |

Other staging systems are known in the art. See, e.g., Asamura et al. (2004) Interac. Cardiovasc. Thorac. Surg. 3:163-167; and Bedini et al. (2005) Ann. Thorac. Surg. 80:1994-2000.

Treatment Options for Thymic Cancers

Treatment options tend to vary depending upon the stage of the thymic cancer. Physicians often use a simpler system based on whether the cancers are likely to be resectable (where all visible tumor can be removed by surgery) or unresectable. In general, almost all stage I and II thymomas, most stage III thymomas, and even some stage IV thymomas are potentially resectable. Resectability is based on whether the tumor appears to have grown into nearby tissues or spread to distant sites, as well as on whether or not a person is healthy enough to have surgery.

Surgery is typically part of the treatment regimen whenever possible. Other forms of treatment include, but are not limited to, radiation therapy, chemotherapy or a combination thereof (i.e., chemo-radiation therapy).

Although complete resection and chemotherapy are effective therapies for most individuals with early disease, metastasis remains a major clinical problem for patients (10-year survival rate under 50%). See, Casey et al. (2008) Hematol. Oncol. Clin. North Am. 22:457-473. Unfortunately, there is a lack of information regarding the prediction of individuals at high risk of metastasis and the treatment regimen selection for such individuals. Depending on the extent of invasion of surrounding structures seen at surgery, adjuvant radiation therapy or chemotherapy may be given to these individuals. This therapeutic regimen can lead to undertreatment of individuals diagnosed at an early stage of disease, as well as overtreatment of indolent tumors diagnosed at a later stage. Currently, a significant number of individuals do not receive adjuvant chemo-radiation therapy until they develop recurrent or metastatic disease. There is a great need to better understand the complex pathology of thymic cancer and to develop specific molecular targets for therapy.

Compositions

Biomarkers

Compositions of the invention can include nucleic and amino acid biomarkers for diagnosing and evaluating the prognosis of an individual having or suspected of having cancer, particularly an individual having or suspected of having thymic cancer. As used herein, "biomarker" or "biomarkers" means nucleic acid (e.g., gene) or amino acid (e.g., protein) molecules whose level of expression in a cell, tissue, organ or mammal is altered compared to that of a normal or healthy cell, tissue, organ or mammal. The biomarkers described herein have expression levels that correlate with a cancer, particularly thymic cancer, and prognosis thereof.

The biomarkers can include polynucleotides comprising the entire or partial sequence of the nucleotide sequence encoding the biomarkers, or the complement of such sequences. As used herein, "polynucleotide" means a polymer of nucleic acids or nucleotides that, unless otherwise limited, encompasses naturally occurring bases (i.e., adenine, guanine, cytosine, thymine and uracil) or known base analogues having the essential nature of naturally occurring nucleotides in that they hybridize to single-stranded nucleic acid molecules in a manner similar to naturally occurring nucleotides. Although it may comprise any type of nucleotide units, the term generally applies to nucleic acid polymers of ribonucleotides ("RNA") or deoxyribonucleotides ("DNA"). The term includes single-stranded nucleic acid polymers, double-stranded nucleic acid polymers, and RNA and DNA made from nucleotide or nucleoside analogues that can be identified by their nucleic acid sequences, which are generally presented in the 5' to 3' direction (as the coding strand), where the 5' and 3' indicate the linkages formed between the 5' hydroxyl group of one nucleotide and the 3'-hydroxyl group of the next nucleotide. For a coding strand presented in the 5'-3' direction, its complement (or non-coding strand) is the strand that hybridizes to that sequence according to Watson-Crick base pairing. Thus, as used herein, the complement of a nucleic acid is the same as the "reverse complement" and describes the nucleic acid that in its natural form, would be based paired with the nucleic acid in question.

As used herein, a "nucleic acid," "nucleotide" or "nucleic acid residue" are used interchangeably to mean a nucleic acid that is incorporated into a molecule such as a gene or other polynucleotide. As noted above, the nucleic acid may be a naturally occurring nucleic acid and, unless otherwise limited, may encompass known analogues of natural nucleic acids that can function in a similar manner as naturally occurring nucleic acids. Examples of nucleic acids include any of the known base analogues of DNA and RNA such as, but not limited to, 4-acetylcytosine, 8-hydroxy-N-6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

As such, the biomarkers can include DNA or RNA comprising the entire or partial nucleotide sequence thereof.

Alternatively, the biomarkers can include a peptide, polypeptide or protein encoded by or corresponding to the nucleotide sequence of a biomarker described herein. When the biomarker is a peptide, polypeptide or protein, it can include the entire or partial amino acid sequence of any of the biomarker proteins or polypeptides.

As used herein, "amino acid" or "amino acid residue" are used interchangeably herein to mean an amino acid that is incorporated into an amino acid molecule such as a peptide, polypeptide or protein (collectively, "protein"). The amino acid may be a naturally occurring amino acid and, unless otherwise limited, may encompass known analogues of natural amino acids that can function in a similar manner as naturally occurring amino acids.

Whether polynucleotides or polypeptides, the biomarkers can include not only the entire biomarker sequence but also fragments and/or variants thereof. As used herein, "fragment" or "fragments" means a portion of the nucleic or amino acid sequence of the biomarker. Polynucleotides that are fragments of a biomarker nucleic acid sequence generally comprise at least about 10, 15, 20, 50, 75, 100, 150, 200, 250, 300, 350, 400, 450, 500, 550, 600, 650, 700, 800, 900, 1,000, 1,200 or 1,500 contiguous nucleotides, or up to the number of nucleotides present in a full-length biomarker polynucleotide disclosed herein. Likewise, a fragment of a biomarker polypeptide comprises at least about 15, 25, 30, 50, 100, 150, 200 or 250 contiguous amino acids, or up to the total number of amino acids present in a full-length biomarker protein.

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

As used herein, "variant" or "variants" means substantially similar sequences. Generally, variants of a particular biomarker have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity (preferably over the full length) to a biomarker as determined by sequence alignment programs.

One of skill in the art understands that variants can be constructed via modifications to either the polynucleotide or polypeptide sequence of the biomarker and can include substitutions, insertions (e.g., adding no more than ten nucleotides or amino acid) and deletions (e.g., deleting no more than ten nucleotides or amino acids). Methods of mutating and altering nucleic acid sequences, as well as DNA shuffling, are well known in the art. See, e.g., Crameri et al. (1997) *Nature Biotech.* 15:436-438; Crameri et al. (1998) *Nature* 391:288-291; Kunkel (1985) *Proc. Natl. Acad. Sci. USA* 82:488-492; Kunkel et al. (1987) *Methods in Enzymol.* 154:367-382; Moore et al. (1997) *J. Mol. Biol.* 272:336-347; Stemmer (1994) *Proc. Natl. Acad. Sci. USA* 91:10747-10751; Stemmer (1994) *Nature* 370:389-391; Zhang et al. (1997) *Proc. Natl. Acad. Sci. USA* 94:4504-4509; and *Techniques in Molecular Biology* (Walker & Gaastra eds., MacMillan Publishing Co. 1983) and the references cited therein; as well as U.S. Pat. Nos. 4,873,192; 5,605,793 and U.S. Pat. No. 5,837,458.

Methods of aligning sequences for comparison are well known in the art. Thus, the determination of percent sequence identity between any two sequences can be accomplished using a mathematical algorithm. Non-limiting examples of such mathematical algorithms are the algorithm of Myers & Miller (1988) *CABIOS* 4:11-17; the local alignment algorithm of Smith et al. (1981) *Adv. Appl. Math.* 2:482; the global alignment algorithm of Needleman & Wunsch (1970) *J. Mol. Biol.* 48:443-453; the search-for-local alignment method of Pearson & Lipman (1988) *Proc. Natl. Acad. Sci. USA* 85:2444-2448; the algorithm of Karlin & Altschul (1990) *Proc. Natl. Acad. Sci. USA* 87:2264, modified as in Karlin & Altschul (1993) *Proc. Natl. Acad. Sci. USA* 90:5873-5877.

Biomarkers for use in the compositions and methods described herein can include, but are not limited to, COL11A1 (collagen, type XI, alpha 1; GENBANK® Accession No. NM 001190709), DACT3 (dapper, antagonist of beta-catenin, homolog 3; GENBANK® Accession No. NM 145056), SLC9A2 (solute carrier family 9 (sodium/hydrogen exchanger) member 2; GENBANK® Accession No. NM_003048), PRRX1 (paired related homeobox 1; GENBANK® Accession No. NM_006902), PDGFRL (platelet-derived growth factor receptor-like; GENBANK® Accession No. NM_006207), SCUBE2 (signal peptide, CUB domain, EGF-like 2; GENBANK® Accession No. NM_001170690), MAB21L2 (mab-21-like 2; GENBANK® Accession Nos. NM_006439 and XM_938794), FCGBP (Fc fragment of IgG binding protein; GENBANK® Accession Nos. NM_003890 and XM 940656), MAOA (monoamine oxidase A; GENBANK® Accession Nos. NM_000240 and XM 499175), CTGF (connective tissue growth factor; GENBANK® Accession No. NM_001901), MET (met proto-oncogene (hepatocyte growth factor receptor); GENBANK® Accession No. NM_001127500), NEBL (nebulette; GENBANK® Accession No. NM_001173484), GPR98 (G protein-coupled receptor 98; GENBANK® Accession No. NM_032119), GLDN (gliomedin; GENBANK® Accession No. NM_181789), IGSF11 (immunoglobulin superfamily, member 11; GENBANK® Accession No. NM_152538), PCDH19 (protocadherin 19; GENBANK® Accession No. NM_001184880), C6orf118 (chromosome 6 open reading frame 118; GENBANK® Accession No. NM_144980), GOLSYN (syntabulin (syntaxin-interacting) (SYBU); GENBANK® Accession No. NM_001099755), BCMO1 (beta-carotene 15,15'-monooxygenase 1; GENBANK® Accession No. NG 012171), PTN (pleiotrophin; GENBANK® Accession No. NM_002825), LAMP2 (lysosomal-associated membrane protein 2; GENBANK® Accession No. NM_001122606), LRRC17 (leucine rich repeat containing 17; GENBANK® Accession No. NM_005824), DDX60 (DEAD (Asp-Glu-Ala-Asp) box polypeptide 60; GENBANK® Accession No. NM_017631), GEM (GTP binding protein overexpressed in skeletal muscle; GENBANK® Accession No. NM_181702), FRMD6 (FERM domain containing 6; GENBANK® Accession No. NM_152330), KGFLP1 (fibroblast growth factor 7 pseudogene; GENBANK® Accession Nos. NR 003674 and XM 942179), C9orf93 (chromosome 9 open reading frame 93; GENBANK® Accession No. NM_173550), NGB (neuroglobin; GENBANK® Accession Nos. NM_021257, XM_001129381 or XM_001132327), AKR1B10 (aldo-keto reductase family 1, member B1 (aldose reductase); GENBANK® Accession No. NM_001628), JPH1 (junctophilin 1; GENBANK® Accession No. NM_020647), STC1 (stanniocalcin 1; GENBANK® Accession No. NM_003155), STC2 (stanniocalcin 2; GENBANK® Accession No. NM_003714.2) and SLC7A11 (solute carrier family 7 (anionic amino acid transporter light chain, xc-system), member 11; GENBANK® Accession No. NM_014331).

Alternatively, the biomarkers for use in the compositions and methods described herein can include, but are not limited to, JPH1, ALDH1A3 (aldehyde dehydrogenase 1 family, member A3; GENBANK® Accession No. NM_000693), SPOCK1 (sparc/osteonectin, cwcv and kazal-like domains proteoglycan (testican) 1; GENBANK® Accession No. NM_004598), NGB, STC1, STC2, AKR1B10, ENPEP (glutamyl aminopeptidase (aminopeptidase A); GENBANK® Accession No. NM_001977), GOLSYN, RPL39 (ribosomal protein L39; GENBANK® Accession No. NM_001000), LAMP2, ABHD7 (epoxide hydrolase 4 (EPHX4); GENBANK® Accession No. NM_173567), RBPMS2 (RNA binding protein with multiple splicing 2; GENBANK® Accession Nos. NM_194272 and XM_496072), C9orf93, SESN3 (sestrin 3; GENBANK® Accession No. NM_144665), MRRF (mitochondrial ribosome recycling factor; GenBank® Accession No. NM_199177), NEBL, PRRX1, C14orf39 (chromosome 14 open reading frame 39; GENBANK® Accession No. NM_174978), LEPR (leptin receptor; GenBank® Accession No. NG 015831), DTNA (dystrobrevin, alpha; GENBANK® Accession No. NM_001198945), LCA5 (Leber congenital amaurosis 5; GENBANK® Accession No. NM_001122769), RSPO3 (R-spondin 3; NM_032784), IGF2BP2 (insulin-like growth factor 2 mRNA binding protein 2; GENBANK® Accession No. NM_006548), GPR98, TIAM2 (T-cell lymphoma invasion and metastasis 2; GENBANK® Accession No. NM_001010927), SLC9A2, MAB21L2, SCUBE2, DACT3, COL11A1 and SLC7A11.

Alternatively, the biomarkers for use in the compositions and methods described herein can include, but are not limited to, DACT3, JPH1, AKR1B10, COL11A1, SLC9A2, PDGFRL, FCGBP, PRRX1, SERPINF1, NGB, SCUBE2, MAB21L2, LEPR, LCA5, GPR98, RSPO3, STC1, STC2 and SLC7A11.

In some embodiments, biomarkers for use in the compositions and methods described herein can include, but are not limited to: 1) PDGFRL, FCGBP, PRRX1, SERPINF1, NGB, SCUBE2, MAB21L2, LEPR, LCA5, GPR98, RSPO3, STC1, STC2, SLC7A11, DACT3, JPH1, AKR1B10, COL11A1, and SLC9A2 or 2) PDGFRL, FCGBP, PRRX1, SERPINF1, NGB, DACT3, JPH1, AKR1B10, COL11A1, and SLC9A2 or 3) PDGFRL, FCGBP, PRRX1, NGB, DACT3, JPH1, AKR1B10, COL11A1, and SLC9A2 or 4) PDGFRL, FCGBP, PRRX1, NGB, DACT3, JPH1, AKR1B10, SERPINF1, and SLC9A2 or 5) AKR1B10, PDGFRL, FCGBP, COL11A1, SERPINF1, JPH1, SLC9A2, and DACT3.

Biomarkers for use as controls or references in the compositions and methods described herein include, but are not limited to, IPO8 (importin 8; GENBANK® Accession No. NM_001190995), TFRC (transferrin receptor (p90, CD71); GENBANK® Accession No. NM_001128148), UBC (ubiquitin C; GENBANK® Accession Nos. NM_021009, XM_942709, and XM_946288-XM_946327), PGE1 (PGE1 transporter; GENBANK® Accession No. AF187816) and GAPDH (glyceraldehyde-3-phosphate dehydrogenase; GENBANK® Accession No. NM_002046).

Kits

Compositions of the invention can include kits for detecting, diagnosing and prognosing an individual having or suspected of having cancer, particularly an individual having or suspected of having thymic cancer. As used herein, "kit" or "kits" means any manufacture (e.g., a package or a container) including at least one reagent, such as a nucleic acid probe, an antibody or the like, for specifically detecting the expression of the biomarkers described herein. In some embodiments, a plurality of reagents is used. As used herein, "plurality" means two or more probes and includes a combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or more or any range inclusive (e.g., 2-10 probes), wherein each probe of the combination selectively binds to a specifically intended target biomolecule.

As used herein, "probe" means any molecule that is capable of selectively binding to a specifically intended target biomolecule, for example, a nucleotide transcript or a protein encoded by or corresponding to a biomarker. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies and organic molecules.

In other embodiments, primer (e.g., oligonucleotide) sequences are useful for detecting or analyzing gene expression of biomarkers. In one embodiment, the present invention features an oligonucleotide or primer pairs selected from the group consisting of oligonucleotides shown in Table 10. In still another embodiment, the oligonucleotides of the invention are at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more identical to the nucleotide sequences set forth in oligonucleotides shown in Table 10. In yet another embodiment, the oligonucleotides of oligonucleotides shown in Table 10 are at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 52, 54, 56, 58, 60, 62, 64, 66, 68, 70, 72, 74, 76, 78, 80 or more nucleotides in length. A skilled artisan will appreciate that certain elements of the useful oligonucleotides described herein (e.g., restriction enzyme sites, cloning sites, overlapping linker sites, shortened, lengthened, and/or modified in sequence for suitable annealing temperature design, etc.) can readily be altered, as described further below, because they are not used to bind and amplify the biomarker gene sequences per se. It will be appreciated that the nucleic acid sequences of the present invention need not consist only of the sequence which is complementary to the targeted biomarker sequence. Thus, the nucleic acid sequences of the present invention can contain in addition, nucleotide sequences or other moieties which are suitable for the purposes for which the nucleic acid sequences are used. For example, use of the nucleic acid sequences as primers can be used for the amplification of Macaca mulatta immunoglobulin sequences via PCR, they can contain sequences which, when in duplex, form restriction enzyme sites which facilitate the cloning of the amplified sequences.

In one embodiment, the invention provides a combination of one or more oligonucleotides of the present invention (e.g., useful as probes). In yet another embodiment, the invention provides a set of oligonucleotides, also referred to herein as "primer pairs" and "nucleic acid primer sequences," selected from the group consisting of two or more of the oligonucleotides of the present invention. In still another embodiment, the invention provides oligonucleotides which are able to amplify a biomarker having a nucleotide sequence selected from the group consisting of oligonucleotides shown in Table 10, or a complement thereof.

In another embodiment, the oligonucleotides of the present invention comprise a label for detection. Such labels can be, e.g., radioactive labels which can be incorporated by known methods (e.g., nick translation or kinasing), radioactive isotopes, biotin, fluorescent groups, chemiluminescent groups (e.g., dioxetanes, particularly triggered dioxetanes), digoxigenin, enzymes, antibodies, luminescent agents, precipitating agents, dyes, combinations thereof, and the like.

In still another embodiment, the oligonucleotides of the present invention can comprise a promoter-primer, wherein a 5' portion of the sequence includes a promoter sequence.

In another aspect, oligonucleotide combinations of the present invention, for example, including at least one forward and one reverse primer, which together can be used for amplification and/or sequencing of an intended biomarker of the present invention, can be suitably packaged in a kit. In one embodiment, nested pairs of amplification and sequencing primers are provided. In still another embodiment, the kit comprises a set of primers selected from the group consisting of the oligonucleotides of the present invention. The primers in such kits can be labeled or unlabeled. The kit can also include additional reagents such as reagents for performing an amplification (e.g., PCR) reaction, a reverse transcriptase for conversion of RNA to cDNA for amplification, DNA polymerases, dNTP and ddNTP feedstocks. Kits of the present invention can also include instructions for use.

When making polynucleotides for use as probes to the biomarkers (e.g., hybridization probes or primer sets), one of skill in the art can be further guided by knowledge of redundancy in the genetic code as shown below in Table 2.

TABLE 2

Redundancy in Genetic Code.

| Residue | Triplet Codons Encoding the Residue |
| --- | --- |
| Ala (A) | GCU, GCC, GCA, GCG |
| Arg (R) | CGU, CGC, CGA, CGG, AGA, AGG |
| Asn (N) | AAU, AAC |
| Asp (D) | GAU, GAC |
| Cys (C) | UGU, UGC |
| Gln (Q) | CAA, CAG |
| Glu (E) | GAA, GAG |
| Gly (G) | GGU, GGC, GGA, GGG |
| His (H) | CAU, CAC |
| Ile (I) | AUU, AUC, AUA |
| Leu (L) | UUA, UUG, CUU, CUC, CUA, CUG |
| Lys (K) | AAA, AAG |
| Met (M) | AUG |
| Phe (F) | UUU, UUC |
| Pro (P) | CCU, CCC, CCA, CCG |
| Ser (S) | UCU, UCC, UCA, UCG, AGU, AGC |
| Thr (T) | ACU, ACC, ACA, ACG |
| Trp (W) | UGG |
| Tyr (Y) | UAU, UAC |
| Val (V) | GUU, GUC, GUA, GUG |
| START | AUG |
| STOP | UAG, UGA, UAA |

Methods of synthesizing polynucleotides are well known in the art, such as cloning and digestion of the appropriate sequences, as well as direct chemical synthesis (e.g., ink-jet deposition and electrochemical synthesis). Methods of cloning polynucleotides are described, for example, in Copeland et al. (2001) *Nat. Rev. Genet.* 2:769-779; *Current Protocols in Molecular Biology* (Ausubel et al. eds., John Wiley & Sons 1995); *Molecular Cloning: A Laboratory Manual, 3rd* ed. (Sambrook & Russell eds., Cold Spring Harbor Press 2001); and *PCR Cloning Protocols, 2nd* ed. (Chen & Janes eds., Humana Press 2002). Methods of direct chemical synthesis of polynucleotides include, but are not limited to, the phosphotriester methods of Reese (1978) *Tetrahedron* 34:3143-3179 and Narang et al. (1979) *Methods Enzymol.* 68:90-98; the phosphodiester method of Brown et al. (1979) *Methods Enzymol.* 68:109-151; the diethylphosphoramidate method of Beaucage et al. (1981) *Tetrahedron Lett.* 22:1859-1862; and the solid support methods of Fodor et al. (1991) *Science* 251:767-773; Pease et al. (1994) *Proc. Natl. Acad. Sci. USA* 91:5022-5026; and Singh-Gasson et al. (1999) *Nature Biotechnol.* 17:974-978; as well as U.S. Pat. No. 4,485,066. See also, Peattie (1979) *Proc. Natl. Acad. Sci. USA* 76:1760-1764; as well as EP Patent No. 1721908; Int'l Patent Application Publication Nos. WO 2004/022770 and WO 2005/082923; US Patent Application Publication Nos. 2009/0062521 and 2011/0092685; and U.S. Pat. Nos. 6,521,427; 6,818,395; 7,521,178 and U.S. Pat. No. 7,910,726.

When making antibodies for use as probes to the biomarkers, one of skill in the art can be further guided by knowledge that amino acids within the same conservative group typically can substitute for one another without substantially affecting the function of a peptide, polypeptide or protein (e.g., for use as an antigen or epitope). For the purpose of the present invention, such conservative groups are set forth in Table 3 and are based on shared properties. See also, Alberts et al., "Small molecules, energy, and biosynthesis," 56-57 In: *Molecular Biology of the Cell, 3rd* ed. (Garland Publishing Inc. 1994).

TABLE 3

Amino Acid Conservative Substitutions.

| Residue | Side Chain Polarity | Side Chain pH | Hydropathy Index | Preferred Conservative Substitution |
|---|---|---|---|---|
| Ala (A) | Non-polar | Neutral | 1.8 | Ser |
| Arg (R) | Polar | Basic (strongly) | −4.5 | Lys, Gln |
| Asn (N) | Polar | Neutral | −3.5 | Gln, His |
| Asp (D) | Polar | Acidic | −3.5 | Glu |
| Cys (C) | Non-polar | Neutral | 2.5 | Ser |
| Gln (Q) | Polar | Neutral | −3.5 | Asn, Lys |
| Glu (E) | Polar | Acidic | −3.5 | Asp |
| Gly (G) | Non-polar | Neutral | −0.4 | Pro |
| His (H) | Polar | Basic (weakly) | −3.2 | Asn, Gln |
| Ile (I) | Non-polar | Neutral | 4.5 | Leu, Val |
| Leu (L) | Non-polar | Neutral | 3.8 | Ile, Val |
| Lys (K) | Polar | Basic | −3.9 | Arg, Gln |
| Met (M) | Non-polar | Neutral | 1.9 | Leu, Ile |
| Phe (F) | Non-polar | Neutral | 2.8 | Met, Leu, Tyr |
| Pro (P) | Non-polar | Neutral | −1.6 | Gly |
| Ser (S) | Polar | Neutral | −0.8 | Thr |
| Thr (T) | Polar | Neutral | −0.7 | Ser |
| Trp (W) | Non-polar | Neutral | −0.9 | Tyr |
| Tyr (Y) | Polar | Neutral | −1.3 | Trp, Phe |
| Val (V) | Non-polar | Neutral | 4.2 | Ile, Leu |

The following six groups each contain amino acids that are typical but not necessarily exclusive conservative substitutions for one another: 1. Alanine (A), Serine (S), Threonine (T); 2. Aspartic acid (D), Glutamic acid (E); 3. Asparagine (N), Glutamine (Q); 4. Arginine (R), Lysine (K); 5. Isoleucine (I), Leucine (L), Methionine (M), Valine (V); and 6. Phenylalanine (F), Tyrosine (Y), Tryptophan (W).

Substantial changes in function can be made by selecting substitutions that are less conservative than those listed in the table above, i.e., by selecting residues that differ more significantly in their effect on maintaining (a) the structure of the polypeptide backbone in the area of substitution, (b) the charge or hydrophobicity of the polypeptide at the target site, or (c) the bulk of a side chain. The substitutions that in general can be expected to produce the greatest changes in the polypeptide's properties will be those in which (a) a hydrophilic residue, e.g., seryl or threonyl, is substituted by a hydrophobic residue, e.g., leucyl, isoleucyl, phenylalanyl, valyl or alanyl; (b) a cysteine or proline is substituted by any other residue; (c) a residue having an electropositive side chain, e.g., lysyl, arginyl or histidyl, is substituted by an electronegative side chain, e.g., glutamyl or aspartyl; (d) a residue having a bulky side chain, e.g., phenylalanyl, is substituted by a residue not having a side chain, e.g., glycyl; or (e) by increasing the number of sulfation or glycosylation.

Methods of synthesizing polypeptides or producing them recombinantly are well known in the art. See, e.g., Ausubel et al. (1995), supra; and *Proteins: Structures and Molecular Principles* (Creighton ed., W. H. Freeman & Co. 1983). Short peptides, for example, can be synthesized on a solid support or in solution. Longer peptides may be made using recombinant DNA techniques. Here, polynucleotides encoding the peptides of the invention may be synthesized, and/or cloned, and expressed according to methods well known in the art and used in the production of, for example, antibodies for use in the kits described below to detect the biomarkers. See, e.g., Sambrook & Russell (2001), supra.

Methods of making antibodies are well known in the art. As used herein, "antibody" or "antibodies" includes an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). For example, the term includes bivalent or bispecific molecules, diabodies, triabodies and tetrabodies. Bivalent and bispecific molecules are described in, e.g., Kostelny et al. (1992) *J. Immunol.* 148:1547; Pack & Pluckthun (1992) *Biochem.* 31:157; Zhu et al. (1997) *Protein Sci.* 6:781; Hu et al. (1996) *Cancer Res.* 56:3055; Adams et al. (1993) *Cancer Res.* 53:4026; and McCartney et al. (1995) *Protein Eng.* 8:301. The term "antibody" also includes antigen binding forms of antibodies, including fragments with antigen-binding capability (e.g., Fab', F(ab')$_2$, Fab, Fv and rIgG). The term also refers to recombinant single chain Fv fragments (scFv). Preferably, antibodies employed to practice the present invention bind to its target protein with an affinity (association constant) of equal to or greater than $10^7$ M$^{-1}$.

An antibody can be a monoclonal and polyclonal antibody and can belong to any antibody class (i.e., IgG, IgM, IgA, etc.). One of skill in the art is familiar with methods for making monoclonal antibodies (Mab). For example, one of skill in the art can make monoclonal antibodies by isolating lymphocytes and fusing them with myeloma cells, thereby producing hybridomas. See, e.g., *Cell Biology: A Laboratory Handbook*, 3rd ed. (Celis, ed., Elsevier Academic Press 2006); Milstein, "Handbook of experimental immunology," (Blackwell Scientific Pub. 1986); and Goding J, "Monoclonal antibodies: principles and practice," (Academic Press 1983). The cloned hybridomas are then screened for production of, e.g., "anti-biomarker" (i.e., antibodies that bind preferentially to one of the biomarkers described herein, as well as fragments or variants thereof). Monoclonal antibodies are thus not limited by the manner in which the antibodies are produced, whether such production is in situ or not. Alternatively, antibodies can be produced by recombinant DNA technology including, but not limited, to expression in bacteria, yeast, insect cell lines or mammalian cell lines.

Likewise, methods of making polyclonal antibodies are well known in the art. For example, one of skill in the art can make polyclonal antibodies by immunizing a suitable host animal, for example, such as a rabbit, with an immunogen (e.g., biomarker) and using properly diluted serum or isolating immunoglobulins from the serum. The animal may therefore be inoculated with the immunogen, with blood subsequently being removed from the animal and an IgG fraction purified. Other suitable host animals include a chicken, goat, sheep, guinea pig, rat or mouse. If desired, the immunogen may be administered as a conjugate in which the immunogen is coupled, for example, via a side chain of one of its amino acid residues, to a suitable carrier. The carrier molecule is typically a physiologically acceptable carrier. The antibody obtained may be purified to a purity of up to about 70%, up to about 80%, up to about 90%, up to about 95%, up to about 99% or up to about 100%.

Antibody also encompasses functional fragments, like Fab and $F(ab')_2$ antibodies. Treatment of antibodies with proteolytic enzymes, such as papain and pepsin, generates these antibody fragments, especially anti-biomarker fragments.

Antibodies can be conjugated to a detectable label for easy visualization. Examples of suitable labels for the compositions and methods described herein include, but are not limited to, radiolabels, biotin (which may be detected by avidin or streptavidin conjugated to peroxidase), lanthanides, alkaline phosphatase and fluorescent labels (e.g., fluorescein, rhodamine, especially the ALEXA FLUOR® family of fluorescent dyes available from Invitrogen/Molecular Probes). Labeling of the antibody can be carried out by, for example, labeling free amine groups (covalently or non-covalently). Some labels can be detected by using a labeled counter suitable for the detection of the label in question.

The kits can be promoted, distributed or sold as units for performing the methods described below. Additionally, the kits can contain a package insert describing the kit and methods for its use. For example, the insert can include instructions for correlating the level of biomarker expression measured with a subject's likelihood of having developed thymic cancer or the likely prognosis of a subject already diagnosed with thymic cancer.

The kits therefore can be for detecting, diagnosing and prognosing a thymic cancer with biomarkers at the nucleic acid level. Such kits are compatible with both manual and automated nucleic acid detection techniques (e.g., gene arrays, Northern blotting or Southern blotting). These kits can include a plurality of probes, for example, from two to thirty nucleic acid probes that specifically bind to distinct biomarkers, fragments or variants thereof. Alternatively, the kits can contain at least two probes, at least three probes, at least four probes, at least five probes, at least six probes, at least seven probes, at least eight probes, at least nine probes, at least ten probes, at least eleven probes, at least twelve probes, at least thirteen probes, at least fourteen probes, at least fifteen probes, at least sixteen probes, at least seventeen probes, at least eighteen probes, at least nineteen probes, at least twenty probes, at least twenty-five probes, or at least thirty probes.

Likewise, the kits can be for detecting, diagnosing and prognosing a thymic cancer with biomarkers at the amino acid level. Such kits are compatible with both manual and automated immunohistochemistry techniques (e.g., cell staining, ELISA or Western blotting). These kits can include a plurality of probes, for example, from two to thirty antibodies that specifically bind to distinct biomarkers, fragments or variants thereof. Alternatively, the kits can contain at least two antibodies, at least three antibodies, at least four antibodies, at least five antibodies, at least six antibodies, at least seven antibodies, at least eight antibodies, at least nine antibodies, at least ten antibodies, at least eleven antibodies, at least twelve antibodies, at least thirteen antibodies, at least fourteen antibodies, at least fifteen antibodies, at least sixteen antibodies, at least seventeen antibodies, at least eighteen antibodies, at least nineteen antibodies, at least twenty antibodies, at least twenty-five antibodies or at least thirty antibodies. Each antibody can be provided in the kit as an individual reagent or, alternatively, as an antibody cocktail comprising the selected number of antibodies directed to different biomarkers.

Any or all of the kit reagents can be provided within containers that protect them from the external environment, such as in sealed containers. Positive and/or negative controls can be included in the kits to validate the activity and correct usage of reagents employed in accordance with the invention. Controls can include samples, such as tissue sections, cells fixed on glass slides, RNA preparations from tissues or cell lines, and the like, known to be either positive or negative for the presence of at least five different biomarkers. The design and use of controls is standard and well within the routine capabilities of one of skill in the art.

Methods

Methods of Detecting and/or Diagnosing Thymic Cancers

Methods of the invention include detecting and/or diagnosing a thymic cancer in an individual having or suspected of having a thymic cancer. The method can include determining the expression levels of RNA transcripts or expression products thereof of at pre-selected number of biomarkers in a sample from an individual having or suspected of having a cancer such as a thymic cancer.

The methods generally begin by collecting a sample from an individual having or suspected of having a cancer. As used herein, "sample" means any collection of cells, tissues, organs or bodily fluids in which expression of a biomarker can be detected. Examples of such samples include, but are not limited to, biopsy specimens of cells, tissues or organs, bodily fluids and smears.

When the sample is a biopsy specimen, it can include, but is not limited to, thymic cells, particularly thymus tissue from a biopsy, such as a thymic tumor tissue sample. Biopsy specimens can be obtained by a variety of techniques including, but not limited to, scraping or swabbing an area, using a needle to aspirate cells or bodily fluids, or removing a tissue sample. Methods for collecting various body samples/biopsy specimens are well known in the art. In some embodiments, a thymus tissue sample is obtained by, for example, fine needle aspiration biopsy, core needle biopsy, or excisional biopsy.

Fixative and staining solutions can be applied to, for example, cells or tissues for preserving them and for facilitating examination. Body samples, particularly thymus tissue samples, can be transferred to a glass slide for viewing under magnification. In one embodiment, the body sample is a formalin-fixed, paraffin-embedded thymic tissue sample, particularly a primary thymic tumor sample.

When the sample is a bodily fluid, it can include, but is not limited to, blood, lymph, urine, saliva, aspirates or any other bodily secretion or derivative thereof. When the sample is blood, it can include whole blood, plasma, serum or any derivative of blood.

After collecting and preparing the specimen from the individual having or suspected of having thymic cancer, the methods then include detecting expression of the biomarkers. One can use any method available for detecting expression of polynucleotide and polypeptide biomarkers. As used herein, "detecting expression" means determining the quantity or presence of a biomarker polynucleotide or its expression product. As such, detecting expression encompasses instances where a biomarker is determined not to be expressed, not to be detectably expressed, expressed at a low level, expressed at a normal level, or overexpressed.

Expression of a biomarker can be determined by normalizing the level of a reference marker/control, which can be all measured transcripts (or their products) in the sample or a particular reference set of RNA transcripts (or their products). Normalization can be performed to correct for or normalize away both differences in the amount of biomarker assayed and variability in the quality of the biomarker type used. Therefore, an assay typically measures and incorporates the expression of certain normalizing polynucleotides or polypeptides, including well known housekeeping genes, such as, for example, GAPDH and/or actin. Alternatively, normalization can be based on the mean or median signal of all of the assayed biomarkers or a large subset thereof (global normalization approach).

To determine overexpression, the sample can be compared with a corresponding sample that originates from a healthy individual. That is, the "normal" level of expression is the level of expression of the biomarker in, for example, a thymus tissue sample from an individual not afflicted with thymic cancer. Such a sample can be present in standardized form. Sometimes, determining biomarker overexpression requires no comparison between the sample and a corresponding sample that originated from a healthy individual. For example, detecting overexpression of a biomarker indicative of a poor prognosis in a thymic tumor sample may preclude the need for comparison to a corresponding thymus tissue sample that originates from a healthy individual. Moreover, no expression, underexpression or normal expression (i.e., the absence of overexpression) of a biomarker or combination of biomarkers of interest provides useful information regarding the prognosis of a thymic cancer patient.

Methods of detecting and quantifying polynucleotide biomarkers in a sample are well known in the art. Such methods include, but are not limited to gene expression profiling, which are based on hybridization analysis of polynucleotides, and sequencing of polynucleotides. The most commonly used methods art for detecting and quantifying polynucleotide expression in include northern blotting and in situ hybridization (Parker & Barnes (1999) *Methods Mol. Biol.* 106:247-283), RNAse protection assays (Hod (1992) *Biotechniques* 13:852-854), PCR-based methods, such as RT-PCR (Weis et al. (1992) *TIG* 8:263-264), and array-based methods (Schena et al. (1995) *Science* 270:467-470). Alternatively, antibodies may be employed that can recognize specific duplexes, including DNA duplexes, RNA duplexes, and DNA-RNA hybrid duplexes, or DNA-protein duplexes in, for example, an oligonucleotide-linked immunosorbent assay ("OLISA"). See, Lee et al. (1985) *FEBS Lett.* 190: 120-124; Han et al. (2010) *Bioconjug. Chem.* 21:2190-2196; Miura et al. (1987) *Biochem. Biophys. Res. Commun.* 144: 930-935; and Tanha & Lee (1997) *Nucleic Acids Res.* 25:1442-1449. Representative methods for sequencing-based gene expression analysis include Serial Analysis of Gene Expression ("SAGE") and gene expression analysis by massively parallel signature sequencing. See, Velculescu et al. (1995) *Science* 270: 484-487.

Isolated RNA can be used to determine the level of biomarker transcripts (i.e., mRNA) in a sample, as many expression detection methods use isolated RNA. The starting material typically is total RNA isolated from a body sample, such as a tumor or tumor cell line, and corresponding normal tissue or cell line, respectively. Thus, RNA can be isolated from a variety of primary tumors, including breast, lung, colon, prostate, brain, liver, kidney, pancreas, spleen, thymus, testis, ovary, uterus, and the like, or tumor cell lines. If the source of mRNA is a primary tumor, mRNA can be extracted, for example, from frozen or archived paraffin-embedded and fixed (e.g., formalin-fixed) tissue samples.

Methods of isolating polynucleotides such as RNA from a sample are well known in the art. See, e.g., *Molecular Cloning: A Laboratory Manual*, $3^{rd}$ ed. (Sambrook et al. eds., Cold Spring Harbor Press 2001); and *Current Protocols in Molecular Biology* (Ausubel et al. eds., John Wiley & Sons 1995). Methods for RNA extraction from paraffin-embedded tissues also are well known in the art. See, e.g., Rupp & Locker (1987) *Lab Invest.* 56:A67; and De Andres et al. (1995) *Biotechniques* 18:42-44. Moreover, isolation/purification kits are commercially available for isolating polynucleotides such as RNA (Qiagen; Valencia, Calif.). For example, total RNA from cells in culture can be isolated using QIAGEN RNEASY® Mini-Columns. Other commercially available RNA isolation/purification kits include MASTERPURE™ Complete DNA and RNA Purification Kit (Epicentre; Madison, Wis.) and Paraffin Block RNA Isolation Kit (Ambion; Austin, Tex.). Total RNA from tissue samples can be isolated, for example, using RNA Stat-60 (Tel-Test; Friendswood, Tex.). RNA prepared from a tumor can be isolated, for example, by cesium chloride density gradient centrifugation. Additionally, large numbers of tissue samples readily can be processed using techniques well known to those of skill in the art, such as, for example, the single-step RNA isolation process of Chomczynski (U.S. Pat. No. 4,843,155).

Once isolated, the polynucleotide, such as mRNA, can be used in hybridization or amplification assays including, but not limited to, Southern or Northern blotting, PCR and probe arrays. One method of detecting polynucleotide levels involves contacting the isolated polynucleotides with a nucleic acid molecule (probe) that can hybridize to the desired polynucleotide target. The nucleic acid probe can be, for example, a full-length DNA, or a portion thereof, such as an oligonucleotide of at least about 10, 15, 20, 30, 40, 50, 75, 100, 125, 150, 175, 200, 225, 250, 275, 300, 400 or 500 nucleotides or more in length and sufficient to specifically hybridize under stringent conditions to a polynucleotide such as an mRNA or genomic DNA encoding a biomarker of interest. Hybridization of a polynucleotide encoding the biomarker of interest with the probe indicates that the biomarker in question is being expressed.

Stringent hybridization conditions are defined as hybridizing at 68° C. in 5×SSC/5×Denhardt's solution/1.0% SDS, and washing in 0.2×SSC/0.1% SDS+/−100 µg/ml denatured salmon sperm DNA at room temperature (RT), and moderately stringent hybridization conditions are defined as washing in the same buffer at 42° C. Additional guidance regarding such conditions is readily available in the art, for example, in *Molecular Cloning: A Laboratory Manual*, $3^{rd}$ ed. (Sambrook et al. eds., Cold Spring Harbor Press 2001); and *Current Protocols in Molecular Biology* (Ausubel et al. eds., John Wiley & Sons 1995).

Another method of detecting polynucleotide expression levels involves immobilized polynucleotides on a solid surface and contacting the immobilized polynucleotides with a probe, for example by running isolated mRNA on an agarose gel and transferring the mRNA from the gel to a membrane, such as nitrocellulose. Alternatively, the probes can be immobilized on a solid surface and isolated mRNA is contacted with the probes, for example, in an Agilent Gene Chip Array.

For example, microarrays can be used to detect polynucleotide expression. Microarrays are particularly well suited because of the reproducibility between different experiments. DNA microarrays provide one method for the simultaneous measurement of the expression levels of large numbers of polynucleotides. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, e.g., U.S. Pat. Nos. 6,040,138; 5,800,992; 6,020,135; 6,033,860 and U.S. Pat. No. 6,344,316. High-density oligonucleotide arrays are particularly useful for determining expression profiles for a large number of polynucleotides in a sample.

Methods of synthesizing these arrays using mechanical synthesis methods are described in, for example, U.S. Pat. No. 5,384,261. Although a planar array surface generally is used, the array can be fabricated on a surface of virtually any shape or even a multiplicity of surfaces. Arrays can be nucleic acids (or peptides) on beads, gels, polymeric surfaces, fibers (such as fiber optics), glass or any other appropriate substrate. See, e.g., U.S. Pat. Nos. 5,770,358; 5,789,162; 5,708,153; 6,040,193 and U.S. Pat. No. 5,800,992.

As such, PCR-amplified inserts of cDNA clones can be applied to a substrate in a dense array. For example, at least about 10,000 nucleotide sequences can be applied to the substrate. The microarrayed genes, immobilized on the microchip at 10,000 elements each, are suitable for hybridization under stringent conditions. Fluorescently labeled cDNA probes can be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance.

With dual color fluorescence, separately labeled cDNA probes generated from two sources of polynucleotide can be hybridized pairwise to the array. The relative abundance of the transcripts from the two sources corresponding to each specified molecule is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels. See, Schena et al. (1996) *Proc. Natl. Acad. Sci. USA* 93:106-149. Advantageously, microarray analysis can be performed by commercially available equipment, following manufacturer's protocols, such as by using the AFFYMETRIX® GenChip Technology, or AGILENT® Ink-Jet Microarray Technology. The development of microarray methods for large-scale analysis of gene expression makes it possible to search systematically for molecular markers of cancer classification and outcome prediction in a variety of tumor types.

Another method of detecting polynucleotide expression levels involves a digital technology developed by NANOSTRING® Technologies (Seattle, Wash.) and based on direct multiplexed measurement of gene expression, which offers high levels of precision and sensitivity (<1 copy per cell). The method uses molecular "barcodes" and single molecule imaging to detect and count hundreds of unique transcripts in a single reaction. Each color-coded barcode is attached to a single target-specific probe corresponding to a gene of interest. Mixed together with controls, they form a multiplexed CodeSet. Two 50 base probes per mRNA can be included for hybridization. The reporter probe carries the signal, and the capture probe allows the complex to be immobilized for data collection. After hybridization, the excess probes are removed and the probe/target complexes aligned and immobilized in an NCOUNTER® Cartridge. Sample cartridges are placed in a digital analyzer for data collection. Color codes on the surface of the cartridge are counted and tabulated for each target molecule.

Another method of detecting polynucleotide expression levels involves nucleic acid amplification, for example, by RT-PCR (U.S. Pat. No. 4,683,202), ligase chain reaction (Barany (1991) *Proc. Natl. Acad. Sci. USA* 88:189-193), self-sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al., (1988) *Bio/Technology* 6:1197), rolling circle replication (U.S. Pat. No. 5,854,033), or any other nucleic acid amplification method, followed by the detection of the amplified molecules using techniques well known in the art. Likewise, biomarker expression can be assessed by quantitative fluorogenic RT-PCR (i.e., the TAQMAN® System). For PCR analysis, methods and software are available to determine primer sequences for use in the analysis. These methods are particularly useful for detecting polynucleotides present in very low numbers.

Additional methods of detecting polynucleotide expression levels of RNA may be monitored using a membrane blot (such as used in hybridization analysis such as Northern or Southern blotting, dot, and the like), or microwells, sample tubes, gels, beads or fibers (or any solid support comprising bound nucleic acids). See, e.g., U.S. Pat. Nos. 5,770,722; 5,874,219; 5,744,305; 5,677,195 and U.S. Pat. No. 5,445,934. Polynucleotide biomarker expression also can include using nucleic acid probes in solution.

Another method of detecting polynucleotide expression levels involves SAGE, which is a method that allows the simultaneous and quantitative analysis of a large number of polynucleotides without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules that can be sequenced, revealing the identity of the multiple tags simultaneously. The expression pattern of any population of transcripts can be quantitatively evaluated by determining the abundance of individual tags and identifying the gene corresponding to each tag. See, Velculescu et al. (1995), supra.

Another method of detecting polynucleotide expression levels involves massively parallel signature sequencing ("MPSS"). See, Brenner et al. (2000) *Nat. Biotech.* 18:630-634. This sequencing combines non-gel-based signature sequencing with in vitro cloning of millions of templates on separate diameter microbeads. First, a microbead library of DNA templates can be constructed by in vitro cloning. This is followed by assembling a planar array of the template-containing microbeads in a flow cell at a high density (typically greater than $3.0 \times 10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast DNA library.

Likewise, methods of detecting and quantifying polypeptides in a sample are well known in the art and include, but are not limited to, immunohistochemistry and proteomics-based methods.

For example, a thymic tissue sample can be collected by, for example, biopsy techniques known in the art. Samples can be frozen for later preparation or immediately placed in a fixative solution. Tissue samples can be fixed by treatment with a reagent, such as formalin, gluteraldehyde, methanol, or the like and embedded in paraffin. Methods for preparing slides for immunohistochemical analysis from formalin-fixed, paraffin-embedded tissue samples are well known in the art.

Some samples may need to be subjected to antigen retrieval or antigen unmasking to make the biomarker polypeptides accessible to, for example, antibody binding. As used herein, "antigen retrieval" or "antigen unmasking" means methods for increasing antigen accessibility or recovering antigenicity in, for example, formalin-fixed, paraffin-embedded tissue samples. Formalin fixation of tissue samples results in extensive cross-linking of proteins that can lead to the masking or destruction of antigen sites and, subsequently, poor antibody staining. Any method of making antigens more accessible for antibody binding may be used in the practice of the invention, including those antigen retrieval methods known in the art. See, e.g., *Tumor Marker Protocols* (Hanausek & Walaszek, eds., Humana Press, Inc. 1988); and Shi et al., *Antigen Retrieval Techniques: Immunohistochemistry and Molecular Morphology* (Eaton Publishing 2000).

Methods of antigen retrieval are well known in the art. Examples of such methods include, but are not limited to, treatment with proteolytic enzymes (e.g., trypsin, chymotrypsin, pepsin, pronase and the like) or antigen retrieval solutions. Antigen retrieval solutions can include citrate buffer, pH 6.0, Tris buffer, pH 9.5, EDTA, pH 8.0, L.A.B. ("Liberate Antibody Binding Solution"; Polysciences; Warrington, Pa.), antigen retrieval Glyca solution (Biogenex; San Ramon, Calif.), citrate buffer solution, pH 4.0, DAWN® detergent (Proctor & Gamble; Cincinnati, Ohio), deionized water and 2% glacial acetic acid. Such an antigen retrieval solutions can be applied to a formalin-fixed tissue sample and then heated in an oven (e.g., at 60° C.), steamed (e.g., at 95° C.) or pressure cooked (e.g., at 120° C.) for a pre-determined time periods. Alternatively, antigen retrieval can be performed at room temperature. As such, incubation times will vary with the particular antigen retrieval solution selected and with the incubation temperature. For example, an antigen retrieval solution can be applied to a sample for as little as about 5, 10, 20 or 30 minutes or up to overnight. The design of assays to determine the appropriate antigen retrieval solution and optimal incubation times and temperatures is standard and well within the routine capabilities of one of skill in the art.

Following antigen retrieval, samples are blocked using an appropriate blocking agent (e.g., hydrogen peroxide). An antibody directed to a biomarker of interest then is incubated with the sample for a time sufficient to permit antigen-antibody binding. As described elsewhere, at least five antibodies directed to five distinct biomarkers can be used to detect thymic cancer. Where more than one antibody may be used, these antibodies can be added to a single sample sequentially as individual antibody reagents, or simultaneously as an antibody cocktail. Alternatively, each individual antibody can be added to a separate tissue section from a single patient sample, and the resulting data pooled.

Methods of detecting antibody binding are well known in the art. Antibody binding to a biomarker of interest can be detected through the use of chemical reagents that generate a detectable signal that corresponds to the level of antibody binding, and, accordingly, to the level of biomarker protein expression. For example, antibody binding can be detected through the use of a secondary antibody that is conjugated to a labeled polymer. Examples of labeled polymers include but are not limited to polymer-enzyme conjugates. The enzymes in these complexes are typically used to catalyze the deposition of a chromogen at the antigen-antibody binding site, thereby resulting in cell or tissue staining that corresponds to expression level of the biomarker of interest. Enzymes of particular interest include horseradish peroxidase (HRP) and alkaline phosphatase (AP). Commercially antibody detection systems include, for example, the Dako Envision+system (Glostrup; Denmark) and Biocare Medical's Mach 3 System (Concord, Calif.), and can be used herein.

Detecting antibody binding can be facilitated by coupling the antibody to a detectable moiety. Examples of detectable moieties include various enzymes, prosthetic groups, fluorescent materials, luminescent materials, bioluminescent materials, and radioactive materials. Examples of suitable enzymes include horseradish peroxidase, alkaline phosphatase, galactosidase and acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriaziny-lamine fluorescein, dansyl chloride and phycoerythrin. An example of a luminescent material is luminol. Examples of bioluminescent materials include luciferase, luciferin and aequorin. Examples of radioactive materials include $^{125}$I, $^{131}$I, $^{35}$S and $^{3}$H.

In regard to additional antibody detection methods, there also exists video microscopy and software methods for quantitatively determining an amount of multiple molecular species (e.g., biomarker proteins) in a biological sample, where each molecular species present is indicated by a representative dye marker having a specific color. Such methods are known in the art as a colorimetric analysis method. In these methods, video-microscopy is used to provide an image of the biological sample after it has been stained to visually indicate the presence of a particular biomarker of interest. See, e.g., U.S. Pat. No. 7,065,236 and U.S. Pat. No. 7,133,547, which disclose the use of an imaging system and associated software to determine the relative amounts of each molecular species present based on the presence of representative color dye markers as indicated by those color dye markers' optical density or transmittance value, respectively, as determined by an imaging system and associated software. These methods provide quantitative determinations of the relative amounts of each molecular species in a stained biological sample using a single video image that is "deconstructed" into its component color parts.

As noted above, polynucleotide and polypeptide biomarkers for use in detecting and/or diagnosing thymic cancer can include JPH1, ALDH1A3, SPOCK1, NGB, STC1, STC 2, AKR1B10, ENPEP, GOLSYN, RPL39, LAMP2, ABHD7, RBPMS2, C9orf93, SESN3, MRRF, NEBL, PRRX1, C14orf39, LEPR, DTNA, LCA5, RSPO3, IGF2BP2, GPR98, TIAM2, SLC9A2, MAB21L2, SCUBE2, DACT3, COL11A1 and SLC7A11.

Alternatively, polynucleotide and polypeptide biomarkers for use herein can include DACT3, JPH1, AKR1B10, COL11A1, SLC9A2, PDGFRL, FCGBP, PRRX1, SERPINF1, NGB, SCUBE2, MAB21L2, LEPR, LCA5, GPR98, RSPO3, STC1, STC2 and SLC7A11.

Alternatively, polynucleotide and polypeptide biomarkers for use herein can include DACT3, JPH1, COL11A1, SCUBE2, MAB21L2, LEPR, LCA5, GPR98, RSPO3, STC1, STC2 and SLC7A11.

Alternatively, polynucleotide and polypeptide biomarkers for use herein can include DACT3, JPH1, COL11A1, SCUBE2, MAB21L2, LEPR, LCA5, GPR98 and RSPO3.

Additional polynucleotide and polypeptide biomarkers for use herein are described above in the section defining biomarkers of the present invention.

Polynucleotide and polypeptide biomarkers for use herein as controls or references can include IPO8, TFRC, UBC, PGE1 and GAPDH.

With respect to detecting and diagnosing thymic cancer, preferred biomarkers can be DACT3, JPH1, COL11A1, SCUBE2, MAB21L2, LEPR, LCA5, GPR98, RSPO3, STC1, STC2 and SLC7A11, where overexpression of DACT3, COL11A1, SCUBE2, MAB21L2, LEPR, LCA5, GPR98 and RSPO3, in connection with reduced expression of STC1, STC2, JPH1 and SLC7A11, indicates early stage thymic cancer.

Methods of Prognosing Thymic Cancers

Methods of the invention include prognosing the likelihood of metastasis in an individual having a thymic cancer. The methods include detecting the expression of biomarkers in a sample from an individual having a thymic cancer. Altered expression levels of a biomarker or combination of biomarkers can be used to indicate thymic cancer prognosis (i.e., poor or good prognosis). As such, altered expression of a particular biomarker or combination of biomarkers permits the differentiation of individuals having a thymic cancer that are likely to experience disease recurrence and/or metastasis (i.e., poor prognosis) from those who are more likely to remain cancer free (i.e., good prognosis).

As used herein, "prognose," "prognoses," "prognosis" and "prognosing" means predictions about or predicting a likely course or outcome of a disease or disease progression, particularly with respect to a likelihood of, for example, disease remission, disease relapse, tumor recurrence, metastasis and death (i.e., the outlook for chances of survival). As used herein, "good prognosis" or "favorable prognosis" means a likelihood that an individual having cancer, particularly thymic cancer, will remain disease-free (i.e., cancer-free). As used herein, "poor prognosis" means a likelihood of a relapse or recurrence of the underlying cancer or tumor, metastasis or death. Individuals classified as having a good prognosis remain free of the underlying cancer or tumor. Conversely, individuals classified as having a bad prognosis experience disease relapse, tumor recurrence, metastasis or death.

Additional criteria for evaluating the response to antithymic cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

One of skill in the art is familiar with the time frame(s) for assessing prognosis and outcome. Examples of such time frames include, but are not limited to, less than one year, about one, two, three, four, five, six, seven, eight, nine, ten, fifteen, twenty or more years. With respect to thymic cancer, the relevant time for assessing prognosis or disease-free survival time often begins with the surgical removal of the tumor or suppression, mitigation or inhibition of tumor growth. Thus, for example, a good prognosis can be a likelihood that the individual having thymic cancer will remain free of the underlying cancer or tumor for a period of at least about five, more particularly, a period of at least about ten years. In contrast, for example, a bad prognosis can be a likelihood that the individual having thymic cancer experiences disease relapse, tumor recurrence, metastasis or death within a period of less than about five years, more particularly a period of less than about ten years.

Methods of prognosing cancer are well known in the art. One method to evaluate the prognostic performance of the biomarkers and/or other clinical parameters utilizes PAM. PAM is a statistical technique for class prediction from gene expression data using nearest shrunken centroids. See, Tibshirani et al. (2002) *Proc. Natl. Acad. Sci.* 99:6567-6572.

Another method is the nearest shrunken centroids, which identifies subsets of genes that best characterize each class. This method is general and can be used in many other classification problems. It can also be applied to survival analysis problems. The method computes a standardized centroid for each class, which is the average gene expression for each gene in each class divided by the within-class standard deviation for that gene. Nearest centroid classification takes the gene expression profile of a new sample, and compares it to each of these class centroids. The class whose centroid that it is closest to, in squared distance, is the predicted class for that new sample. Nearest shrunken centroid classification makes one important modification to standard nearest centroid classification. It "shrinks" each of the class centroids toward the overall centroid for all classes by an amount we call the threshold. This shrinkage consists of moving the centroid towards zero by threshold, setting it equal to zero if it hits zero. For example if threshold was 2.0, a centroid of 3.2 would be shrunk to 1.2, a centroid of −3.4 would be shrunk to −1.4, and a centroid of 1.2 would be shrunk to zero. After shrinking the centroids, the new sample is classified by the usual nearest centroid rule, but using the shrunken class centroids. This shrinkage has two advantages: 1) it can make the classifier more accurate by reducing the effect of noisy genes; and 2) it does automatic gene selection. The user decides on the value to use for threshold. Typically one examines a number of different choices.

Alternatively, prognostic performance of the biomarkers and/or other clinical parameters can be assessed by Cox Proportional Hazards Model Analysis, which is a regression method for survival data that provides an estimate of the hazard ratio and its confidence interval. The Cox model is a well-recognized statistical method for exploring the relationship between the survival of a patient and particular variables. This statistical method permits estimation of the hazard (i.e., risk) of individuals given their prognostic variables (e.g., overexpression of particular biomarkers, as described herein). Cox model data are commonly presented as Kaplan-Meier curves or plots. The "hazard ratio" is the risk of death at any given time point for patients displaying particular prognostic variables. See generally, Spruance et al. (2004) *Antimicrob. Agents & Chemo.* 48:2787-2792.

The biomarkers of interest can be statistically significant for assessment of the likelihood of thymic cancer recurrence or death due to the underlying thymic cancer. Methods for assessing statistical significance are well known in the art and include, for example, using a log-rank test, Cox analysis and Kaplan-Meier curves. A p-value of less than 0.05 can be used to constitute statistical significance.

The expression levels of at least one biomarker in a thymic tumor sample can be indicative of a poor thymic cancer prognosis and thereby used to identify individuals who are more likely to suffer a recurrence of the underlying cancer. The therefore methods involve detecting the expression levels of at least one biomarker in a thymic tumor sample that is indicative of early stage disease.

In some embodiments, overexpression of a biomarker or combination of biomarkers of interest in a sample can be indicative of a poor cancer prognosis. As used herein, "indicative of a poor prognosis" is intended that altered expression of particular biomarkers or combination of biomarkers is associated with an increased likelihood of relapse or recurrence of the underlying cancer or tumor, metastasis or death. For example, "indicative of a poor prognosis" may refer to an increased likelihood of relapse or recurrence of the underlying cancer or tumor, metastasis, or death within ten years, such as five years. In other aspects of the invention, the absence of overexpression of a biomarker or combination of biomarkers of interest is indicative of a good prognosis. As used herein, "indicative of a good prognosis" refers to an increased likelihood that the patient will remain cancer free. In some embodiments, "indicative of a good prognosis" refers to an increased likelihood that the patient will remain cancer-free for ten years, such as five years.

As noted above, polynucleotide and polypeptide biomarkers for use in prognosing thymic cancer can include COL11A1, DACT3, SLC9A2, PRRX1, PDGFRL, SCUBE2, MAB21L2, FCGBP, MAOA, CTGF, MET, NEBL, GPR98, GLDN, IGSF11, PCDH19, C6orf118, GOLSYN, BCMO1, PTN, LAMP2, LRRC17, DDX60, GEM, FRMD6, KGFLP1, C9orf93, NGB, AKR1B10, JPH1 STC1, STC2 and SLC7A11.

Alternatively, polynucleotide and polypeptide biomarkers for use herein can include DACT3, JPH1, AKR1B10, COL11A1, SLC9A2, PDGFRL, FCGBP, PRRX1, SERPINF1, NGB, SCUBE2, MAB21L2, LEPR, LCA5, GPR98, RSPO3, STC1, STC2 and SLC7A11.

Alternatively, polynucleotide and polypeptide biomarkers for use herein can include DACT3, JPH1, AKR1B10, COL11A1, SLC9A2, PDGFRL, FCGBP, PRRX1, SERPINF1, NGB, STC1, STC2 and SLC7A11.

Alternatively, polynucleotide and polypeptide biomarkers for use herein can include DACT3, JPH1, AKR1B10, COL11A1, SLC9A2, PDGFRL, FCGBP, PRRX1, SERPINF1 and NGB.

Additional polynucleotide and polypeptide biomarkers for use herein are described above in the section defining biomarkers of the present invention.

Polynucleotide and polypeptide biomarkers for use herein as controls or references can include IPO8, TFRC, UBC, PGE1 and GAPDH.

With respect to prognosing metastasis in thymic cancer, preferred biomarkers can be DACT3, JPH1, AKR1B10, COL11A1, SLC9A2, PDGFRL, FCGBP, PRRX1, SERPINF1, NGB, STC1, STC2 and SLC7A11, where overexpression of DACT3, COL11A1, SLC9A2, PDGFRL, FCGBP, PRRX1 and SERPINF1, in connection with reduced expression of JPH1, AKR1B10, NGB, STC1, STC2 and SLC7A11, indicates a low likelihood of metastasis and good/favorable prognosis.

In certain embodiments, the methods of the invention implement a computer program and computer system. For example, a computer program can be used to perform the algorithms described herein. A computer system can also store and manipulate data generated by the methods of the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part of the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker expression data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

Methods of Treating Thymic Cancers

The biomarkers, kits and detection, diagnosing and prognosing methods described above can be used to assist in selecting appropriate treatment regimen and to identify individuals that would benefit from more aggressive therapy.

As noted above, approaches to the treating thymic cancers include surgery, immunotherapy, chemotherapy, radiation therapy, a combination of chemotherapy and radiation therapy, or biological therapy. Chemotherapeutics that have been used in the treatment of thymomas and thymic carcinomas include, but are not limited to, doxorubicin (Adriamycin), cisplatin, ifosfamide, and corticosteroids (prednisone). Often, these agents are given in combination to increase their effectiveness. Combinations used to treat thymic cancer include the combination of cisplatin, doxorubicin, etoposide and cyclophosphamide, as well as the combination of cisplatin, doxorubicin, cyclophosphamide and vincristine.

The methods described above therefore find particular use in selecting appropriate treatment for early-stage thymic cancer patients. The majority of individuals having thymic cancer diagnosed at an early-stage of the disease enjoy long-term survival following surgery and/or radiation therapy without further adjuvant therapy. However, a significant percentage of these individuals will suffer disease recurrence or death, leading to clinical recommendations that some or all early-stage thymic cancer patients should receive adjuvant therapy (e.g., chemotherapy). The methods of the present invention can identify this high-risk, poor prognosis population of individuals having early-stage thymic cancer and thereby can be used to determine which ones would benefit from continued and/or more aggressive therapy and close monitoring following treatment. For example, individuals having early-stage thymic cancer and assessed as having a poor prognosis by the methods disclosed herein may be selected for more aggressive adjuvant therapy, such as chemotherapy, following surgery and/or radiation treatment. In particular embodiments, the methods of the present invention may be used in conjunction with standard procedures and treatments to permit physicians to make more informed thymic cancer treatment decisions.

EXAMPLES

The invention will be more fully understood upon consideration of the following non-limiting examples, which are offered for purposes of illustration, not limitation.

Example 1: Gene Expression Analysis of Frozen Thymomas

Methods and Results:

a DNA-Mediated Annealing, Selection and Ligation ("DASL"™) Microarray Platform (Illumina; San Diego, Calif.) was used. RNA was extracted from 36 fresh frozen thymomas and individualed to gene profiling for the analysis of 24,000 gene probes. Clinical treatment and follow-up and pathology data was available on the individuals from which the samples were obtained.

Approximately 8,000 genes were expressed at background levels and a number of genes were associated with the presence of advanced stage disease at diagnosis, recurrence or metastasis (FIG. 1) Importantly, histologic classification was a poor predictor of clinical behavior of tumors in this series. As shown in Tables 4 and 5, the top differentially expressed genes were identified in metastatic cases and in early stage phenotypes.

TABLE 4

Top Differentially Expressed Genes in MET_YES vs. MET_NO Phenotypes.

| Gene |
| --- |
| COL11A1 |
| DACT3 |
| SLC9A2 |
| PRRX1 |
| PDGFRL |
| SCUBE2 |
| MAB21L2 |
| FCGBP |
| MAOA |
| CTGF |
| MET |
| NEBL |
| GPR98 |
| GLDN |
| IGSF11 |
| PCDH19 |
| C6orf118 |
| GOLSYN |
| BCMO1 |
| PTN |
| LAMP2 |
| LRRC17 |
| DDX60 |
| GEM |
| FRMD6 |
| KGFLP1 |
| C9orf93 |
| NGB |
| AKR1B10 |
| JPH1 |
| STC1 |
| STC2 |
| SLC7A11 |

TABLE 5

Top Differentially Expressed Genes in Early Stage (I/II) vs. Late Stage (III/IV) Phenotypes.

| Gene |
| --- |
| JPH1 |
| ALDH1A3 |
| SPOCK1 |
| NGB |
| STC1 |
| STC2 |
| AKR1B10 |

TABLE 5-continued

Top Differentially Expressed Genes in Early Stage (I/II) vs. Late Stage (III/IV) Phenotypes.

| Gene |
|---|
| ENPEP |
| GOLSYN |
| RPL39 |
| LAMP2 |
| ABHD7 |
| RBPMS2 |
| C9orf93 |
| SESN3 |
| MRRF |
| NEBL |
| PRRX1 |
| C14orf39 |
| LEPR |
| DTNA |
| LCA5 |
| RSPO3 |
| IGF2BP2 |
| GPR98 |
| TIAM2 |
| SLC9A2 |
| MAB21L2 |
| SCUBE2 |
| DACT3 |
| COL11A1 |
| SLC7A11 |

Figure 2A:
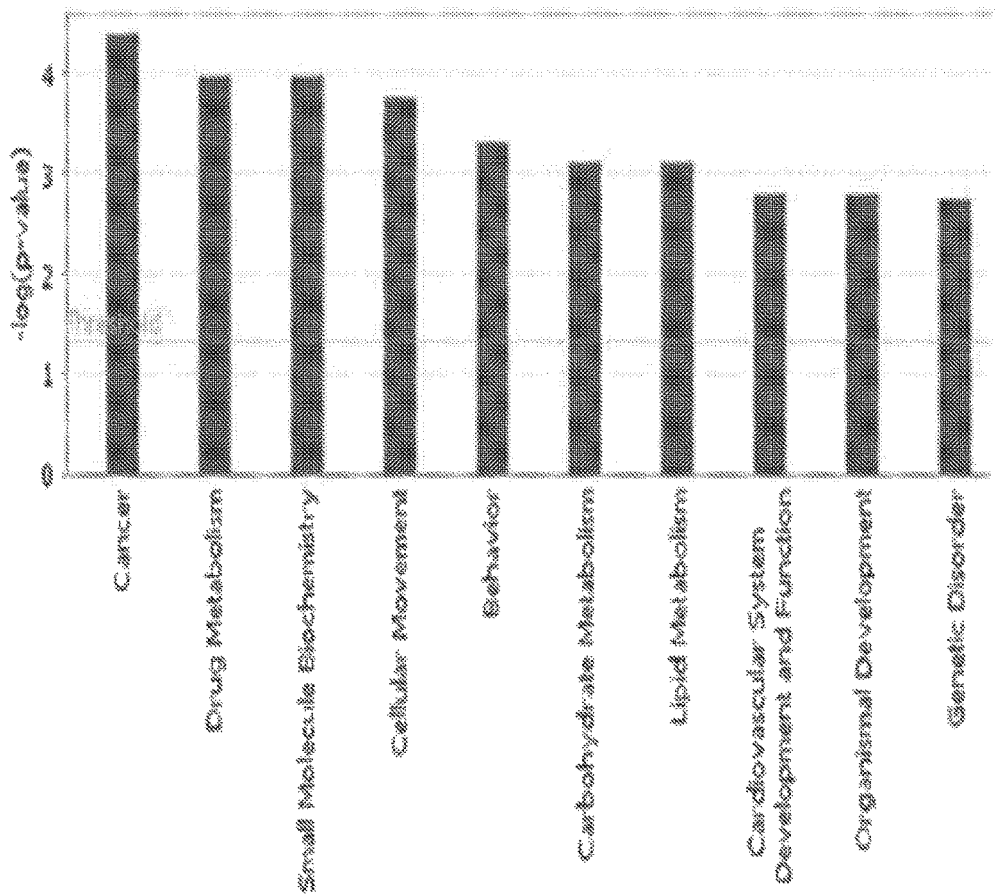
FIGS. 2A-2D show the "Biological Processes and Canonical Pathways" associated with metastasis and stage using Ingenuity Pathway Analysis ("IPA"). The top ten significant biological functions associated with metastasis (FIG. 2A) and stage (FIG. 2B) and canonical pathways associated with metastasis (FIG. 2C) and stage (FIG. 2D) were grouped based on the P values using a Right-Tailed Fisher Exact Test with a threshold of less than 0.05.
Figure 2B:
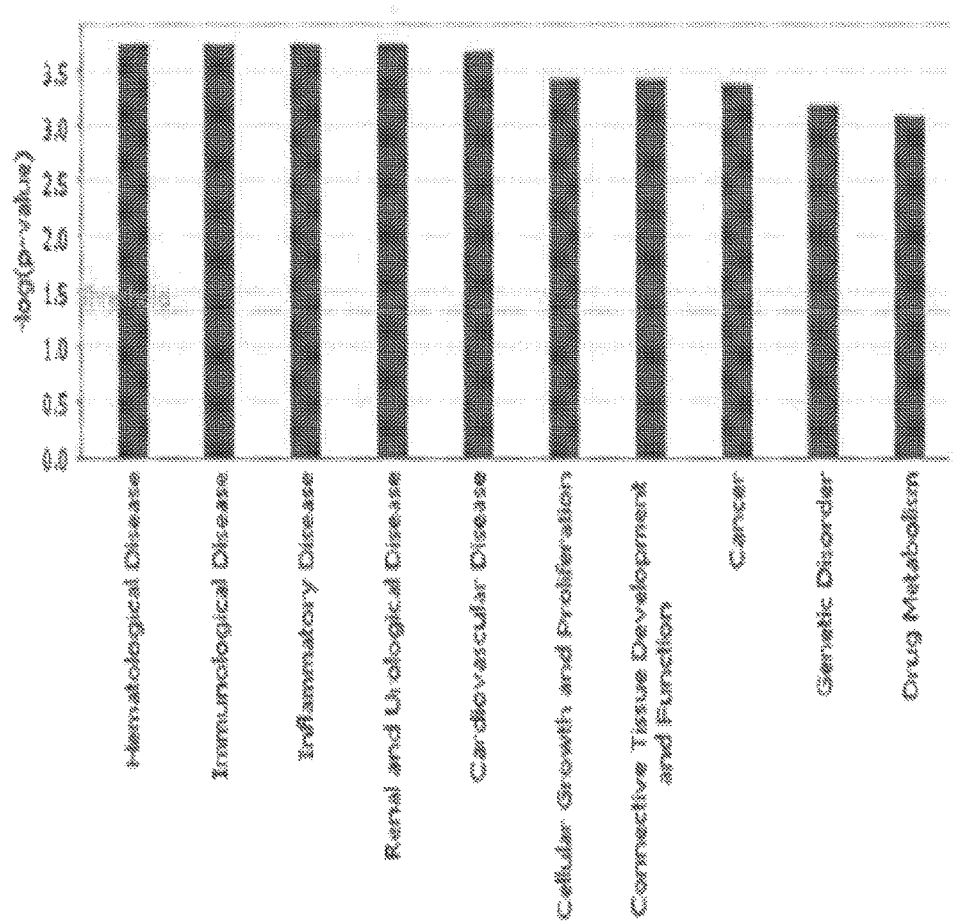
Figure 2C:
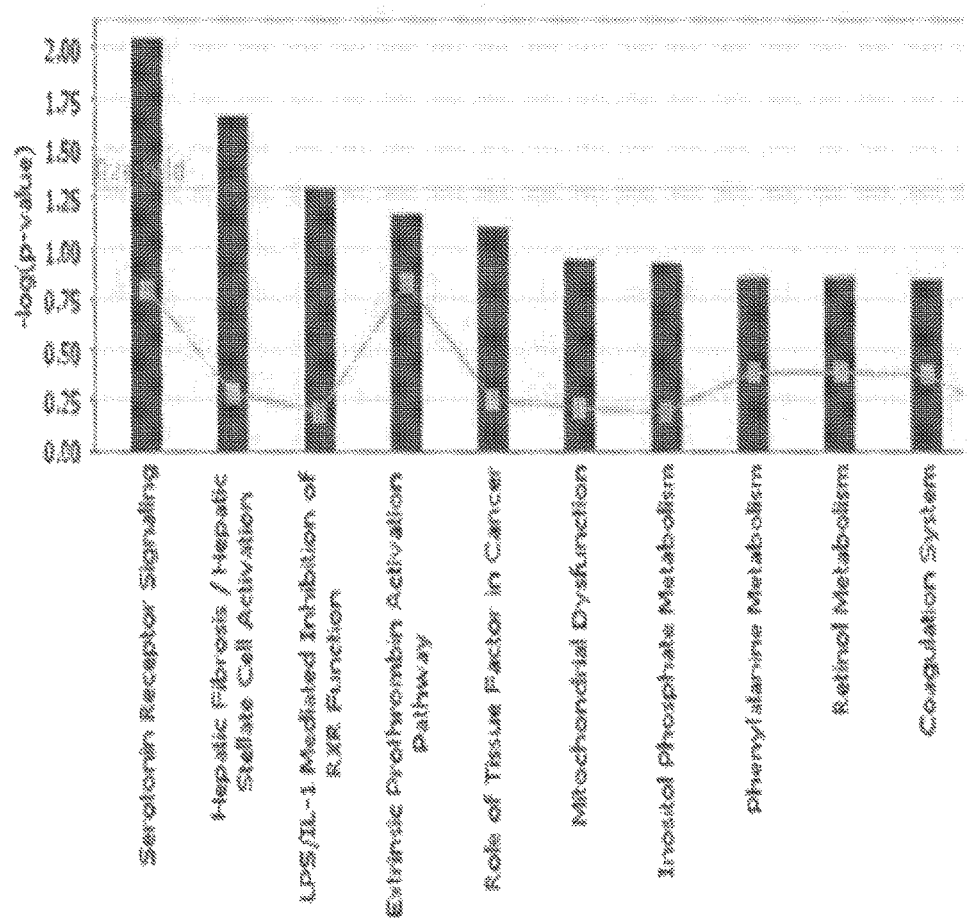
Figure 2D:
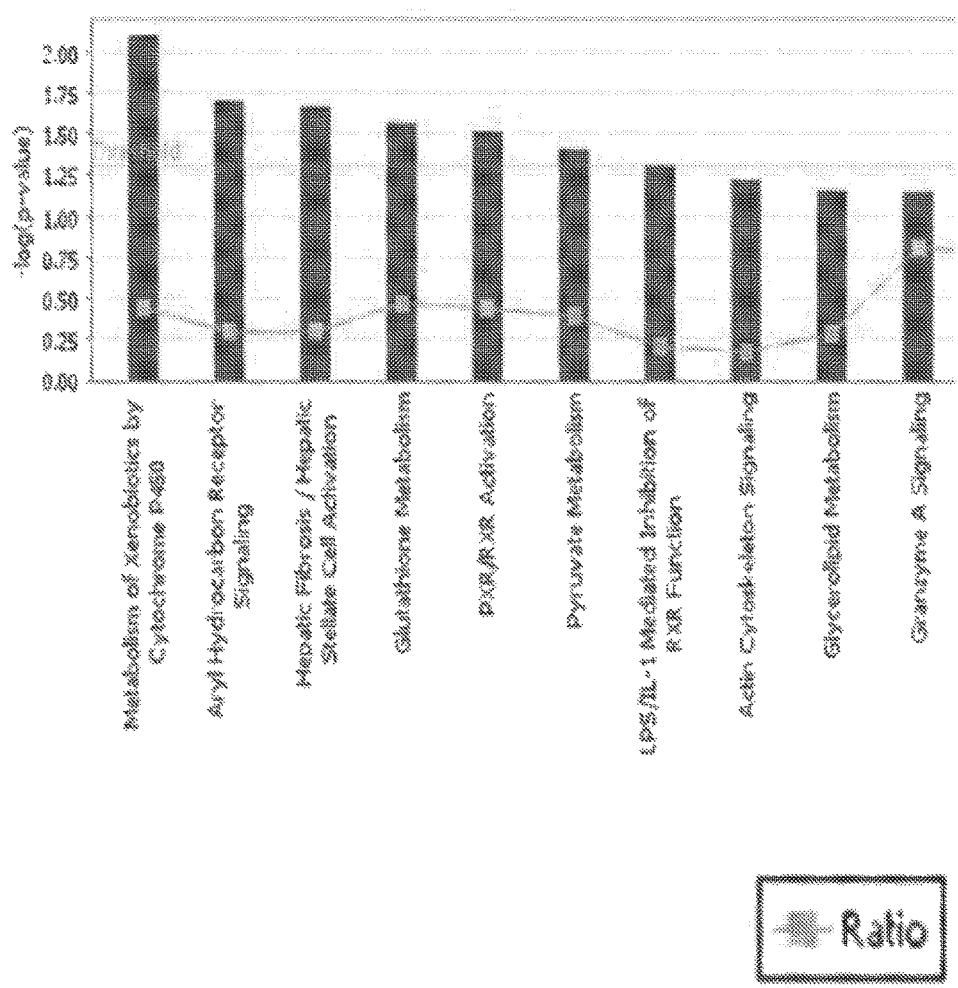

The top ten significant biological functions for metastatic cases (FIG. 2A) and early stage phenotypes (FIG. 2B) and canonical pathways for metastatic cases (FIG. 2C) and early stage phenotypes (FIG. 2D) were grouped based on the P values using a Right-Tailed Fisher exact test with a threshold of less than 0.05. See also, Tables 6 and 7.

TABLE 6

Top "Biological Function" Enrichment Using IPA in Metastasis YES vs. NO.

| Category | Function | Function Annotation | p-value | # of Molecules |
|---|---|---|---|---|
| Cancer | cancer | cancer | 4.29E−05 | 29 |
| Cancer | tumor | tumor | 6.20E−04 | 20 |
| Cancer | metastasis | metastasis of tumor cell lines | 1.41E−03 | 2 |
| Cancer | metastasis | metastasis of carcinoma cell lines | 4.35E−03 | 1 |
| Cancer | metastasis | metastasis | 4.35E−03 | 6 |
| Cancer | transformation | transformation of carcinoma cells | 4.35E−03 | 1 |
| Cancer | malignant tumor | malignant tumor | 5.69E−03 | 15 |
| Cancer | tumorigenesis | tumorigenesis of cells | 5.81E−03 | 3 |
| Cancer | leiomyoma | leiomyoma | 7.78E−03 | 5 |
| Cancer | invasion | invasion of extracellular matrix | 8.68E−03 | 1 |
| Cancer | carcinoma | carcinoma | 1.96E−02 | 12 |
| Cancer | breast cancer | breast cancer | 2.69E−02 | 9 |
| Cellular Movement | cell movement | cell movement of squamous cell carcinoma cell lines | 2.58E−02 | 1 |
| Cellular Movement | cell movement | cell movement of tumor cell lines | 4.41E−02 | 3 |
| Cellular Movement | migration | migration of tumor cells | 1.31E−02 | 2 |
| Lipid Metabolism | metabolism | metabolism of phosphatidic acid | 8.54E−04 | 3 |
| Lipid Metabolism | metabolism | metabolism of terpenoid | 8.16E−03 | 3 |
| Organismal Development | angiogenesis | angiogenesis | 1.67E−03 | 4 |
| Organismal Development | angiogenesis | angiogenesis of blood vessel | 1.94E−03 | 3 |

TABLE 7

Top "Biological Function" Enrichment Using IPA in Stage I/II vs III/IV.

| Category | Function | Function Annotation | p-value |
|---|---|---|---|
| Cellular Growth and Proliferation | proliferation | proliferation of cancer cells | 1.31E−02 |
| Cellular Growth and Proliferation | proliferation | proliferation of multilineage progenitor cells | 3.43E−02 |
| Cellular Growth and Proliferation | proliferation | proliferation of cell lines | 4.09E−02 |
| Cancer | tumorigenesis | tumorigenesis | 7.56E−04 |
| Cancer | tumor | tumor | 1.67E−03 |
| Cancer | malignant tumor | malignant tumor | 2.18E−03 |
| Cancer | breast cancer | breast cancer | 1.00E−02 |
| Cancer | carcinoma | carcinoma | 1.96E−02 |
| Cancer | infection | infection of leukemia cell lines | 4.68E−02 |
| Cell Morphology | morphogenesis | morphogenesis of endothelial cells | 9.98E−04 |
| Cell Morphology | tubulation | tubulation of microvascular endothelial cells | 2.16E−02 |
| Cellular Development | morphogenesis | morphogenesis of endothelial cells | 9.98E−04 |
| Cellular Development | growth | growth of epidermal cells | 2.72E−03 |
| Cellular Development | differentiation | differentiation of epithelial cell lines | 8.68E−03 |
| Cellular Development | differentiation | differentiation of connective tissue cells | 9.14E−03 |
| Cellular Development | differentiation | differentiation of cells | 1.07E−02 |
| Cell Cycle | cell division process | cell division process of endothelial cells | 1.41E−03 |

TABLE 7-continued

Top "Biological Function" Enrichment Using IPA in Stage I/II vs III/IV.

| Category | Function | Function Annotation | p-value |
|---|---|---|---|
| Cell Cycle | cell division process | cell division process of normal cells | 1.71E−02 |
| Cell Cycle | cell stage | cell stage of normal cells | 4.56E−03 |
| Cell Cycle | S phase | entry into S phase of Kaposi's sarcoma cells | 8.68E−03 |
| Cell Death | apoptosis | apoptosis of normal cells | 1.85E−02 |
| Cell Death | apoptosis | apoptosis of endothelial cells | 2.55E−02 |
| Cell Death | lysis | lysis of lymphoma cell lines | 1.73E−02 |
| Cellular Movement | invasion | invasion of microvascular endothelial cells | 8.68E−03 |
| Cellular Movement | invasion | invasion of endothelial cell lines | 3.85E−02 |
| Cellular Movement | migration | migration of endothelial cells | 1.28E−02 |
| Cellular Movement | migration | migration of lymphatic endothelial cells | 3.43E−02 |
| Cellular Movement | migration | migration of mesangial cells | 3.85E−02 |

Figure 3:
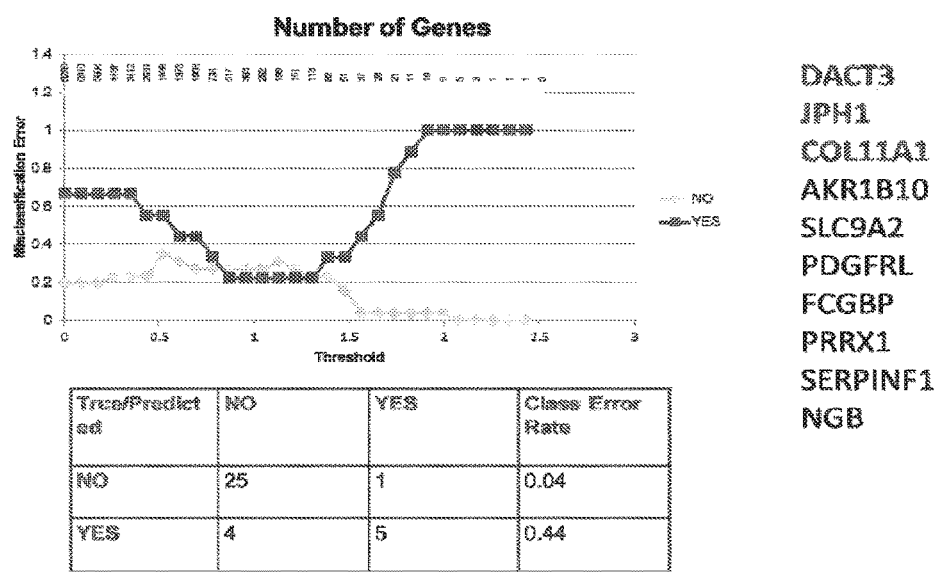
FIG. 3 shows an identification of a set of ten (10) genes that predicts a lack of metastasis with an error rate 4% using Prediction Analysis of Microarrays ("PAM"). Individual cross validation plots were shown for Metastasis Yes phenotype (YES, blue) and Metastasis NO phenotype (NO, green). The threshold value (1.56) was chosen to use for shrinkage and prediction with an error rate 4%.
Figure 4:
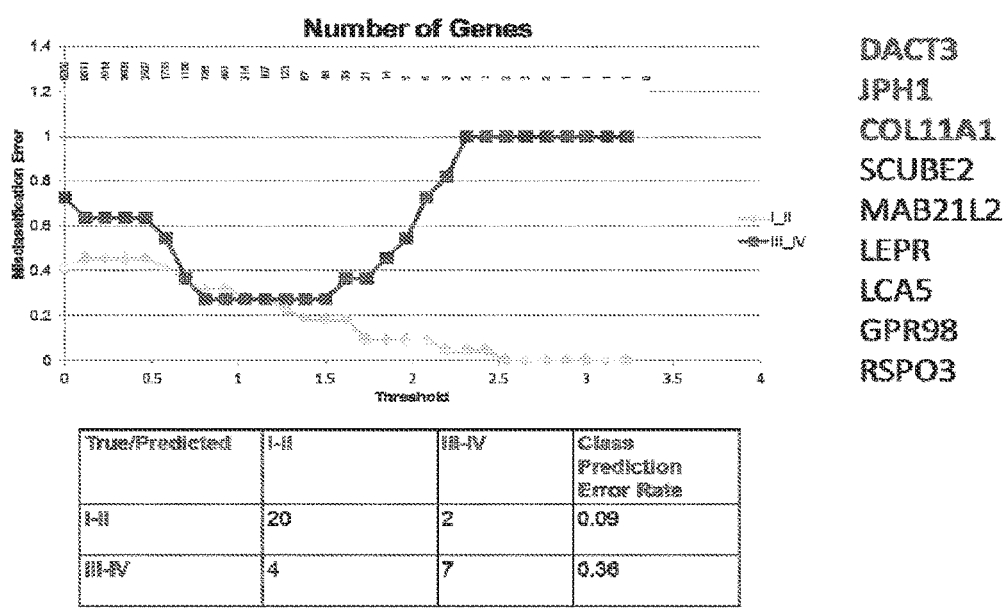
FIG. 4 shows an identification of a set of nine (9) genes that predicts the presence of early stage (Stage I/II) with an error rate 9% using PAM. Individual cross validation plots were shown for Stage I/II (green) and Stage III/IV (blue) disease. The threshold value (1.73) was chosen to use for shrinkage and prediction with an error rate of 9%.

PAM showed that a set of ten genes could be used to predict absence of metastasis with an error rate of 4% (FIG. 3). Similarly, a set of nine genes could be used to predict early stage disease (Stage I-II) with an error rate of approximately 10% (FIG. 4). See also, Table 8. This data indicates that individuals identified as good prognosis are very unlikely to develop adverse events and can be spared from toxic chemo-radiation.

TABLE 8

Genes for the Validation of the Lack of Metastasis or Early Stage Phenotype.

| Gene Symbol | Assay ID | Amplicon Length | Gene |
|---|---|---|---|
| DACT3 | Hs00376817_g1 | 85 | Target |
| JPH1 | Hs00976073_m1 | 73 | Target |
| AKR1B10 | Hs00252524_m1 | 95 | Target |
| COL11A1 | Hs01097664_m1 | 56 | Target |
| SLC9A2 | Hs00268166_m1 | 81 | Target |
| PDGFRL | Hs00185122_m1 | 69 | Target |
| FCGBP | Hs00175398_m1 | 73 | Target |
| PRRX1 | Hs00246567_m1 | 67 | Target |
| SERPINF1 | Hs01106937_m1 | 84 | Target |
| NGB | Hs00222034_m1 | 75 | Target |
| SCUBE2 | Hs00221277_m1 | 64 | Target |
| MAB21L2 | Hs00740710_s1 | 93 | Target |
| LEPR | Hs00900242_m1 | 76 | Target |
| LCA5 | Hs01099550_m1 | 66 | Target |
| GPR98 | Hs01022907_m1 | 62 | Target |
| RSPO3 | Hs01072567_m1 | 77 | Target |
| STC1 | Hs00174970_m1 | 81 | Target |
| STC2 | Hs00175027_m1 | 72 | Target |
| SLC7A11 | Hs00921938_m1 | 57 | Target |
| IPO8 | Hs00183533_m1 | 71 | Reference |
| TFRC | Hs00951083_m1 | 66 | Reference |
| UBC | Hs00824723_m1 | 71 | Reference |
| PGK1 | Hs99999906_m1 | 75 | Reference |
| GAPDH | control in the array | | Reference |

Figure 5A:
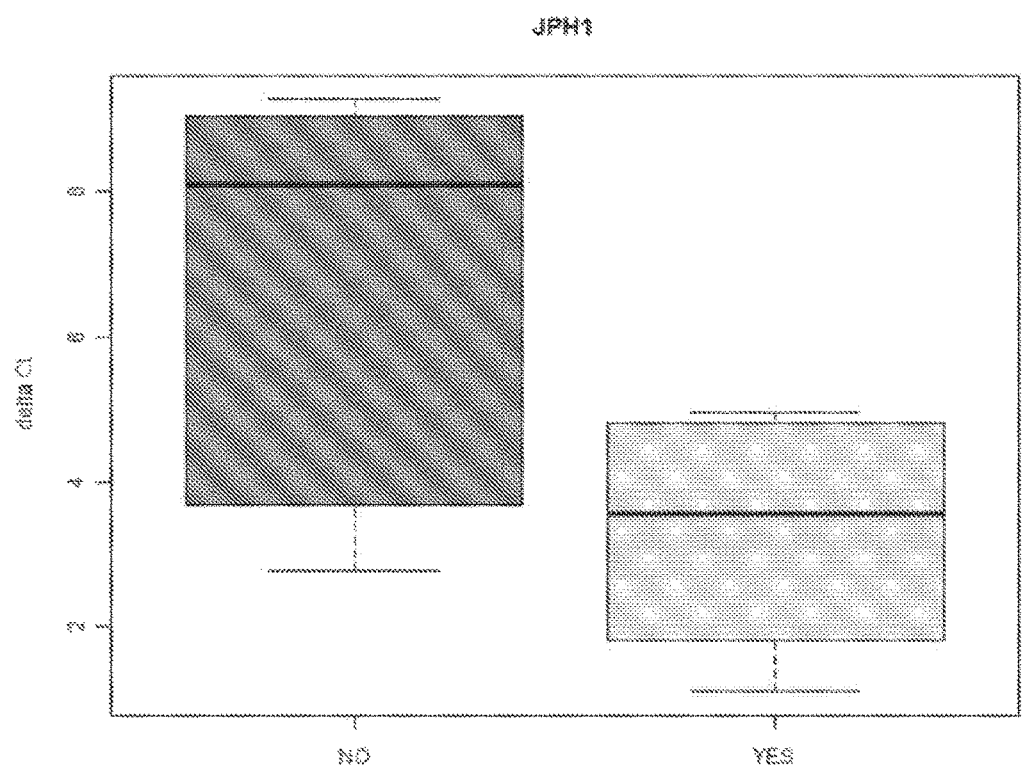
FIGS. 5A-5H show delta cycle threshold (delta CT) values for relative mRNA expression of JPH1 (FIG. 5A), AKR1B10 (FIG. 5B), STC1 (FIG. 5C) and COL1 1A1 (FIG. 5D) and average fold change for relative mRNA expression of JPH1 (FIG. 5E), AKR1B10 (FIG. 5F), STC1 (FIG. 5G) and COL1 1A1 (FIG. 5H) in relation to metastasis. Delta cycle threshold (delta CT) values and average fold change were calculated in metastasis YES phenotype compared with metastasis NO phenotype using DataAssist Software (Applied Biosystems; Foster City, Calif.). Data is normalized to the geometric mean of the reference genes IPO8 and TFRC.
Figure 5B:
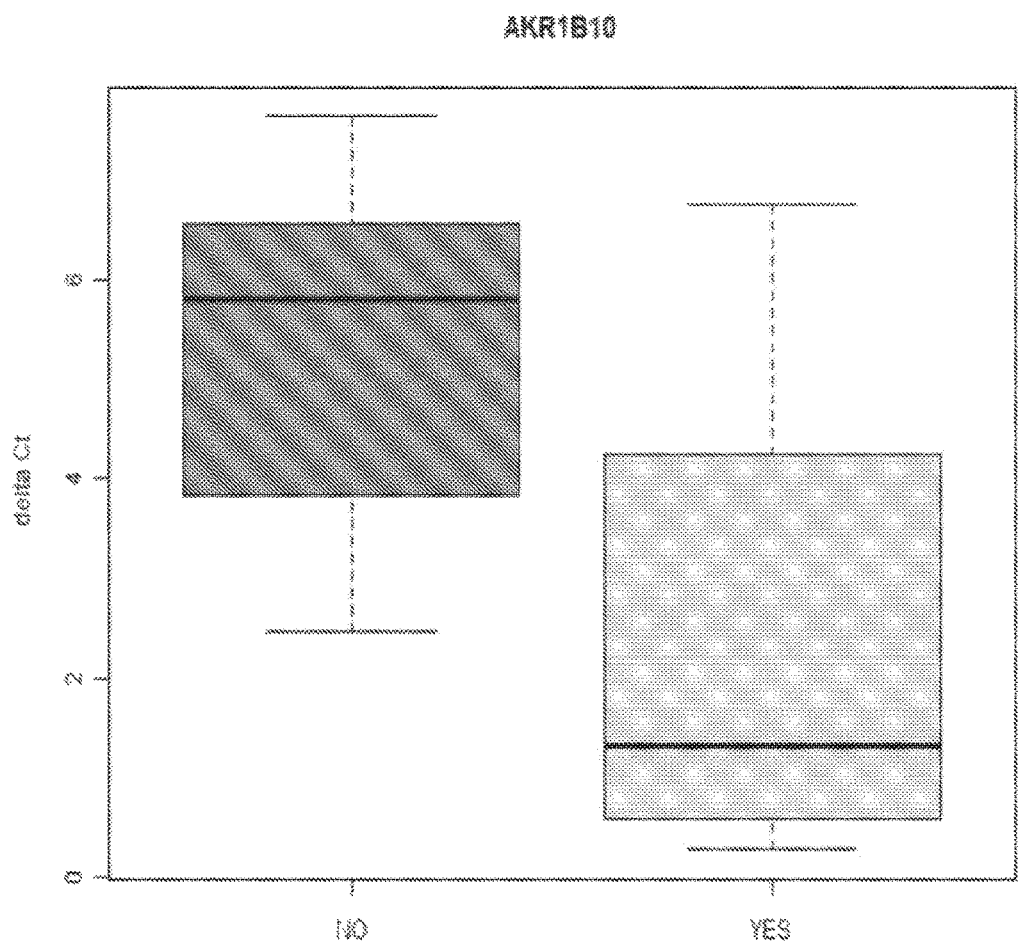
Figure 5C:
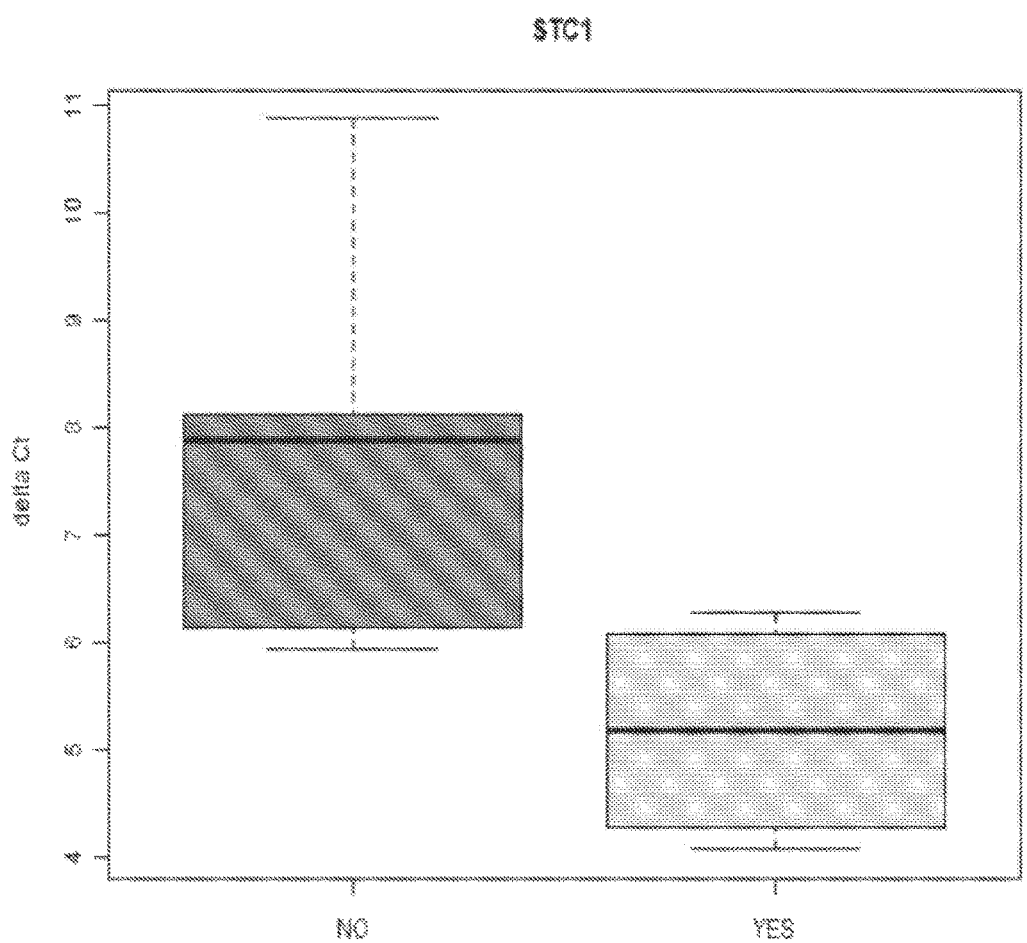
Figure 5D:
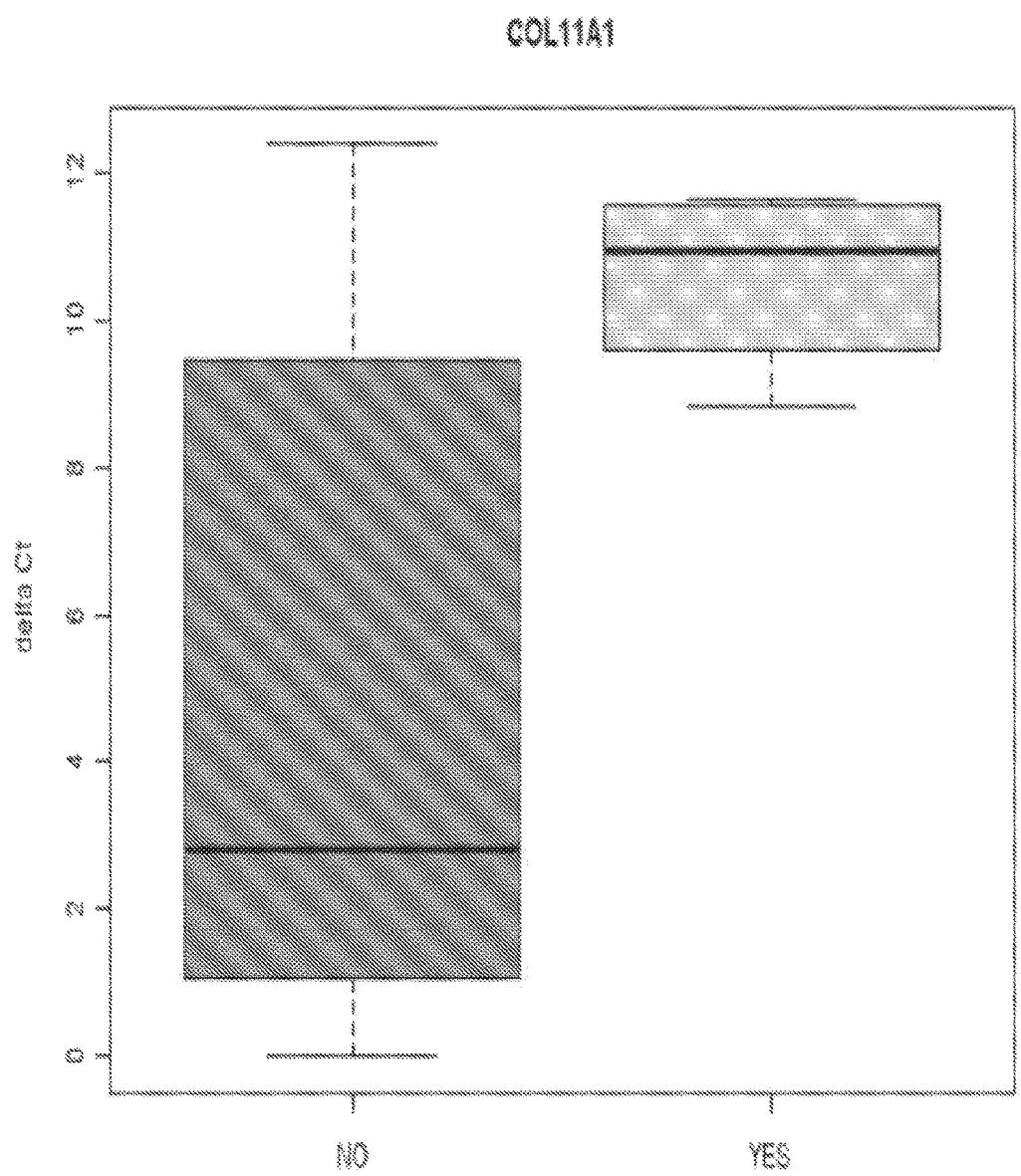
Figure 5E:
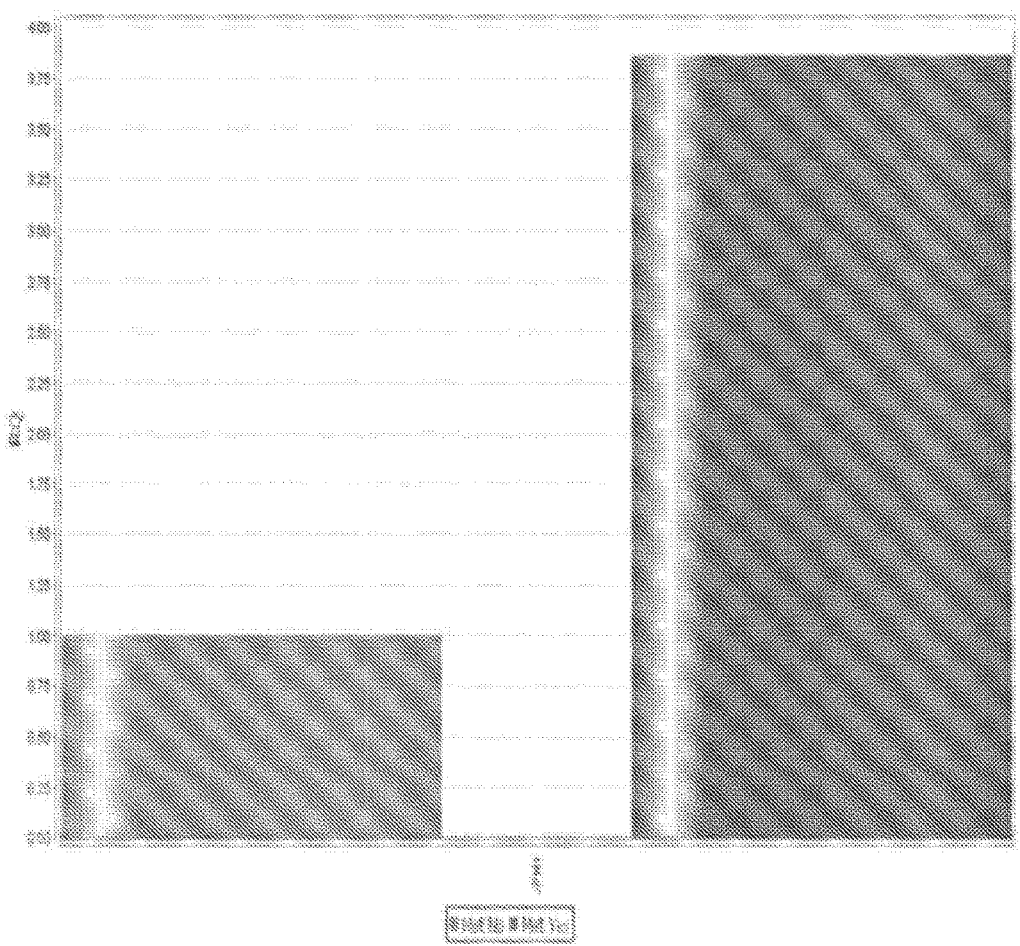
Figure 5F:
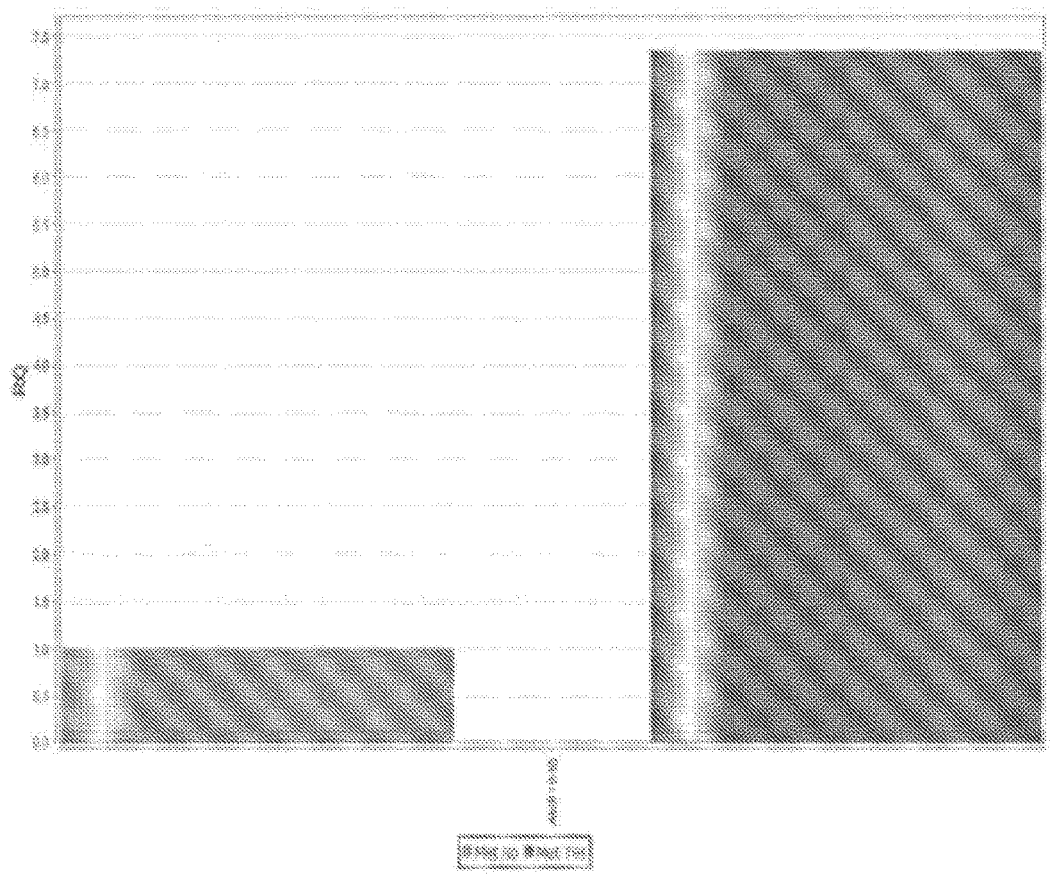
Figure 5G:
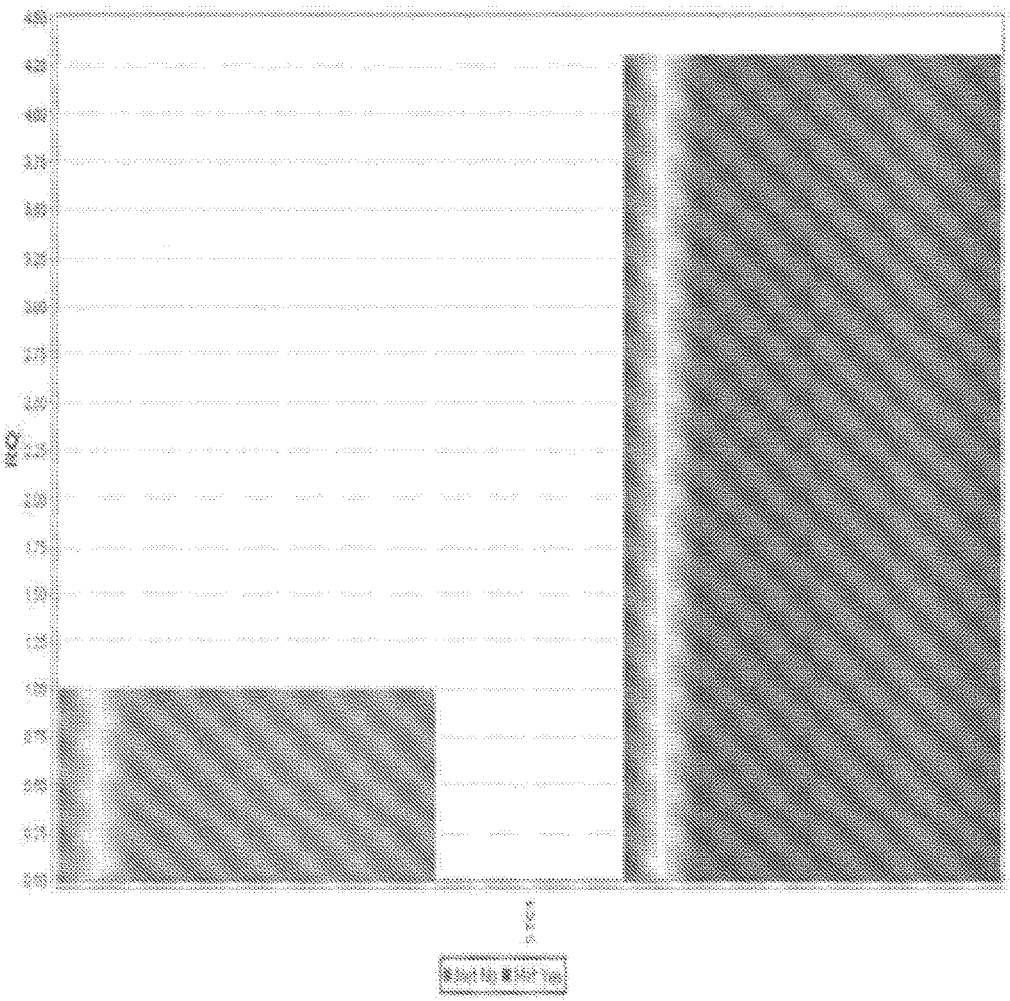
Figure 5H:
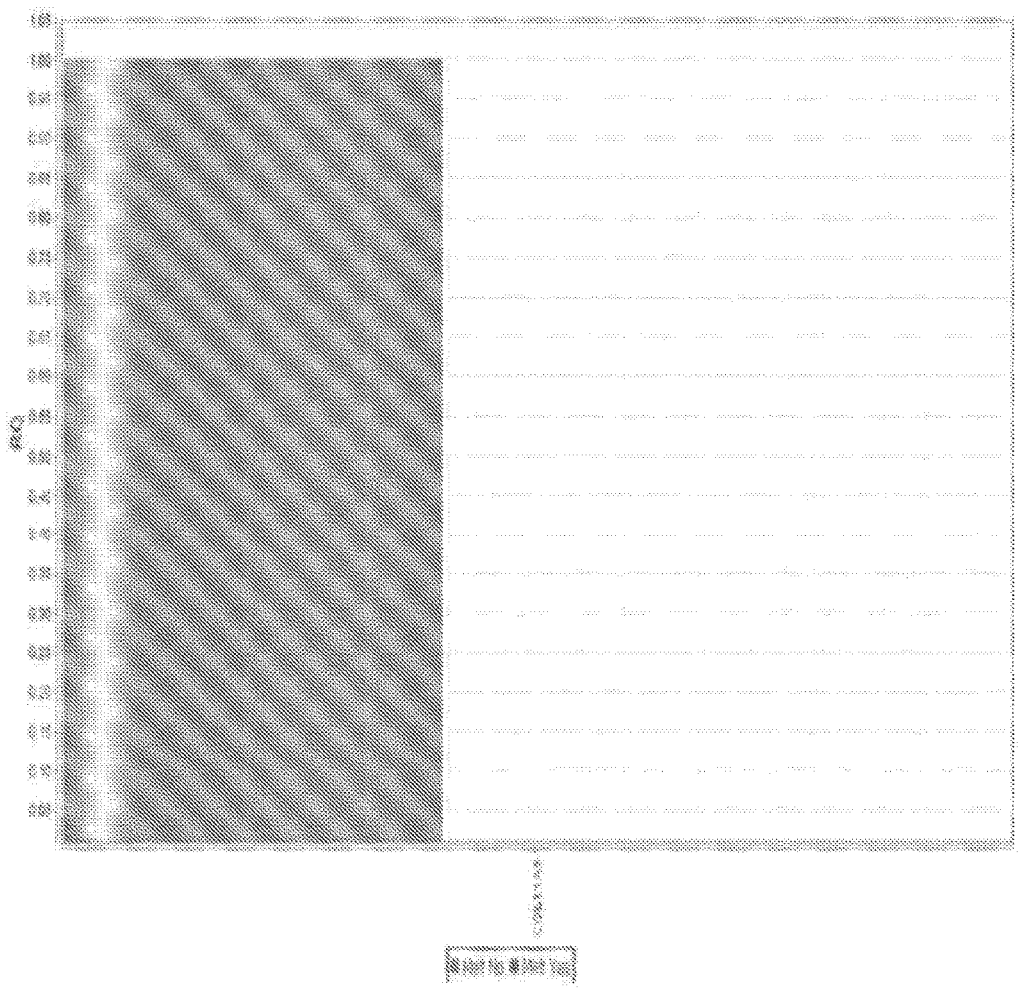

Additionally, delta cycle threshold (delta CT) values for relative mRNA expression was analyzed for JPH1 (FIG. 5A), AKR1B10 (FIG. 5B), STC1 (FIG. 5C) and COL11A1 (FIG. 5D) and average fold change for relative mRNA expression of JPH1 (FIG. 5E), AKR1B10 (FIG. 5F), STC1 (FIG. 5G) and COL11A1 (FIG. 5H) in relation to metastasis. Delta cycle threshold (CT) values and average fold change were calculated in metastasis YES phenotype and compared with metastasis NO phenotype using DataAssist Software (Applied Biosystems; Foster City, Calif.). Data is normalized to the geometric mean of the reference genes IPO88 and TFRC.

Example 2: Stanniocalcins ("STCs") are Overexpressed in Metastatic Thymomas

Methods and Results:

mRNA expression profiling was performed on 36 fresh frozen thymomas from individuals operated upon at the IUSCC using ILLUMINA® platform [Whole Genome DASL® (cDNA-mediated annealing, selection, extension and ligation) Assay] and correlated with clinical outcomes including presence of recurrences and metastases.

Based on the Analysis of Variance (ANOVA), STC1 and STC2 were selected showing significantly elevated mRNA levels in metastasis-associated samples compared to non-metastatic samples (p<0.05).

Importantly, upregulation of STC1 and STC2 was observed in metastatic cases (relative to non-metastatic cases) using quantitative real-time RT-PCR (qRT-PCR) in a small series of cases (n=5 for MET-NO; and n=4 for MET-YES group).

All of the patents, patent applications, patent application publications and other publications recited herein are hereby incorporated by reference as if set forth in their entirety.

Example 3: A Prognostic GEP Signature to Determine Metastatic Risk Associated with Thymomas The following methods were used to generate the results described below:
a. Patients All patients were seen at Indiana University Melvin and Bren Simon Cancer Center (IUSCC) for management of thymoma. Of the over 600 cases of thymic tumors seen at IUSCC, 137 cases of thymomas with archival blocks were available for analysis. The histology was reviewed by a single pathologist (SB) using the WHO criteria; cases with multiple histological subtypes were scored on the basis of the predominant subtype. Cases with sufficient tissue (n=125) were selected for gene expression analysis. Clinical data on all these patients was obtained by chart review or contacting the offices of the primary care physician. Studies were approved by the Institutional Review Board of Indiana University. Demographic and clinical characteristics including the follow-up information of the patients were acquired by review of the medical charts and contacting physician offices. Table 9 shows the demographics of the training and validation sample sets for the variables of age, gender, Masaoka stage, WHO classification, and presence of auto-immune disease. Selection of training set samples was primarily based upon shortest time to metastasis (average time to metastasis=1.1 yrs) and longest follow up (>5 yrs, average follow up=10.4 yrs) for those samples that did not experience a metastatic event. In the validation set, 37 patients were stage I/II and 37 were stage III/IV. Using the WHO classification schema, 1 and 8 were classified as type A; 8 and 18 as type AB, 5 and 17 as type B1, 11 and 26 as type B2 and 11 and 6 as type B3. None of the patients had received neoadjuvant chemotherapy. The 50 patients had been treated by surgery only, while the others received chemo- or radiation therapy as a part of their therapy.

TABLE 9

Baseline Demographics of Training Set and Independent Validation Set.

|  | Metastatic Group | | Non-Metastatic Group | |
| --- | --- | --- | --- | --- |
|  | Training (n = 21) | Validation (n = 31) | Training (n = 15) | Validation (n = 44) |
| Median MFS/Followup (range) | 1.09 (0-13.0) | 2.53 (0-11.2) | 10.4 (5.1-18.1) | 2.82 (0.1-13.8) |
| Median Age (range) | 46 (34-85) | 43 (27-68) | 48 (31-62) | 57 (18-79) |
| Gender |  |  |  |  |
| Male | 6 (29%) | 17 (55%) | 5 (33%) | 16 (36%) |
| Female | 15 (71%) | 14 (45%) | 10 (67%) | 28 (64%) |
| Masaoka Stage |  |  |  |  |
| I | 2 (10%) | 5 (16%) | 10 (67%) | 16 (36%) |
| II | 3 (14%) | 3 (10%) | 5 (33%) | 13 (30%) |
| III | 5 (24%) | 13 (42%) | 0 (0%) | 14 (32%) |
| IV | 11 (52%) | 10 (32%) | 0 (0%) | 0 (0%) |
| WHO Classification |  |  |  |  |
| A | 1 (5%) | 0 (0%) | 0 (0%) | 8 (18%) |
| AB | 3 (14%) | 3 (10%) | 5 (33%) | 15 (34%) |
| B1 | 1 (5%) | 10 (32%) | 4 (27%) | 7 (16%) |
| B2 | 8 (38%) | 14 (45%) | 3 (20%) | 12 (27%) |
| B3 | 8 (38%) | 4 (13%) | 3 (20%) | 2 (4.5%) |
| Autoimmune Disease |  |  |  |  |
| Yes | 12 (57%) | 9 (29%) | 6 (40%) | 14 (32%) |
| No/not stated | 9 (43%) | 22 (71%) | 9 (60%) | 30 (68%) | b. Sample Preparation

Paraffin embedded blocks with tumor cells occupying less than 75 percent of the section area were excluded from the study. In all but 3 cases included in the study, the blocks were entirely composed of tumor and no further dissection was required. In these 3 cases, tumor was macrodissected from the adherent lung tissue. RNA was extracted from five 10-µm thick sections in a CAP-accredited CLIA certified laboratory using the Ambion RecoverAll Total Nucleic Acid Isolation Kit for FFPE (Life Technologies, Grand Island, N.Y.).

Tissue processing and RNA isolation: 5×10-µm thick FFPE sections obtained from primary thymoma tumors were macrodissected and collected into a single 1.5 ml microcentrifuge tube. Tissue was deparaffinized and processed according to the Ambion RecoverAll Total Nucleic Acid Isolation Kit (Life Technologies, NJ) protocol. Following nucleic acid isolation, protein degradation, and RNA isolation procedures described in the RecoverAll Kit, RNA was eluted from the filter cartridge with 60 µl of nuclease-free water.

cDNA generation and RT-PCR analysis: All nucleic acid quantitation and evaluation steps were performed using the Nanodrop 1000 spectrophotometer according to the manufacturer's instructions. Conversion of 1 µg of RNA to cDNA was carried out in a 20 µl reaction using the Applied Biosystems HiCapacity cDNA Reverse Transcription Kit (Life Technologies, NJ). Following cDNA synthesis a 14-cycle pre-amplification step was performed in a 96-well plate for all samples using pooled TaqMan assays from the 23 genes (19 discriminant and 4 control). Pre-amplification reactions were removed to 1.5 ml centrifuge tubes and diluted 1:20 (final volume=1 ml) with 1×TE buffer.

TaqMan analysis was performed in duplicate using custom array high throughput microfluidics plates containing the 23 thymoma-specific genes. 50 µl of the pre-amplified sample was diluted 1:2 using Applied Biosystems TaqMan 2× Gene Expression Master Mix and loaded into the fill port of the custom array plate. RT-PCR was carried out in an Applied Biosystems 7900HT Fast Real-Time PCR System.

c. Assay Methods, Gene Selection and Calculation of 19-Gene Expression Signature Class 1 and Class 2

All assays were performed under CAP accredited/CLIA certified standard operating procedures (SOP) at Castle Biosciences using FFPE primary thymoma tumors for 19 discriminant genes and 4 control genes. Briefly, 19 target genes (PDGFRL, FCGBP, PRRX1, SERPINF1, NGB, SCUBE2, MAB21L2, LEPR, LCA5, GPR98, RSPO3, STC1, STC2, SLC7A11, DACT3, JPH1, AKR1B10, COL11A1, and SLC9A2) and four reference genes (IPO8, TFRC, UBC and PGK1) were assessed in both training and test studies (Table 10). Reference genes were determined using Human Endogenous Control Array (Applied Biosystems) and GeNorm software (Table 10). The optimized molecular model determines $\Delta C_t$ values for each of the nineteen genes of interest. The $\Delta C_t$ values are imported into a radial basis machine (RBM) learning algorithm, which analyzes their combined expression profile. RBM is a kernel based algorithm that calculates a predicted classification that describes how comparable the gene expression profile of the patient tissue sample is to the gene expression profiles contained in the training set. It weighs all genes equally to develop the classifier. The predicted classification is reported as Class 1 for low risk of metastasis and Class 2 for high risk of metastasis.

TABLE 10

Gene-Expression Signature.

| # genes | Gene Symbol | Assay ID (ABI)* | Ref_Seq(s) | Exon Boundary (Ref_Seq) | Assay Location | Amplicon length | Gene |
|---|---|---|---|---|---|---|---|
| | Target Genes | | | | | | |
| 1 | DACT3 | Hs00376817_g1 | NM_145056.2 | exon 2-3 | 415 | 85 | Target |
| 2 | SPH1 | Hs00976073_m1 | NM_010647.2 | exon 3-4 | 1802 | 73 | Target |
| 3 | AKR1810 | Hs00252524_m1 | NM_020299.4 | exon 3-4 | 671 | 56 | Target |
| 4 | COL11A1 | Hs01097664_m1 | NM_001190709.1 | exon 48-49 | 3963 | 56 | Target |
| | | | NM_001594.3 | exon 49-50 | 4080 | | |
| | | | NM_080629.1 | exon 49-50 | 4116 | | |
| | | | NM_080630.3 | exon 47-48 | 3752 | | |
| 5 | 5LC9AZ | Hs00268168_m1 | NM_003048.3 | exon 1-2 | 433 | 81 | Target |
| 6 | PDGFRL | Hs00185122_m1 | NM_005267.2 | exon 5-6 | 3245 | 69 | Target |
| 7 | FCGBP | Hs00175398_m1 | NM_003890.2 | exon 6-7 | 3407 | 73 | Target |
| 8 | PRRX1 | Hs00246567_m1 | NM_006202.3 | exon 1-2 | 290 | 67 | Target |
| | | | NM_02716.2 | exon 1-2 | 290 | | |
| 9 | SERPINF1 | Hs01106937_m1 | NM_002615.5 | exon 6-7 | 942 | 84 | Target |
| 10 | NGB | Hs06222034_m1 | NM_021257.3 | exon 8-4 | 695 | 75 | Target |
| 11 | SCUBEZ | Hs00221277_m1 | NM_01370690.1 | exon 4-5 | 589 | 64 | Target |
| | | | NM_020974.2 | exon 4-5 | 589 | | |
| 12 | MAB21L2 | Hs00740710_s1 | NM_006439.4 | exon 1-1 | 2358 | 93 | Target |
| 13 | LEPR | Hs00900247_m1 | NM_001003579.3 | exon 17-18 | 2669 | 76 | Target |
| | | | NM_001003530.3 | exon 17-18 | 2669 | | |
| | | | NM_091198687.1 | exon 16-17 | 2634 | | |
| | | | NM_001198688.1 | exon 16-17 | 2634 | | |
| | | | NM_001198639.1 | exon 16-17 | 2634 | | |
| | | | NM_002305.5 | exon 17-18 | 2659 | | |
| 14 | LCA5 | HS01099550_m1 | NM_001322789.2 | exon 6-7 | 1558 | 66 | Target |
| | | | NM_133714.3 | exon 7-8 | 1713 | | |
| 15 | GPR98 | Hs01022907_m1 | NM_532319.3 | exon 31-32 | 7041 | 62 | Target |
| 16 | RSPO3 | Hs01072567_m1 | NM_032784.3 | exon 1-2 | 388 | 77 | Target |
| 17 | STC1 | Hs00174970_m1 | NM_003155.2 | exon 1-2 | 404 | 81 | Target |
| 18 | STC2 | Hs00175027_m1 | NM_008714.2 | exon 2-3 | 1608 | 72 | Target |
| 19 | SLC7A11 | Hs00921938_m1 | NM_014331.3 | exon 7-8 | 1194 | 57 | Target |
| | Reference Genes | | | | | | |
| 20 | IPO8 | Hs00183533_m1 | NM_001190935.1 | exon 16-17 | 1977 | 71 | Reference |
| | | | NM_006390.3 | exon 20-21 | 1619 | | |
| 21 | TFRC | Hs00951053_m1 | NM_083128148.1 | exon 16-17 | 1818 | 66 | Reference |
| | | | NM_003234.2 | exon 16-17 | 1959 | | |
| 22 | UBC | Hs00824723_m1 | NM_023009.5 | exon 1-2 | 454 | 71 | Reference |
| 23 | PGK1 | Hs99995906_m1 | NM_000291.3 | exon 4-5 | 598 | 75 | |

*ABI-Applied Biosystems Life Technologies

TABLE 10A

Representative Amplicons for the Biomarkers of Table 10*

Target Genes

```
DACT3 (NM_145056.2)
Between bases 330-500
 330 c tgcctggtct cgtctgggac ctgggacagc
 361 agctgggaga cctgagcctg gagtctgggg gcctggaaca ggagagcggg cgtagctcgg
 421 gcttctatga agatcccagc tctacaggag gtccagattc accaccctca accttctgtg
 481 gggacagtgg cttctctgga (SEQ ID NO: 1)

JPH1 (NM_020647.2)
Between bases 1229-1375
1229 gc cgctcgccag gagtgcgaca tcgcgagagc
1261 tgtggccagg gagctgtcac ctgatttcta ccaaccaggc cctgattacg tcaaacagag
1321 atttcaggaa ggtgtagatg ctaaagaaaa tccagaagaa aaggtaccag aaaag
(SEQ ID NO: 2)

AKR1B10 (NM_020299.4)
Between bases 576-766
 576 agacc ccttgtgagg aaagcctttg
 601 agaagaccct caaggacctg aagctgagct atctggacgt ctatcttatt cactggccac
 661 agggattcaa gtctggggat gacctttttcc ccaaagatga taaggtaat gccatcggtg
 721 gaaaagcaac gttcttggat gcctggagg ccatggagga gctggt (SEQ ID NO: 3)

COL11A1 (NM_001190709.1)
Between bases 3907-4019
3907 gatg gaccacaagg accccccaggg tctgttggtt cagttggtgg tgttggagaa
```

TABLE 10A-continued

Representative Amplicons for the Biomarkers of Table 10*

```
3961 aagggtgaac ctggagaagc agggaaccca gggcctcctg gggaagcagg tgtaggcgg
(SEQ ID NO: 4)

SLC9A2 (NM_003048.3)
Between bases 352-514
 352 gtttacgct
 361 ggattacccc cacgtgcaga tccccttcga gatcaccctt tggatcctgc tggcctcct
 421 ggccaagatt ggcttccatc tgtatcacaa gttgcccaca atagtgcctg agagctgcct
 481 tcttataatg gttggacttc tactaggtgg gatt (SEQ ID NO: 5)

PDGFRL (NM_006207.2)
Between bases 1176-1314
1176 tttac tgcagggcgg aggccggggg
1201 cagatctcag atctccgtca agtaccagct gctctacgtg gcggttccca gtggccctcc
1261 ctcaacaacc atcttggctt cttcaaacaa agtgaaaagt gggg (SEQ ID NO: 6)

FCGBP (NM_003890.2)
Between bases 3334-3480
3334 ctggccac ctatgctgct gcatgccagg
3361 ctgctggagc cacagtgcac ccctggagga gtgaagaact tgcccactg agctgcccac
3421 cccacagcca ctatgaggcg tgttcctacg gctgcccgct gtcctgtgga gacctcccag
(SEQ ID NO: 7)

PRXX1 (NM_006902.3)
Between bases 223-357
 223 aggctggc cggagcctgc
 241 tggagtcgcc gggactcacc agcggcagcg acaccccgca gcaggacaat gaccagctga
 301 actcagaaga aaaaaagaag agaaagcagc gaaggaatag gacaaccttc aatagca
(SEQ ID NO: 8)

SERPINF1 (NM_002615.5)
Between bases 858-1026
 858 atg aagagaggac cgtgagggtc cccatgatgt cggaccctaa
 901 ggctgtttta cgctatggct tggattcaga tctcagctgc aagattgccc agctgccctt
 961 gaccggaagc atgagtatca tcttcttcct gccctgaaa gtgacccaga atttgaccttt
1021 gataga (SEQ ID NO: 9)

NGB (NM_021257.3)
Between bases 620-770
 620 t gtcctcactg gaggagtacc ttgccagcct gggcaggaag
 661 caccgggcag tgggtgtgaa gctcagctcc ttctcgacag tgggtgagtc tctgctctac
 721 atgctggaga agtgtctggg ccctgccttc acaccagcca cacgggctgc
(SEQ ID NO: 10)

SCUBE2 (NM_001170690.1)
Between bases 534-662
 534 ctgcaag
 541 gaggggtttt tcctgagtga caatcagcac acctgcattc accgctcgga agagggcctg
 601 agctgcatga ataaggatca cggctgtagt cacatctgca aggaggcccc aaggggcagc
 661 gt (SEQ ID NO: 11)

MAB21L (NM_006439.4)
Between 2265-2451
2265 tctgga cacaaacttt
2281 tatgtaagtc acctgaaata ggaatccggc agaagacctt cattaattaa gaagcaaaca
2341 aaaagagagc aacccaacca aaacaaatca cattcttgca caaagtgat cgttttcttc
2401 caaacaatgt gaatttaaaa ggtcacacaa agaagcaat cgggctccgc c
(SEQ ID NO: 12)

LEPR (NM_001003679.3)
Between bases 2593-2745
2593 ccattgag aagtaccagt tcagtcttta cccaatattt atggaaggag
2641 tgggaaaacc aaagataatt aatagtttca ctcaagatga tattgaaaaa caccagagtg
2701 atgcaggttt atatgtaatt gtgccagtaa ttatttcctc ttcca (SEQ ID NO: 13)

LCA5 (NM_001122769.2)
Between bases 1492-1624
1492 tttaactcc
1501 agaaacaatt atgtgttacg aaaacaaatg ggaagaacca ggacatctta ctttggactt
1561 gcaatctcaa aagcaagaca ggcatggaga agcagggatt ctaaacccaa ttatggaaag
1621 agaa (SEQ ID NO: 14)

GPR98 (NM_032119.3)
Between bases 6979-7103
6979 gc ccctggggaa accattcaaa ccttgttgtt agaggtcctg
7021 gctgacgacg ttccggagat tgaagaggtt atccaagtgc aactaactga tgcctctggt
7081 ggaggtacta ttgggttaga tcg (SEQ ID NO: 15)
```

TABLE 10A-continued

Representative Amplicons for the Biomarkers of Table 10*

RSPO3 (NM_032784.3)
Between bases 311-465
 311 ttggcttttt atcattttga actttatgga atacatcggc agccaaaacg
 361 cctcccgggg aaggcgccag cgaagaatgc atcctaacgt tagtcaaggc tgccaaggag
 421 gctgtgcaac atgctcagat tacaatggat gtttgtcatg taagc (SEQ ID NO: 16)

STC1 (NM_003155.2)
Between bases 323-485
 323 cagtgctt ctgcaaccca tgaggcggag cagaatgact
 361 ctgtgagccc caggaaatcc cgagtggcgg ctcaaaactc agctgaagtg gttcgttgcc
 421 tcaacagtgc tctacaggtc ggctgcgggg cttttgcatg cctggaaaac tccacctgtg
 481 acaca (SEQ ID NO: 17)

STC2 (NM_003714.2)
Between bases 1536-1680
1536 tgtga gattcggggc ttacatggga
1561 tttgcatgac ttttctgcac aacgctgaaa aatttgatgc ccagggcaag tcattcatca
1621 aagacgcctt gaaatgtaag gcccacgctc tgcggcacag gttcggctgc ataagccgga
(SEQ ID NO: 18)

SLC7A11 (NM_014331.3)
Between bases 1137-1251
1137 tggc
1141 ctactttacg accattaatg ctgaggagct gctgctttca aatgcagtgg cagtgacctt
1201 ttctgagcgg ctactgggaa atttctcatt agcagttccg atctttgttg c
(SEQ ID NO: 19)

Reference Genes

IPO8 (NM_001190995.1)
Between bases 1906-2048
1906 agatg cagagtgtca
1921 tgcagctaaa cttctggaag tcatcattct tcagtgcaaa ggaaggggaa ttgatcagtg
1981 cattccactc ttcgttcaac ttgttttgga gagattaact cgagggtca aaactagtga
2041 gcttcgta (SEQ ID NO: 20)

TFRC (NM_001128148.1)
Between bases 1752-1884
1752 tagacaatg ctgctttccc tttccttgca tattctggaa tcccagcagt
1801 ttctttctgt ttttgcgagg acacagatta tcctfatttg ggtaccacca tggacaccta
1861 taaggaactg attgagagga ttcc (SEQ ID NO: 21)

UBC (NM_021009.5)
Between bases 383-525
 383 ggcacagc tagttccgtc gcagccggga tttgggtcgc
 421 agttcttgtt tgtggatcgc tgtgatcgtc acttgacaat gcagatcttc gtgaagactc
 481 tgactggtaa gaccatcacc ctcgaggttg agcccagtga cacca (SEQ ID NO: 22)

PGK1 (NM_000291.3)
Between bases 523-673
 523 cctgctgg agaacctccg
 541 cttttcatgtg gaggaagaag ggaagggaaa agatgcttct gggaacaagg ttaaagccga
 601 gccagccaaa atagaagctt tccgagcttc actttccaag ctaggggatg tctatgtcaa
 661 tgatgctttt ggc (SEQ ID NO: 23)

*The sequences represent embodiments of amplified areas of the biomarker gene and preferred locations of probe/primers are highlighted. Probes can be, for example, 13-18 base pairs and an area of 25 base pairs is highlighted.

d. Study Design and End Points

The gene expression signature was developed in a training set composed of archival formalin-fixed paraffin-embedded tumor blocks of patients with thymomas. All steps of the assay including the prognostic algorithm were fully developed, completely specified, and technically validated in compliance with CLIA-laboratory guidelines before initiation of the independent validation study.

The primary end point was to determine whether the 19 gene expression profile can classify the patients into low or high risk metastasis group based on the 5 years or 10 years metastasis free survival (MFS), mainly measuring its prognostic value. The secondary end point was to evaluate its predictive power in comparison with traditional prognostic methods such as the WHO histological type and Masoaka staging system, and determine whether it strengthens the prediction of the likelihood of metastasis in combination with the clinicopathological parameters.

e. Statistical Analysis

Using a training set, multiple nonlinear predictive modeling methods were performed to assess the prognostic ability of the GEP assay. In addition to RBM, partition tree analysis, K-nearest neighbor analysis, and distance scoring analysis were performed using the SAS-based JMP Genomics software. The area under the receiver operator characteristic curve (ROC) was calculated for each analysis to assess the predictive probabilities of each method. Metastasis-free survival (MFS) was assessed by Kaplan-Meier analysis using JMP Genomics. Probabilities were calculated according to the Log-Rank method. Cox univariate and multivariate regression analyses were performed using Win-STAT software for the variables age, gender, autoimmune disease, residual disease, stage (I/II vs. III/IV) and GEP. 95% confidence interval (95% CI) ranges for hazard ratios were calculated using WinSTAT.

Figure 7B:
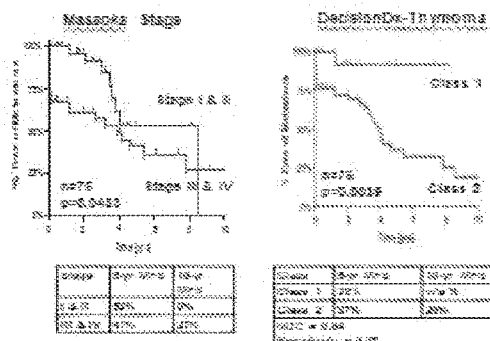

Results:

a. Prognostic Impact of Stage and WHO Histological Type in the Training and Validation Cohorts In the training set sample cohort, Kaplan-Meier analysis was performed to generate MFS curves. Ten-year MFS was 0% for stage III/IV and 80% for patients with stage I/II disease (FIG. 7A). WHO classification analysis was condensed to three groups: tumors that predominantly follow a benign course (types A, AB, and B1), tumors that are thought to be low-grade malignant (type B2) and tumors that can have an aggressive course (B3). Training set 10-year MFS rates were 64%, 36% and 27% for groups A/AB/B1, B2, and B3, respectively (FIG. 7B).

Figure 7C:
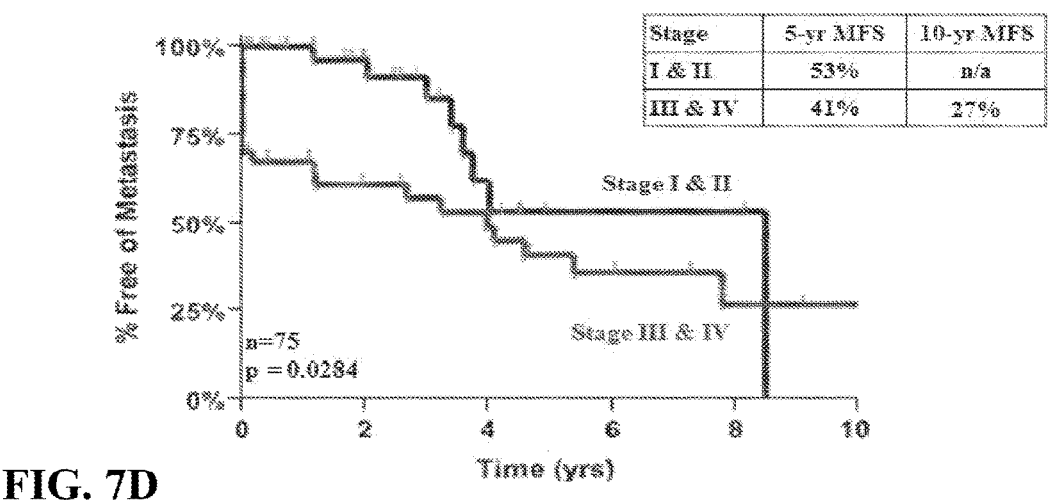

RBM analysis of gene expression data in the training set cohort of samples yielded a predictive model with an area under the receiver operating characteristic (ROC) curve of 0.89, reflecting a highly accurate model. In comparison to Masaoka staging and WHO classification, GEP exhibited 5- and 10-year MFS rates of 85% for predicted Class 1, and 22% for high risk Class 2 samples (FIG. 7C, p=0.0005).

The independent validation set consisted of 75 cases. Kaplan-Meier curves were generated after grouping samples according to Masoaka stage and censoring on metastatic event. The 5- and 10-year MFS rates were 41% and 20% for Stage III and IV samples, respectively. The 5-year MFS rate was 53% for Stage I&II samples, while 10-year rate was not reached (FIG. 7C). For the three WHO groups analyzed, 5- and 10-year MFS rates were 59% and 25%, 36% and 0%, and 28% and 28% for groups A/AB/B1, B2, and B3, respectively (FIG. 7C).

Figure 7D:
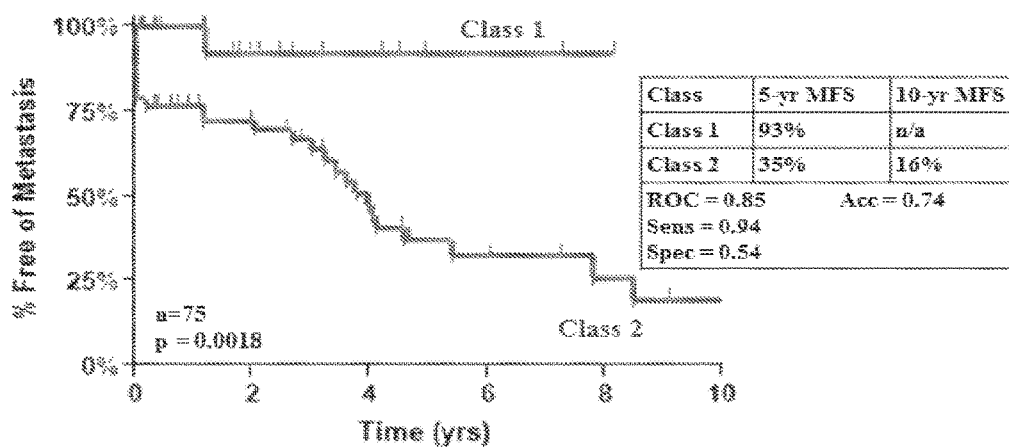
Figure 8A:
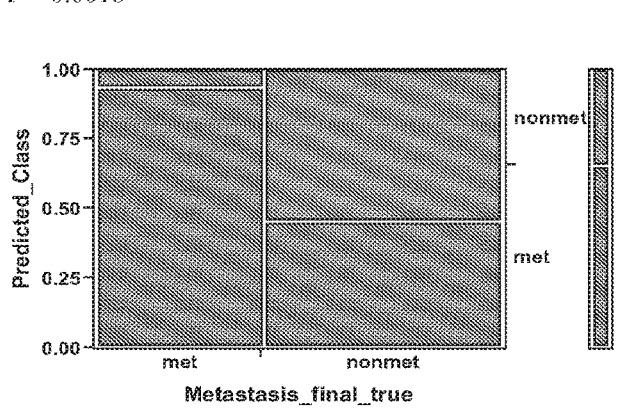
FIGS. 8A-8J show the results of various gene combinations used to predict metastatic risk in thymoma tumors using a JMP Genomics radial basis machine (RBM) kernel-based learning algorithm.
Figure 8A:
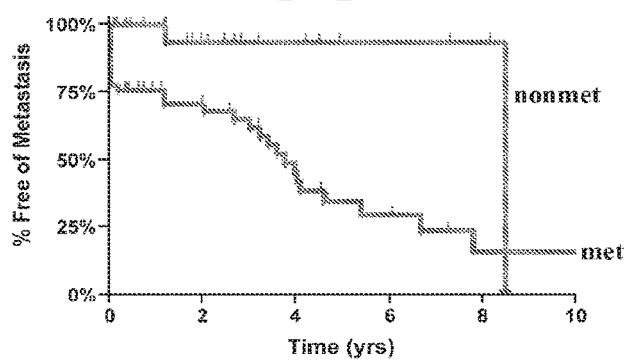
Figure 8B:
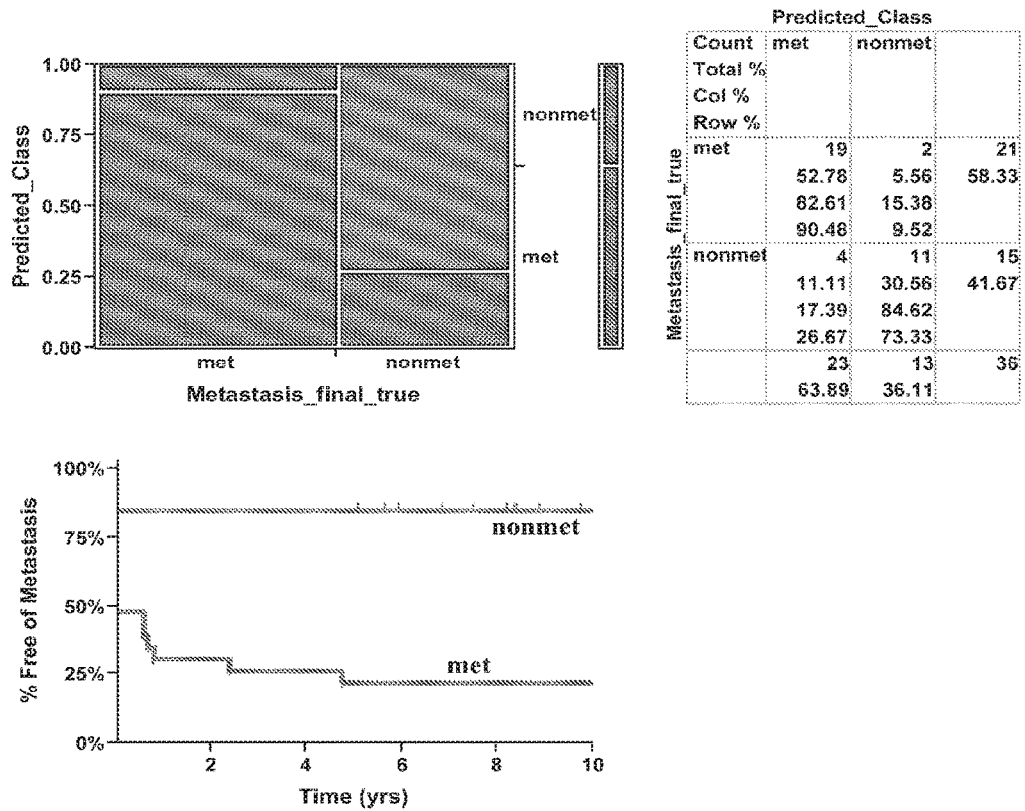
Figure 8C:
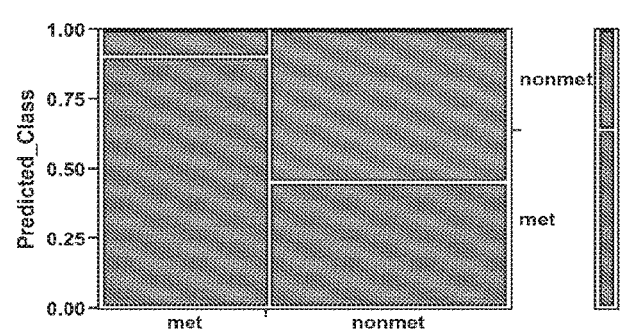
Figure 8C:
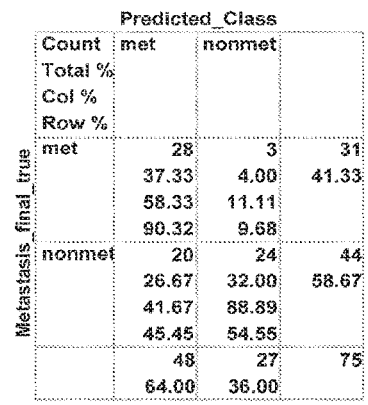
Figure 8C:
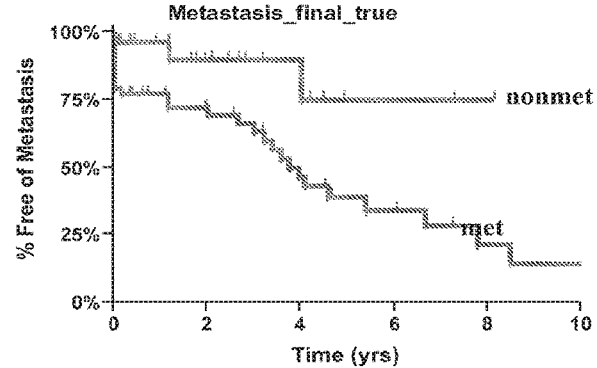
Figure 8D:
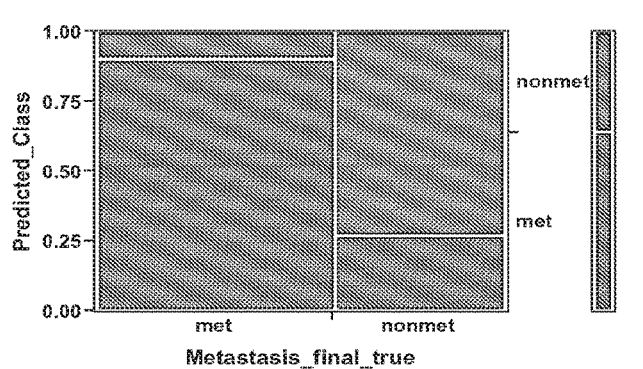
Figure 8D:
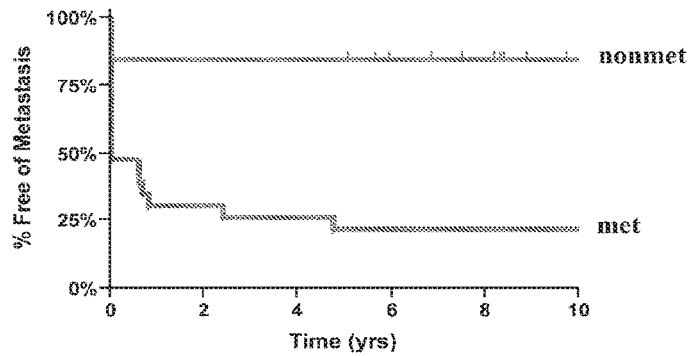
Figure 8E:
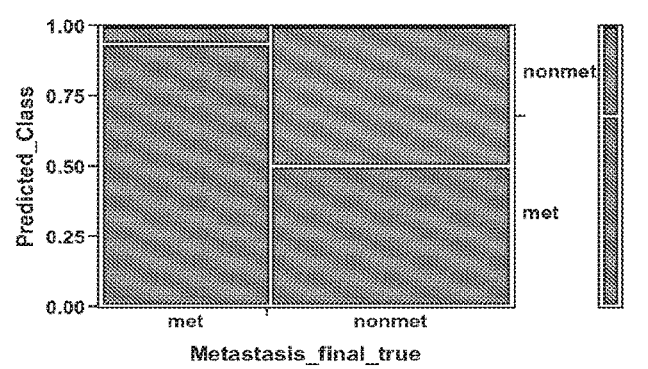
Figure 8E:
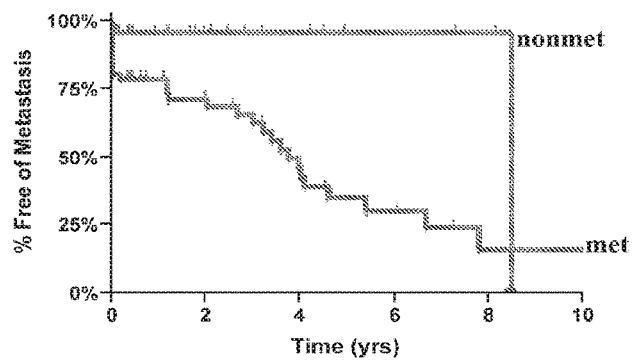
Figure 8F:
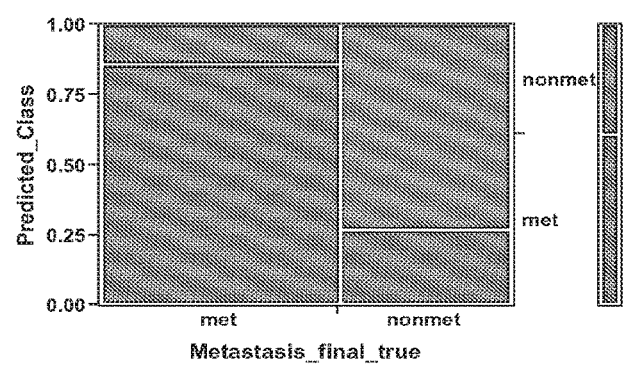
Figure 8F:
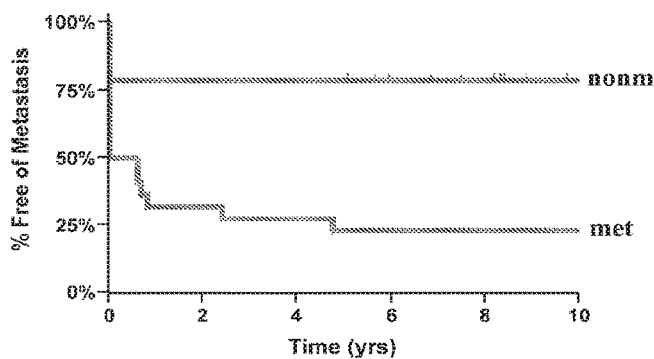
Figure 8G:
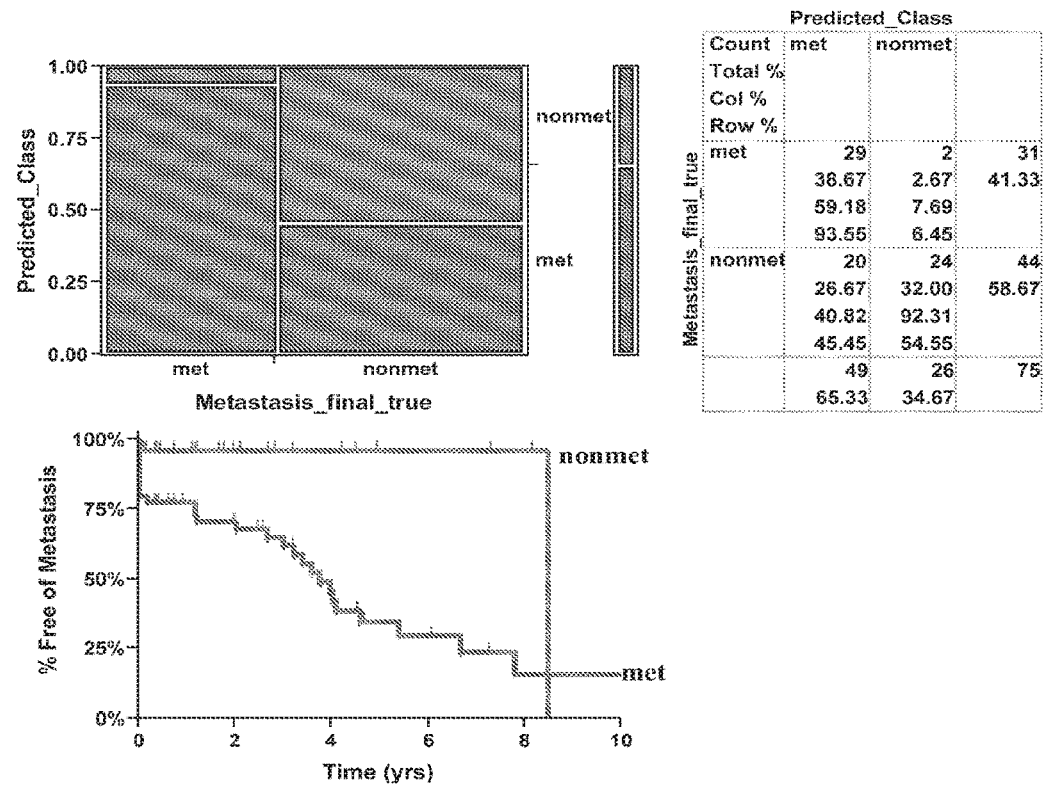
Figure 8H:
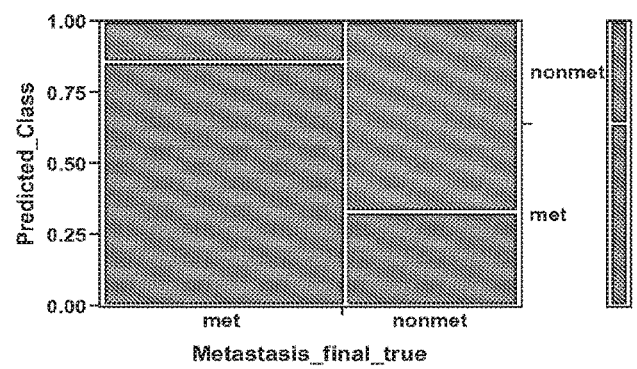
Figure 8H:
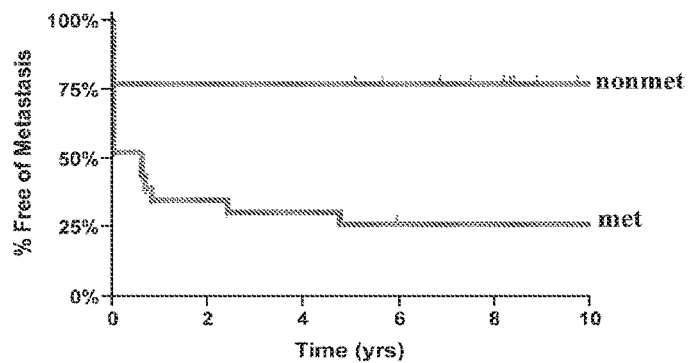
Figure 8I:
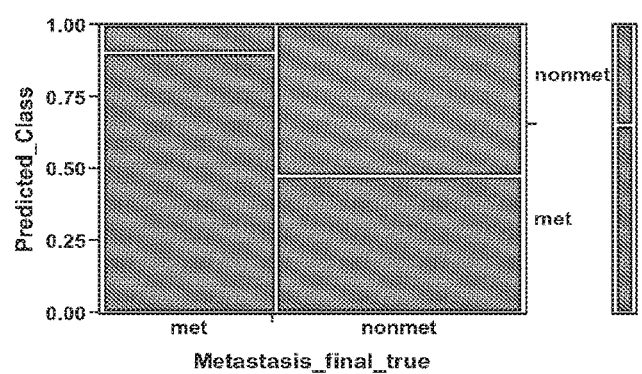
Figure 8I:
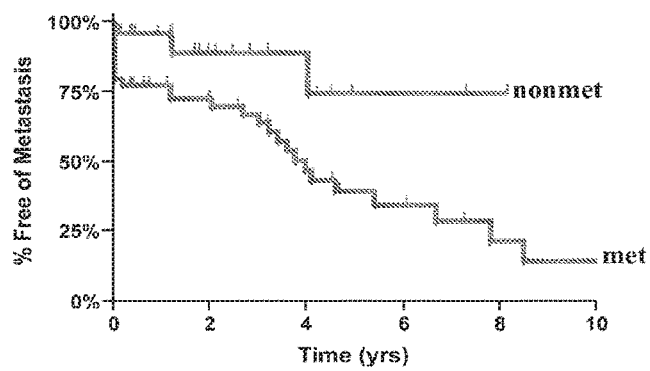
Figure 8J:
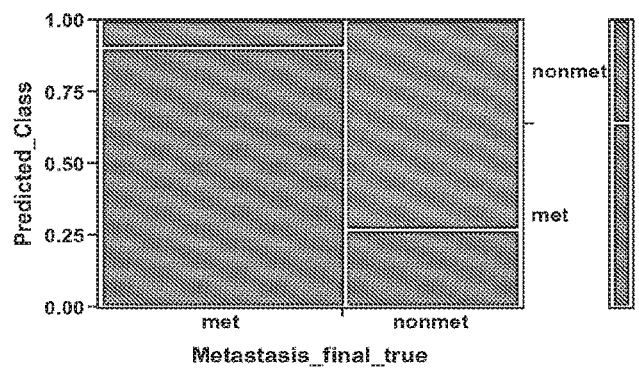
Figure 8J:
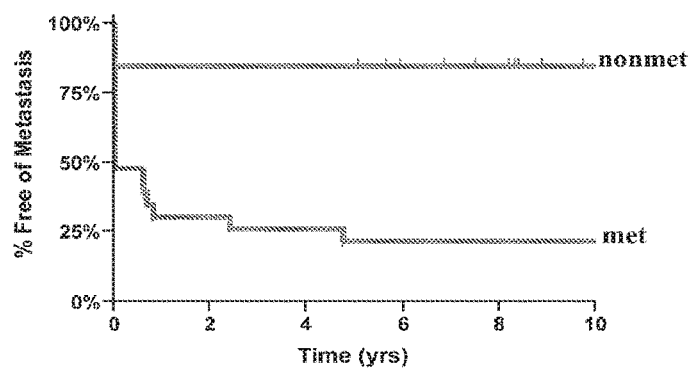

The GEP identified 26 patients as Class 1 and 49 patients as Class 2, and had a sensitivity of 94%. Kaplan-Meier analysis revealed a highly significant difference in MFS between the two classes. 5-year survival was 93% for Class 1, while 10-year MFS was not reached in the cohort (FIG. 7D). Conversely, 5- and 10-year MFS for Class 2 samples was 35% and 16%, respectively (p=0.0018).

b. Accuracy of Predictive Models in the Low- and High-Risk Groups

Measure of the area under the ROC curve reflects the efficiency of the model (or training set expression signature) for predicting metastasis, and a perfect model would have an ROC of 1. In the current study the 19-gene signature provided a high degree of model accuracy when used to predict the training set and validation set sample class (low risk or high risk class). The 36 sample training set had an ROC of 0.89 using the RBM method, while the 75-sample cohort had an ROC of 0.85. By definition, prognosis for both cohorts would be highly useful clinically. By comparison, metastasis prediction models based on Masaoka stage had ROC values of 0.88 and 0.71 for the training and validation cohorts, respectively.

Overall prognostic accuracy for prediction of metastasis in the validation cohort was a comparable 74% and 70% for the objective GEP assay and the Masaoka staging system, respectively. However, the accuracy of metastasis prediction, observed as the sensitivity, was 94% using the GEP method and only 74% by Masaoka stage. This discrepancy is reflected in the MFS rates described in the previous section, and results in positive predictive values of 59% and 61% using the GEP and stage prognostic methods, respectively. Conversely, the negative predictive values using GEP is 92%, and 78% using histologic stage.

c. Univariate and Multivariate Cox Regression Analysis of Clinical Factors in Relation to the Prediction of Metastasis Cox proportional hazards regression analysis was performed to determine the power of the 19-gene signature with regards to other clinico-pathological parameters. In univariate Cox analysis, GEP was a strong prognostic factor with a hazard ratio of 10.17 (95% CI=1.38-75.04; p value=0.023). Stage I/II vs. Stage III/IV also was a strong, but insignificant predictor of the likelihood for metastasis in the independent validation cohort, having a hazard ratio of 2.25 (95% CI=0.985-5.14; p-value=0.054). Age at diagnosis, gender, autoimmune disease, and presence or absence of residual disease after surgery, were not significantly associated with the likelihood of metastasis and were not included in multivariate analysis. WHO classification was also a factor unassociated with metastatic risk prognosis, but was included in the multivariate comparison because of its clinical relevance. Thus, multivariate analysis of stage and GEP demonstrated that the 19 gene signature is an independent predictor of metastasis risk. The hazard ratio for GEP determination of risk was 8.66 (95% CI=1.14-65.59; p value=0.036), whereas tumor stage and WHO type, either used singly or in combination, did not significantly contribute to the prediction of metastasis risk, having hazard ratios of 1.54 (95% CI=0.662-3.59, p-value=0.316) and 1.29 (95% CI=0.794-2.11, p-value=0.302), respectively. These results are summarized in Table 11.

TABLE 11

Summary of MFS Analysis in the Independent 75-Sample Validation Set.

|  | Cox univariate analysis HR (p-value) | Cox multivariate analysis HR (p-value) | Kaplan-Meier p-value |
|---|---|---|---|
| GEP Class 2 | 10.2 (0.023) | 7.76 (0.048) | 0.0018 |
| Stage III/IV | 2.25 (0.054) | 1.54 (0.316) | 0.0702 |
| WHO malignant class | 1.60 (0.056) | 1.29 (0.302) | 0.0325 |
| Age >50 years | 0.49 (0.068) | — | — |
| Gender | 0.69 (0.325) | — | — |
| Autoimmune disease | 1.17 (0.701) | — | — |
| Performance status - RD | 2.16 (0.095) | — | — | c. Molecular Signature is Independent of the Model Used and Prognostic Accuracy is Achieved with Multiple Predictive Modeling Methods Other nonlinear predictive modeling methods, such as Partition Tree Analysis, K-Nearest Neighbor, and Distance Scoring, were applied to determine the accuracy of modeling algorithms for predicting metastasis in the independent 75-sample thymoma validation set. As shown in Table 12, scores for the area under the ROC curves greater than 0.8 were achieved using each of the algorithms. These results indicate that each of the models is accurate and useful for predicting the metastatic risk associated with thymomas. The 19 marker set assay was chosen to be developed using the RBM algorithm because that method provided the highest sensitivity.

TABLE 12

Accuracy of Non-Linear Modeling Algorithms for Predicting Metastatic Risk in a 75-Sample Thymoma Validation Set.

| Predictive Model | ROC | Sensitivity | K-M P-value (Log-Rank) |
|---|---|---|---|
| Radial Basis Machine | 0.85 | 0.94 | 0.0018 |
| K-Nearest Neighbor | 0.85 | 0.81 | 0.0023 |

TABLE 12-continued

Accuracy of Non-Linear Modeling Algorithms for Predicting
Metastatic Risk in a 75-Sample Thymoma Validation Set.

| Predictive Model | ROC | Sensitivity | K-M P-value (Log-Rank) |
|---|---|---|---|
| Partition Tree | 0.83 | 0.81 | 0.0007 |
| Distance Scoring | 0.82 | 0.84 | 0.0061 | d. Summary

Accordingly, a gene expression signature was developed and validated, and its prognostic value was compared against other clinicopathological parameters. Age at diagnosis, gender, autoimmune disease and histologic subtype (WHO) were not significant predictors. Stage was the only variable other than GEP that approached significance in univariate analysis. Multi-variate analyses confirm that the 19-gene signature was an independent predictor of metastasis free survival and superior to Masoaka staging system. Thus, the GEP assay is the first known prognostic molecular marker that can accurately determine the risk of metastasis associated with thymomas.

Overexpression of 6 genes (AKR1B10, STC1, STC2, JPH1, NGB, SLC7A11), and down-regulation of 13 genes (DACT3, COL11A1, SLC9A2, PDGFRL, FCGBP, PRRX1, SERPINF1, SCUBE2, MAB21L2, LEPR, LCA5, GPR98 and RSOP3) was noted in patients with high risk. The up-regulated genes have been previously associated with invasion and metastasis or chemo-resistance in multiple cancers. Stanniocalcins particularly, STC2, can induce epithelial to mesenchymal transformation (EMT) and are associated with invasion (Law and Wong (2010) *Exp. Cell. Res.* 316:3425-3434; Volland et al. (2009) *J. Intl. Du. Cancer* 125:2049-2057) and reduced overall survival rate in neuroblastoma, colon and gastric cancer (Volland et al. (2009) *J. Intl. Du. Cancer* 125:2049-2057; Ieta et al. (2009) *J. Intl. Du. Cancer* 125:926-931; Yokobori et al. (2010) *Annal. Surg. Oncol.* 17:2601-2607) and tumor dormancy in breast cancer (Joensuu et al. (2008) *Canc. Lett.* 265:76-83). Aldo-keto reductase 1B10 (AKR1B10) is linked to chemoresistance to drugs such as doxorubicin and daunorubicin (ref). JPH1 up-regulation is seen in neuroblastoma patients with poor-outcomes (Wei et al. (2004) *Canc. Res.* 64:6883-6891). Solute carrier family 7, member 11 (SLC7A11) plays an important role in tumor growth, invasion and tumor metastasis (Kondo et al. (2001) *J. Surg. Oncol.* 76:169-175; Takahashi et al. (2003) *Hum. Pathol.* 34:1253-1258; Sogawa et al. (2003) *Cancer* 98:1822-1829; Sasaki et al. (2003) *Cancer Sci.* 94:809-813; Tateyama et al. (2011) *Hum. Pathol.* 42:533-540; Sasaki et al. (2002) *J. Intl. Du. Cancer* 101:342-347). It has also been implicated in resistance to Cisplatin, commonly used to treat thymic neoplasms.

The genes described herein are novel in the context of thymomas but based on the knowledge in other cancers might serve as potential therapeutic candidates. In this context, the first thymoma cell line (IU-TAB-1) derived from a patient with stage II thymoma, WHO type AB has been established (Gökmen-Polar et al, Laboratory Investigation in press). The expression levels of STC1, STC2 and AKR1B10 in IU-TAB-1 cell line were, as expected, low. Further mechanistic studies including knock-in and knock-out approaches, are being undertaken to assess the therapeutic potential of these genes.

The current retrospective study was based on multi-institutional samples with patients receiving different surgical and post-surgical treatments. The surgical management was provided at local centers in a large number of cases and assessment of extent of disease and residual disease status is based on the assessment at these centers. In addition, the decision to administer adjuvant chemotherapy and/or radiation was made by local physicians. This can be considered as a strength of the study as it permits generalization of the results to patients with thymomas and enable personalized management based on their risk. Additionally, prospective evaluation of the assay in a randomized clinical trial can be conducted.

These results have been further validated, as shown in FIGS. 7A-7D. In addition, analysis of various gene combinations used to predict metastatic risk in thymoma tumors using JMP Genomics radial basis machine (RBM) kernel-based learning algorithm has been performed and validated (FIGS. 8A-8J). For each genetic signature results are shown for both a 36-sample optimized training set and a 75-sample validation set. Data include 1) mosaic plots and contingency tables to illustrate the true and predicted number of metastatic and non-metastatic samples; 2) Kaplan Meier curves to illustrate metastasis-free survival in each sample cohort; 3) the area under the receiver operator characteristics (ROC) curves to indicate accuracy of the model developed; 4) accuracy, sensitivity, and specificity of the predictions for each signature; 5) 5- and 10-year metastasis-free survival values based upon K-M analysis; and 6) p-values to reflect significance of difference between low risk and high risk curves from K-M analysis.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

What is claimed is:

1. A kit for detecting thymic cancer, the kit consisting of a plurality of synthetic, fluorescently labeled modified probes or a plurality of synthetic, fluorescently labeled-modified oligonucleotide primer pairs, wherein said probes or primers are modified with fluorescent labels for detection, and wherein a) each synthetic, fluorescently labeled modified probe specifically binds to one distinct biomarker, fragment or variant thereof of a biomarker panel or b) each synthetic, fluorescently labeled modified oligonucleotide primer pair specifically amplifies a distinct biomarker, fragment or variant thereof of the biomarker panel, wherein the biomarker panel is selected from a panel correlated with high or low risk of metastasis associated with thymoma, or early or late stage thymoma, and consisting of JPH1, ALDH1A3, SPOCK1, NGB, STC2, AKR1B10, ENPEP, GOLSYN, RPL39, LAMP2, ABHD7, RBPMS2, C9orf93, SESN3, MRRF, NEBL, PRRX1, C14orf39, LEPR, DTNA, LCA5, RSPO3, IGF2BP2, GPR98, TIAM2, SLC9A2, MAB21L2, SCUBE2, DACT3, COL11A1 and SLC7A11; or a panel consisting of COL11A1, DACT3, SLC9A2, PRRX1, PDGFRL, SCUBE2, MAB21L2, FCGBP, MAOA, CTGF, NEBL, GPR98, GLDN, IGSF11, PCDH19, C6orf118, GOLSYN, BCMO1, PTN, LAMP2, LRRC17, DDX60, GEM, FRMD6, KGFLP1, C9orf93, NGB, AKR1B10, JPH1, STC2, and SLC7A11; or a panel correlated with high or low risk of metastasis associated with thymic cancer, or early or late stage thymic cancer, and consisting of DACT3, JPH1, AKR1B10, COL11A1, SLC9A2, PDGFRL, FCGBP, PRRX1, SERPINF1, NGB, SCUBE2, MAB21L2, LEPR, LCA5, GPR98, RSPO3, STC2 and SLC7A11;

and optionally a control or reference sample, wherein the control or reference sample consists of a) at least one synthetic, fluorescently labeled modified probe that binds specifically to one of IP08, TFRC, UBC, PGK1, and GAPDH or b) at least one synthetic, fluorescently labeled modified oligonucleotide primer pair that specifically amplifies one of IP08, TFRC, UBC, PGK1, and GAPDH.

2. The kit of claim 1, wherein the plurality of synthetic, fluorescently labeled modified probes are nucleic acid probes or recombinant antibodies.

3. A kit for detecting thymic cancer, the kit consisting of a plurality of synthetic, fluorescently labeled modified probes or a plurality of synthetic, fluorescently labeled-modified oligonucleotide primer pairs, wherein said probes or primers are modified with fluorescent labels for detection, and wherein a) each synthetic, fluorescently labeled modified probe specifically binds to one distinct biomarker, fragment or variant thereof of a biomarker panel or b) each synthetic, fluorescently labeled modified oligonucleotide primer pair specifically amplifies a distinct biomarker, fragment or variant thereof of the biomarker panel, wherein the biomarker panel is selected from a panel correlated with high or low risk of metastasis associated with thymoma, or early or late stage thymoma, and consisting of JPH1, ALDH1A3, SPOCK1, NGB, STC1, STC2, AKR1B10, ENPEP, GOLSYN, RPL39, LAMP2, ABHD7, RBPMS2, C9orf93, SESN3, MRRF, NEBL, PRRX1, C14orf39, LEPR, DTNA, LCA5, RSPO3, IGF2BP2, GPR98, TIAM2, SLC9A2, MAB21L2, SCUBE2, DACT3, COL11A1 and SLC7A11; or a panel consisting of COL11A1, DACT3, SLC9A2, PRRX1, PDGFRL, SCUBE2, MAB21L2, FCGBP, MAOA, CTGF, MET, NEBL, GPR98, GLDN, IGSF11, PCDH19, C6orf118, GOLSYN, BCMO1, PTN, LAMP2, LRRC17, DDX60, GEM, FRMD6, KGFLP1, C9orf93, NGB, AKR1B10, JPH1, STC1, STC2, and SLC7A11; or a panel correlated with high or low risk of metastasis associated with thymic cancer, or early or late stage thymic cancer, and consisting of DACT3, JPH1, AKR1B10, COL11A1, SLC9A2, PDGFRL, FCGBP, PRRX1, SERPINF1, NGB, SCUBE2, MAB21L2, LEPR, LCA5, GPR98, RSPO3, STC1, STC2 and SLC7A11;

and optionally, a control or reference sample, wherein the control or reference sample consists of a) at least one synthetic, fluorescently labeled modified probe that binds specifically to one of IP08, TFRC, UBC, PGK1 and GAPDH or b) at least one synthetic, fluorescently labeled modified oligonucleotide primer pair that specifically amplifies one of IP08, TFRC, UBC, PGK1 and GAPDH.

* * * * *